(12) United States Patent
Elliman

(10) Patent No.: US 8,656,911 B2
(45) Date of Patent: Feb. 25, 2014

(54) ACTUATION COUNTER

(75) Inventor: David Vincent Elliman, Sudbury (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 307 days.

(21) Appl. No.: 12/867,897

(22) PCT Filed: Feb. 17, 2009

(86) PCT No.: PCT/EP2009/051876
§ 371 (c)(1),
(2), (4) Date: Aug. 17, 2010

(87) PCT Pub. No.: WO2009/103711
PCT Pub. Date: Aug. 27, 2009

(65) Prior Publication Data
US 2010/0313884 A1    Dec. 16, 2010

Related U.S. Application Data

(60) Provisional application No. 61/029,458, filed on Feb. 18, 2008.

(51) Int. Cl.
*A61M 15/00* (2006.01)
(52) U.S. Cl.
USPC ............ 128/203.12; 128/203.15; 128/205.23
(58) Field of Classification Search
None
See application file for complete search history.

(56) References Cited

U.S. PATENT DOCUMENTS

| 5,421,482 A | 6/1995 | Garby et al. |
| 2006/0151524 A1* | 7/2006 | Stradella et al. ............... 222/23 |
| 2009/0101150 A1* | 4/2009 | Stradella et al. ......... 128/205.23 |
| 2009/0139516 A1 | 6/2009 | Augustyn et al. |

FOREIGN PATENT DOCUMENTS

| GB | 2191032 A | 12/1987 |
| WO | 2005/079727 A2 | 9/2005 |
| WO | 2006110080 A | 10/2006 |
| WO | 2007/034237 A1 | 3/2007 |
| WO | 2007104964 A | 9/2007 |
| WO | 2007124406 A | 11/2007 |
| WO | 2008/110584 A | 9/2008 |

* cited by examiner

*Primary Examiner* — Loan Thanh
*Assistant Examiner* — Andrew S Lo
(74) *Attorney, Agent, or Firm* — Robert J. Smith

(57) ABSTRACT

There is provided an actuation counter comprising a driver feature having one or more driver elements, which driver feature is arranged for drivable movement in response to an actuation; and a count member including one or more drive receipt elements arranged thereon for receipt of drive from said one or more driver elements of the driver feature for drivable movement of the count member. The driver feature includes one or more brake elements arranged to selectively interact with the count member to prevent overrun thereof when registering a count of an actuation. The actuation is suitably arranged for use with a drug dispenser device.

27 Claims, 49 Drawing Sheets

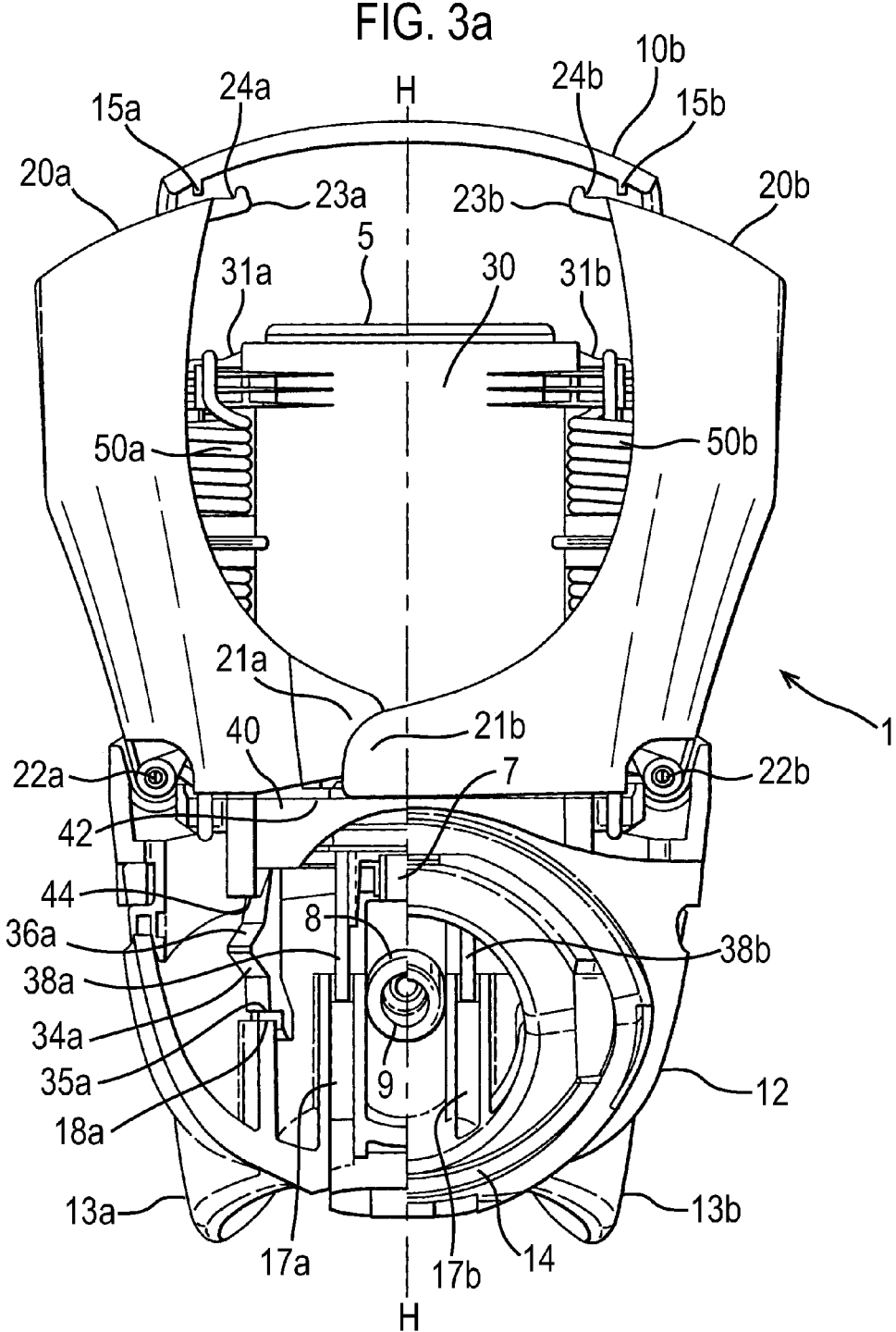

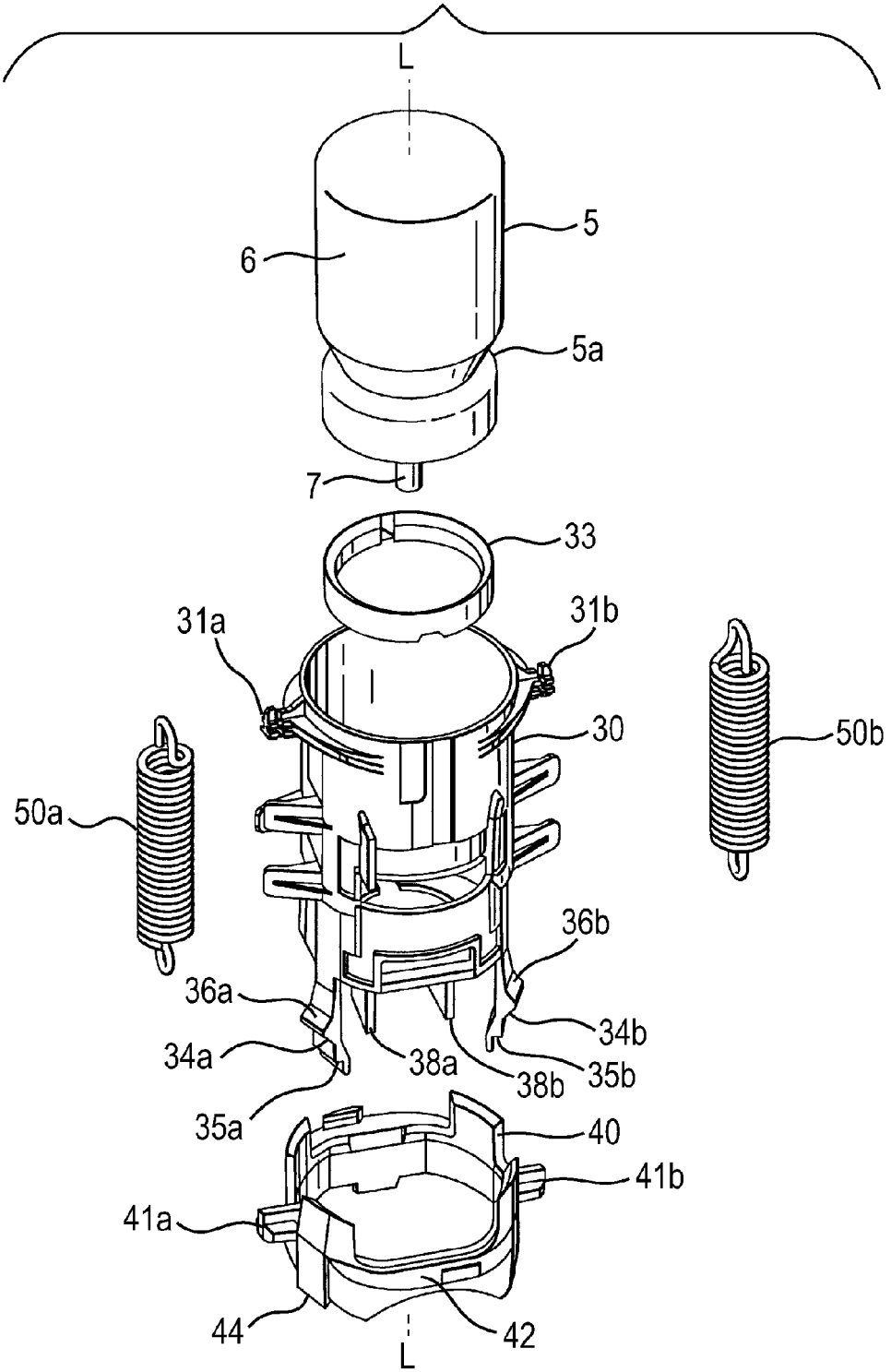

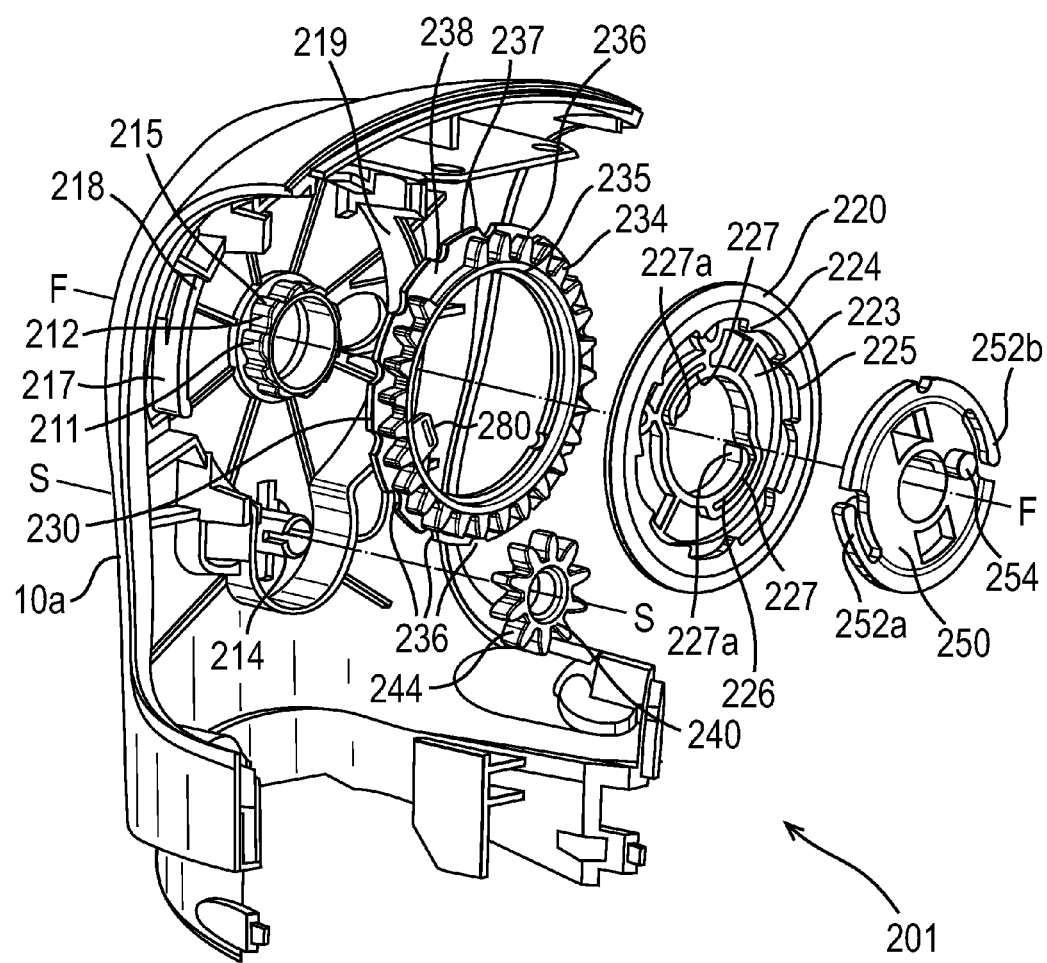

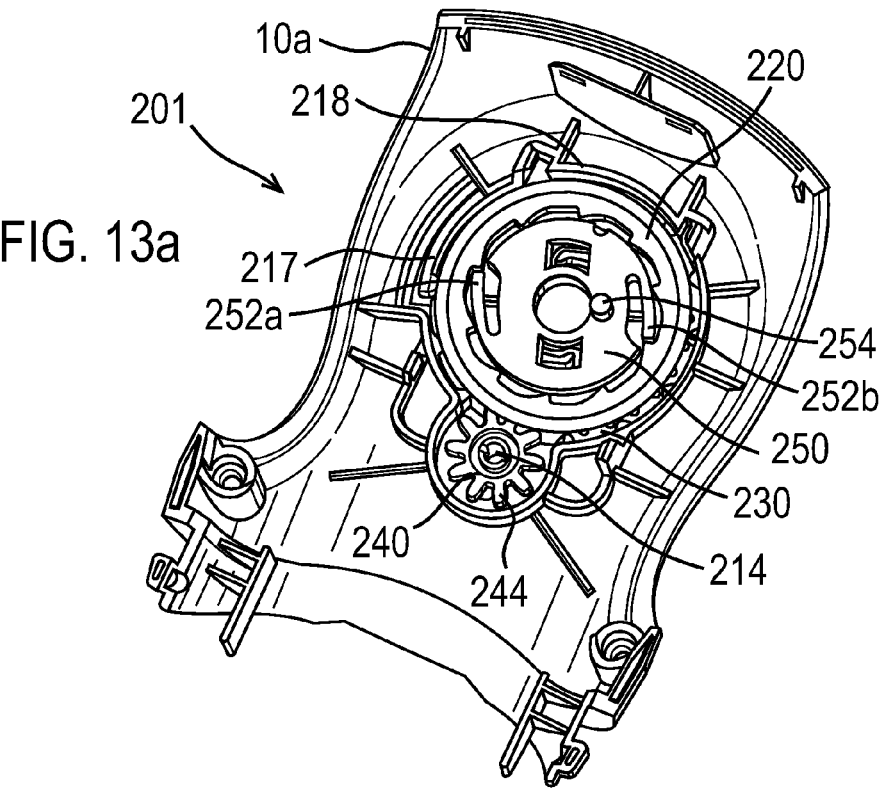
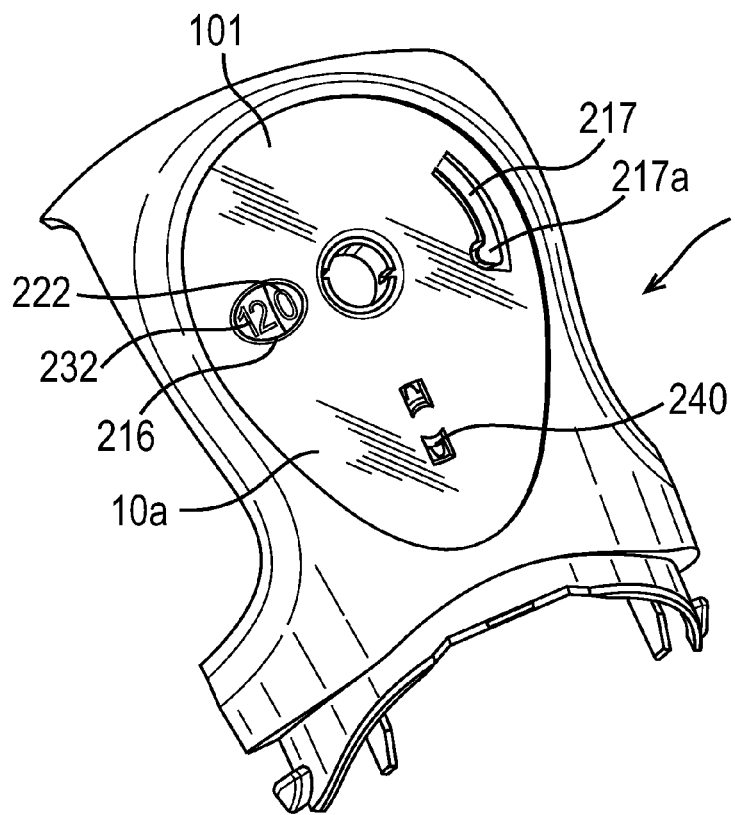

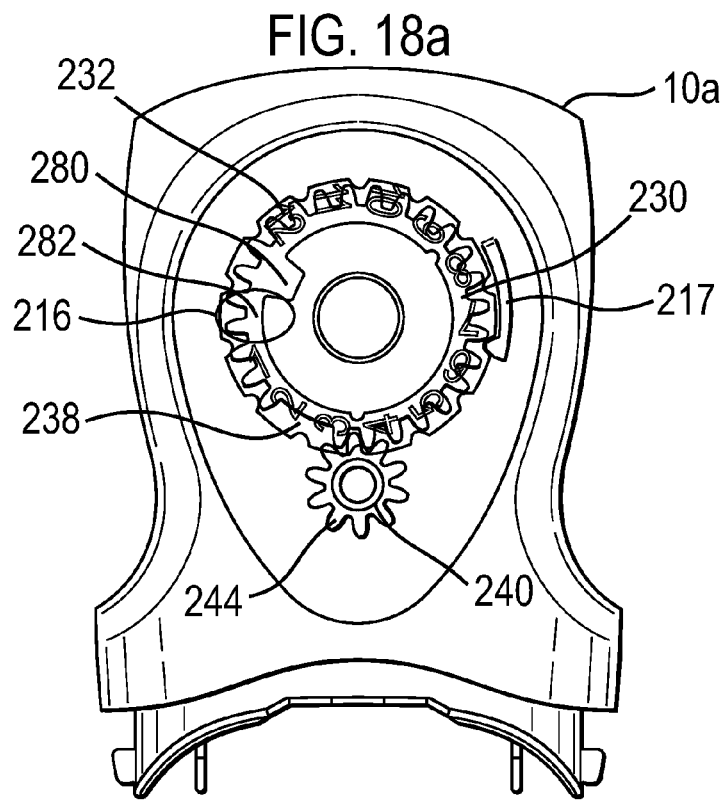
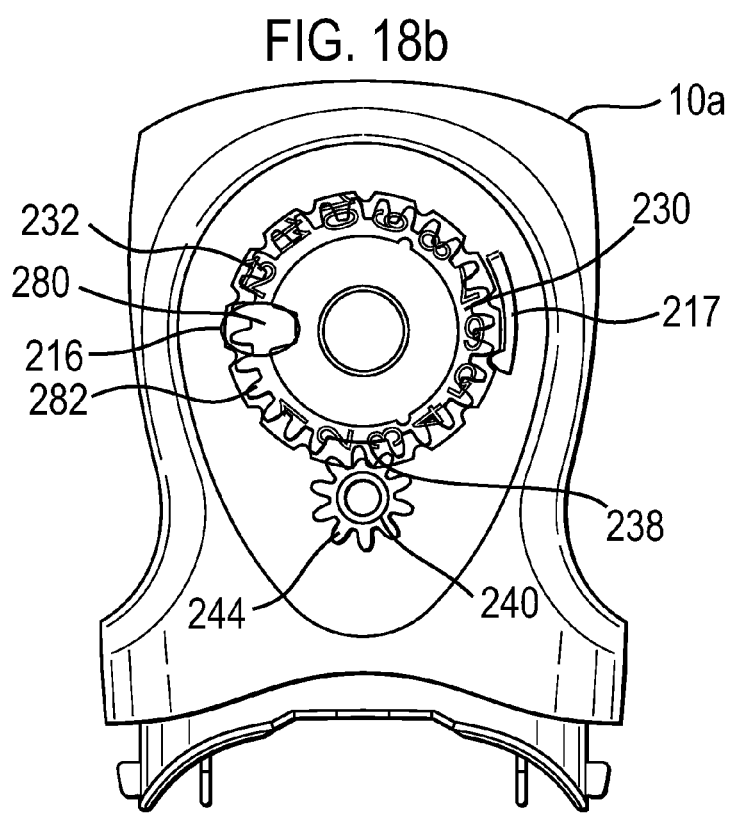

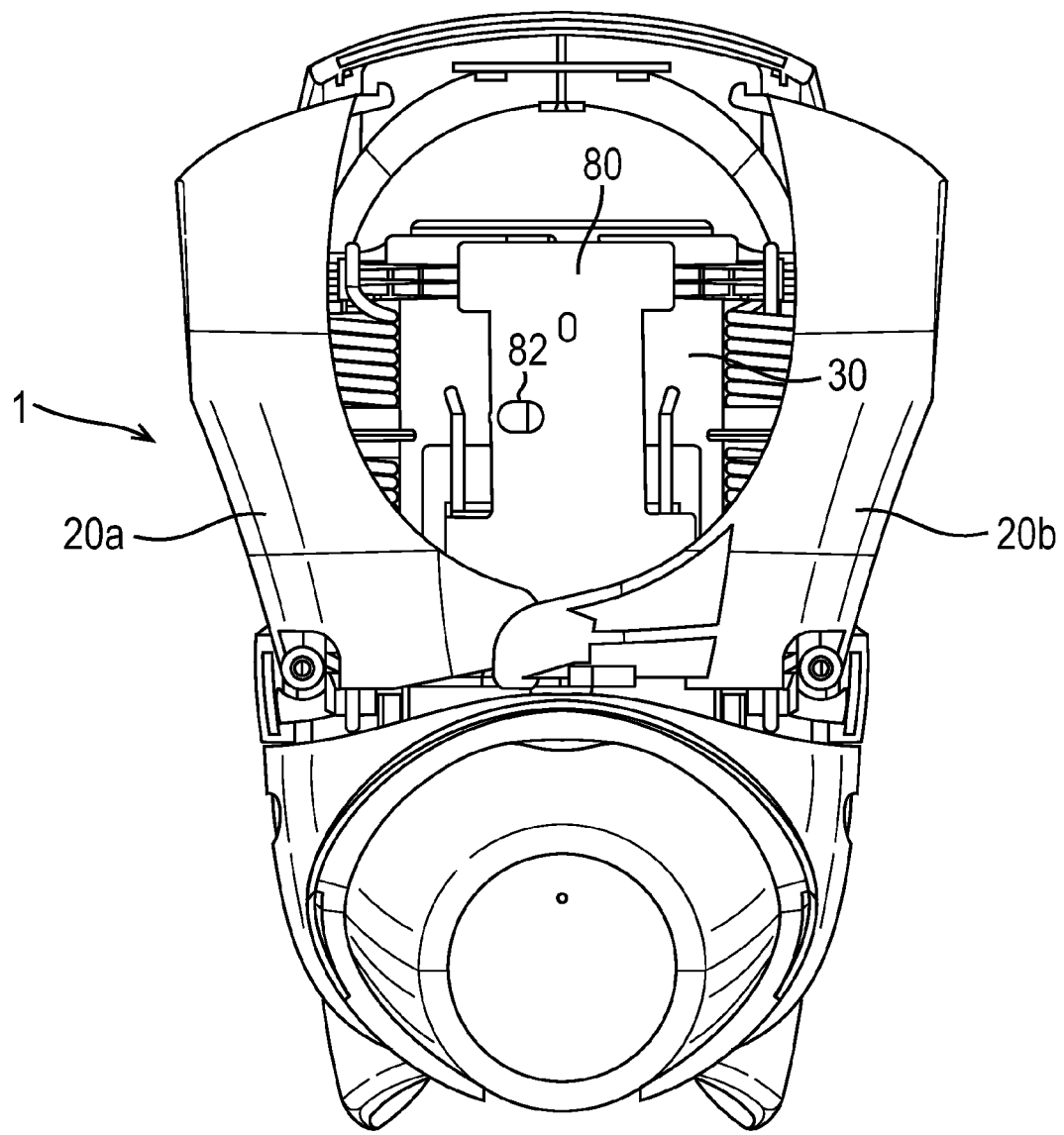

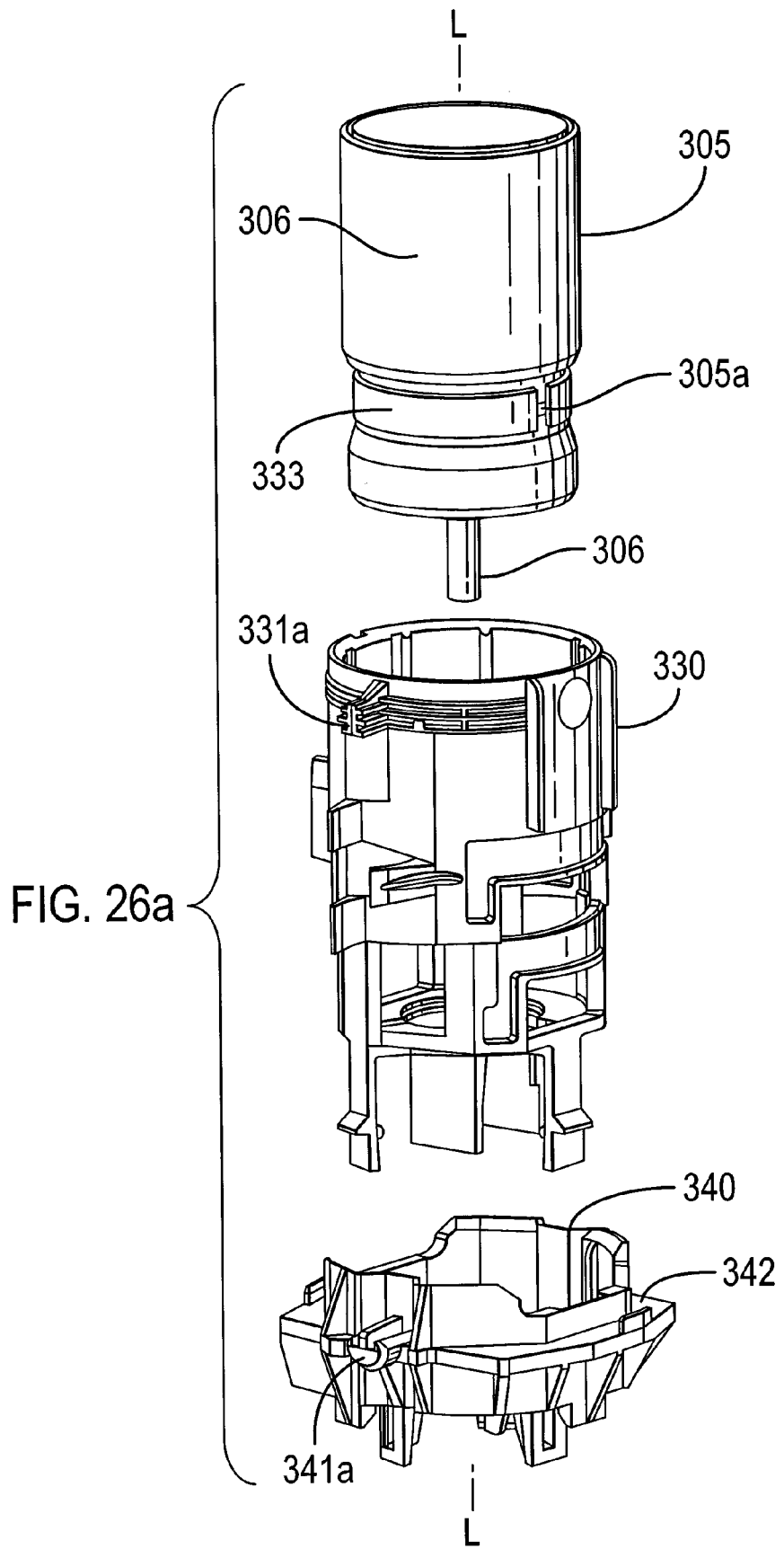

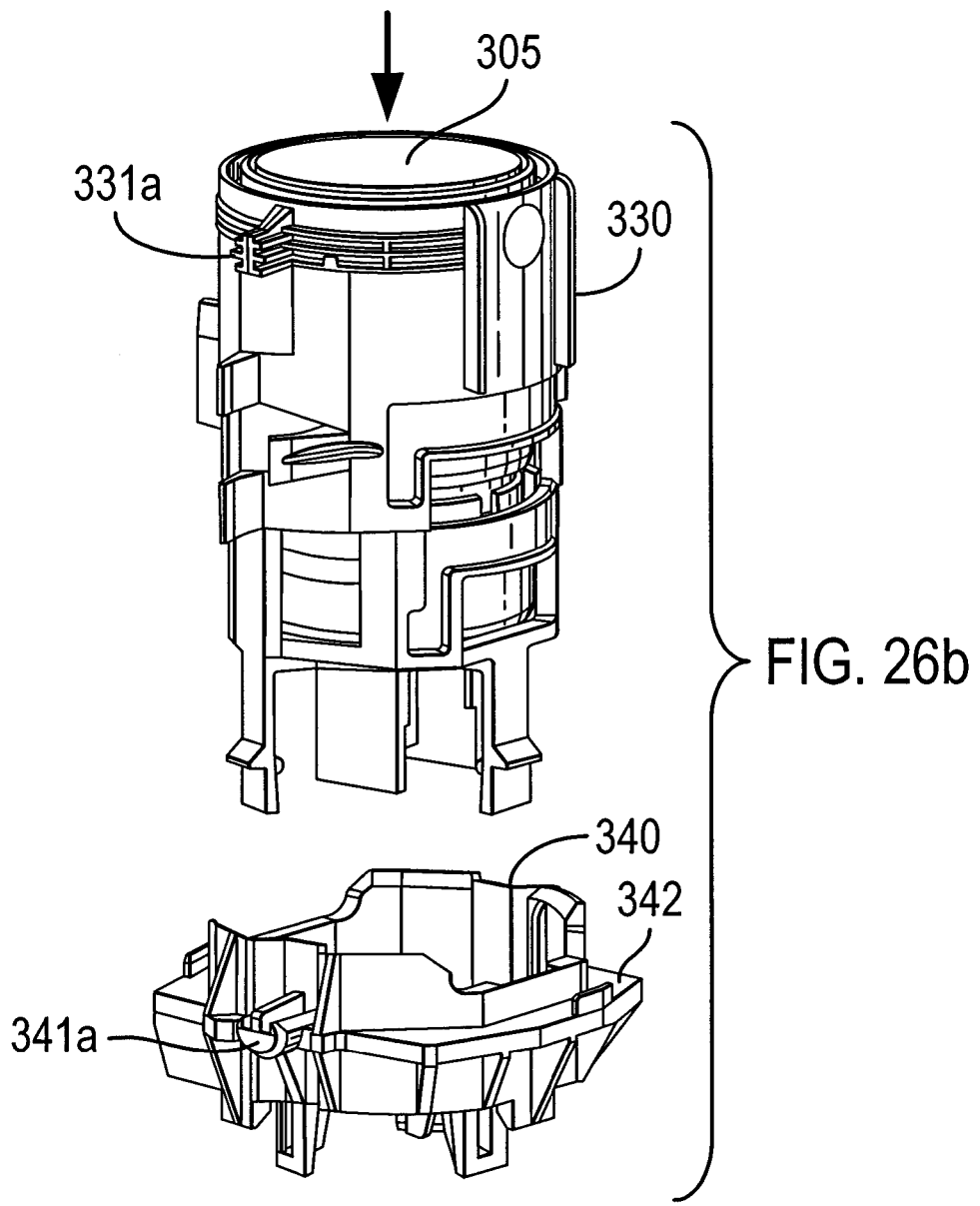

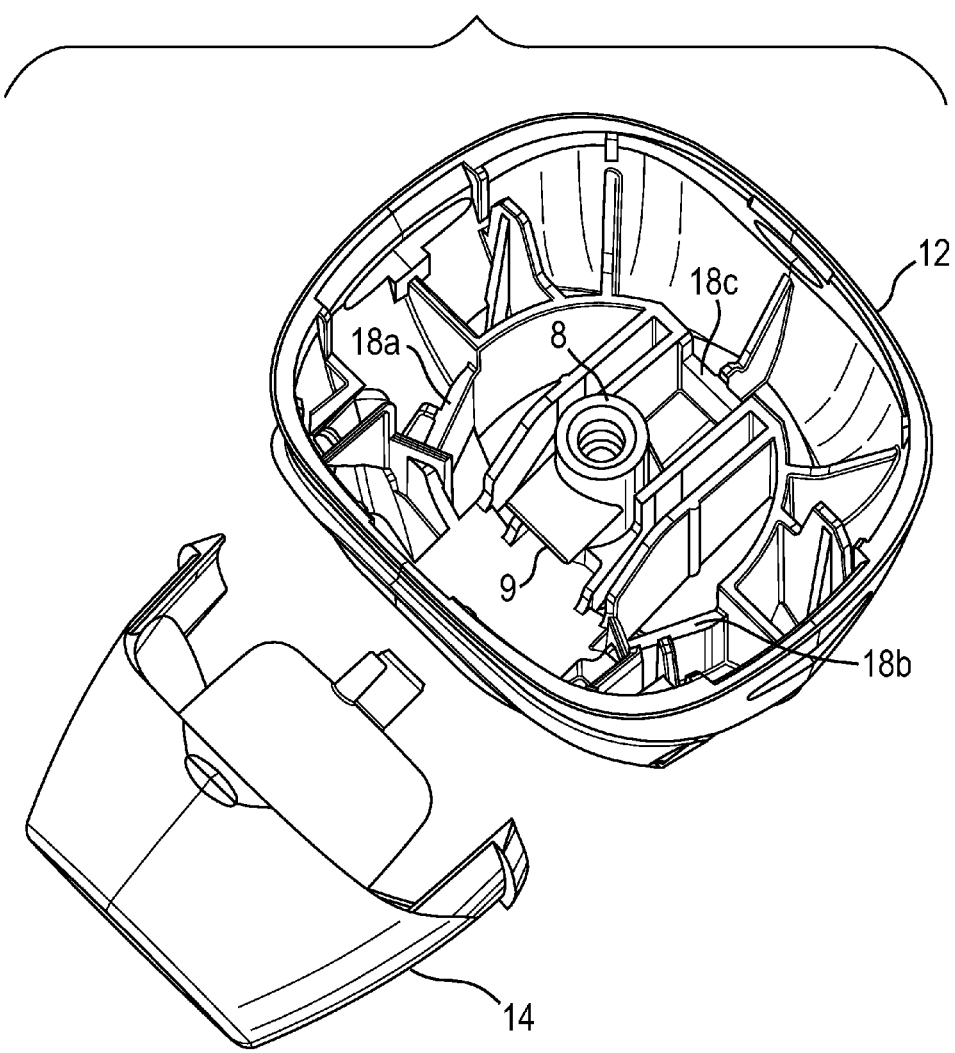

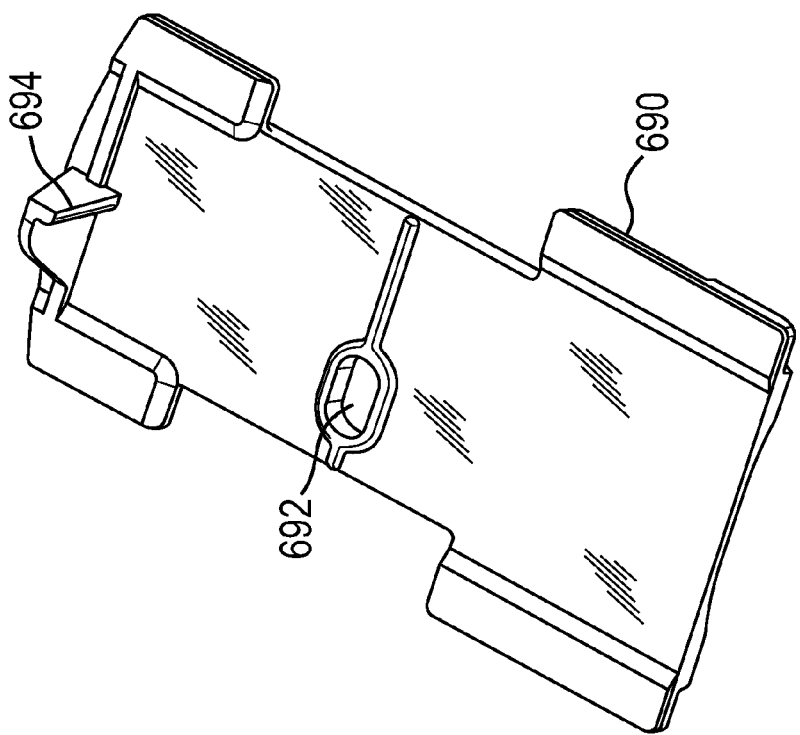
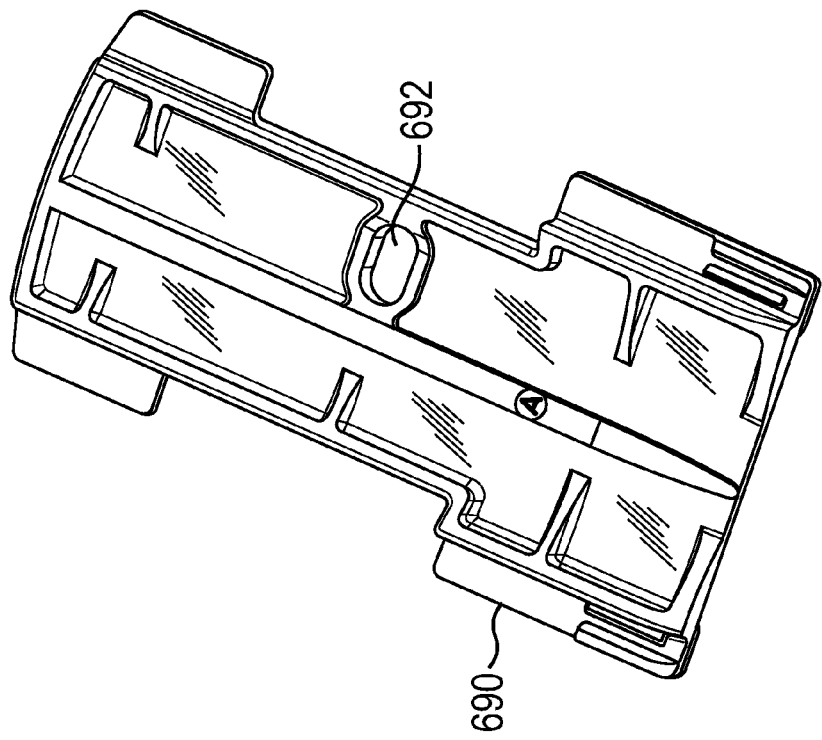

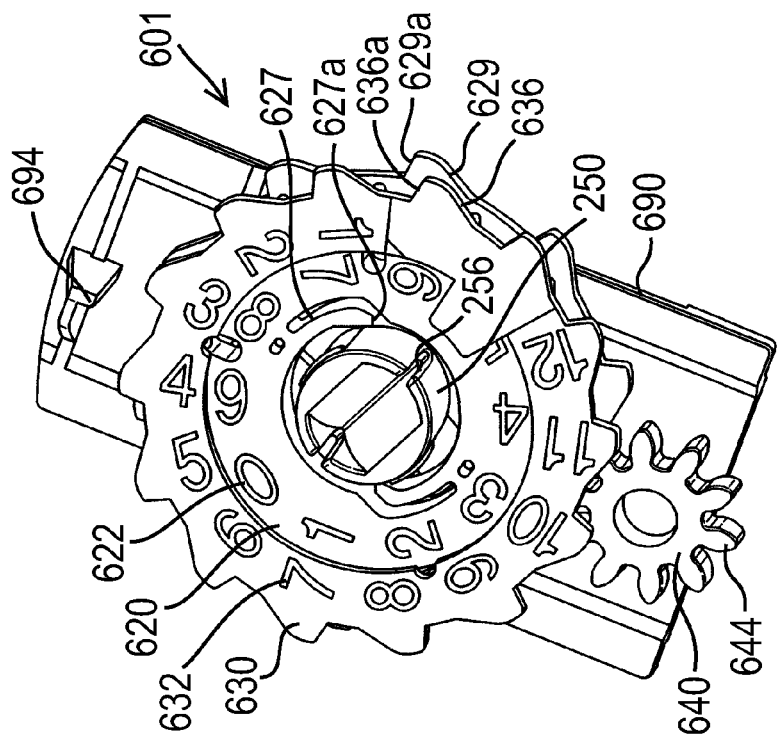
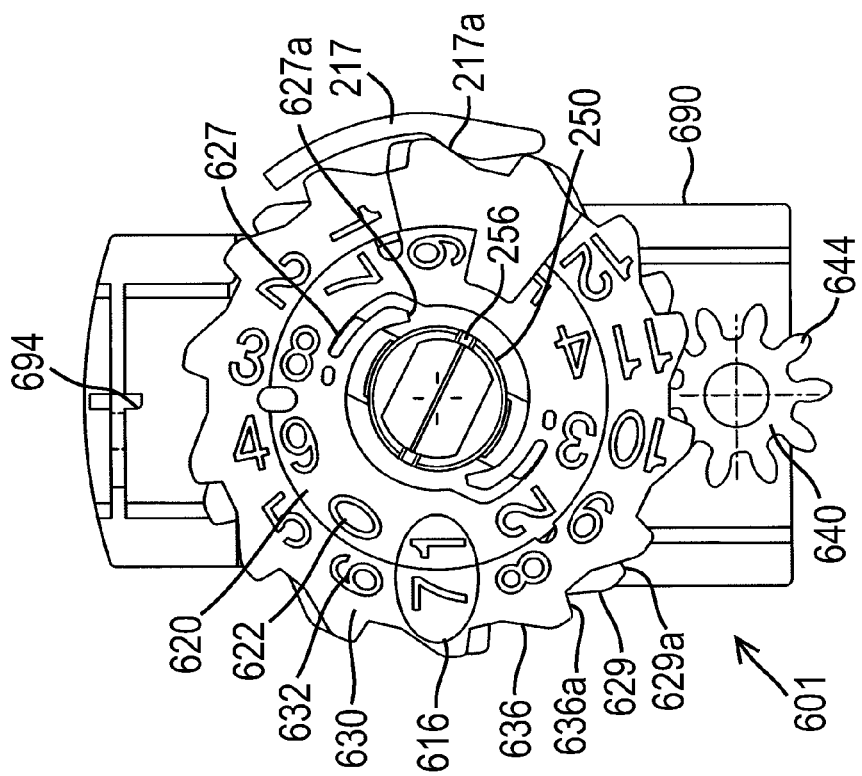

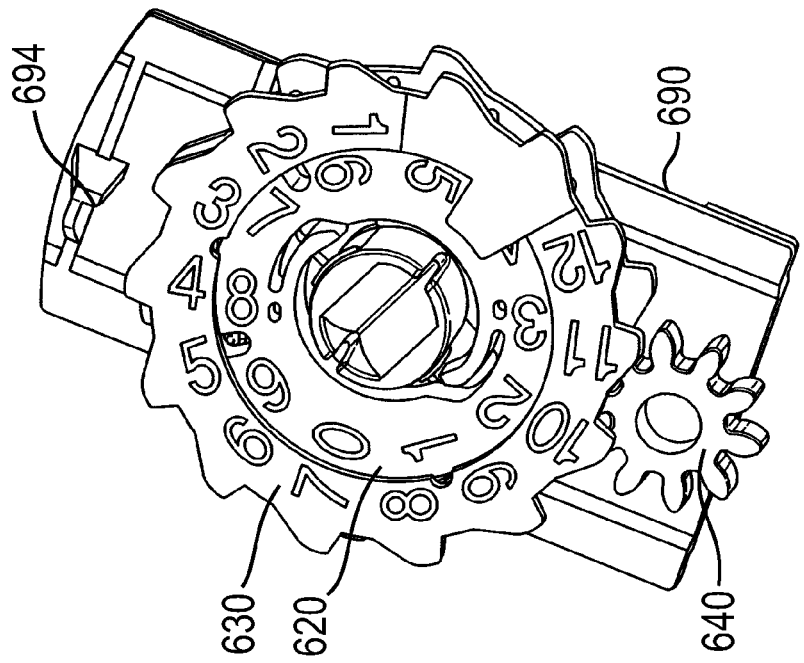
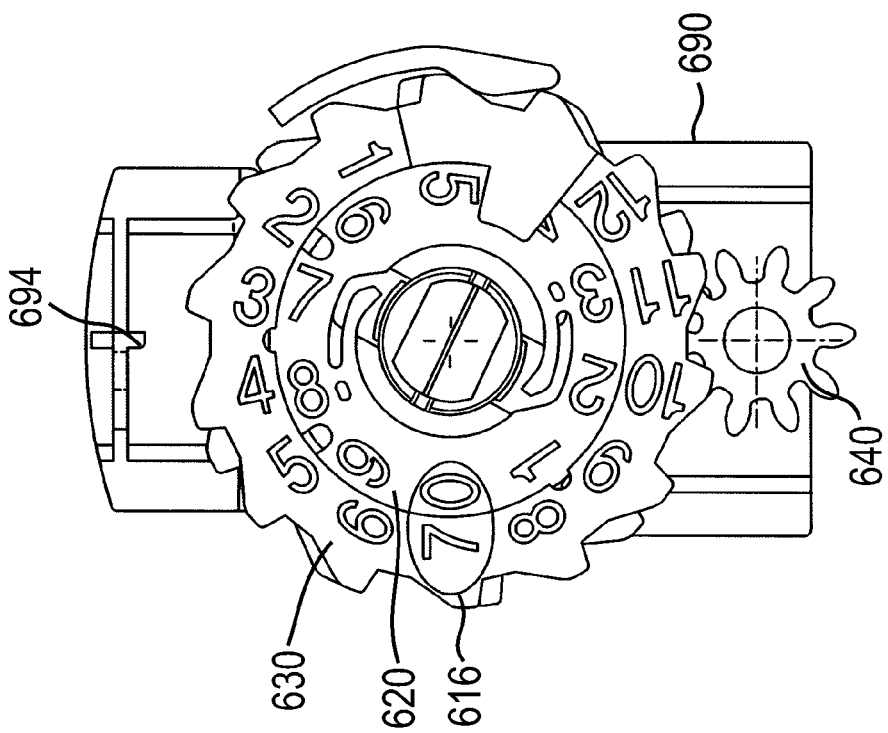

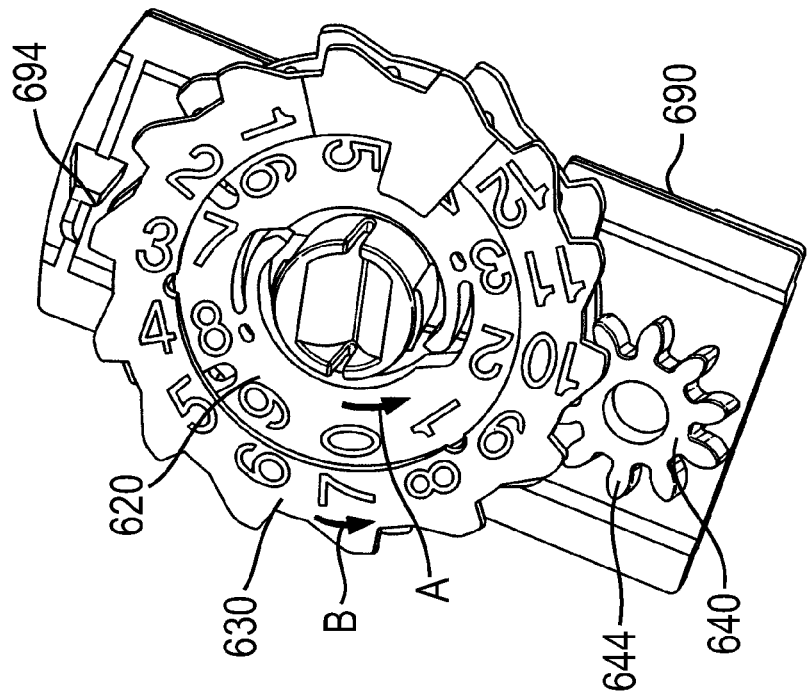
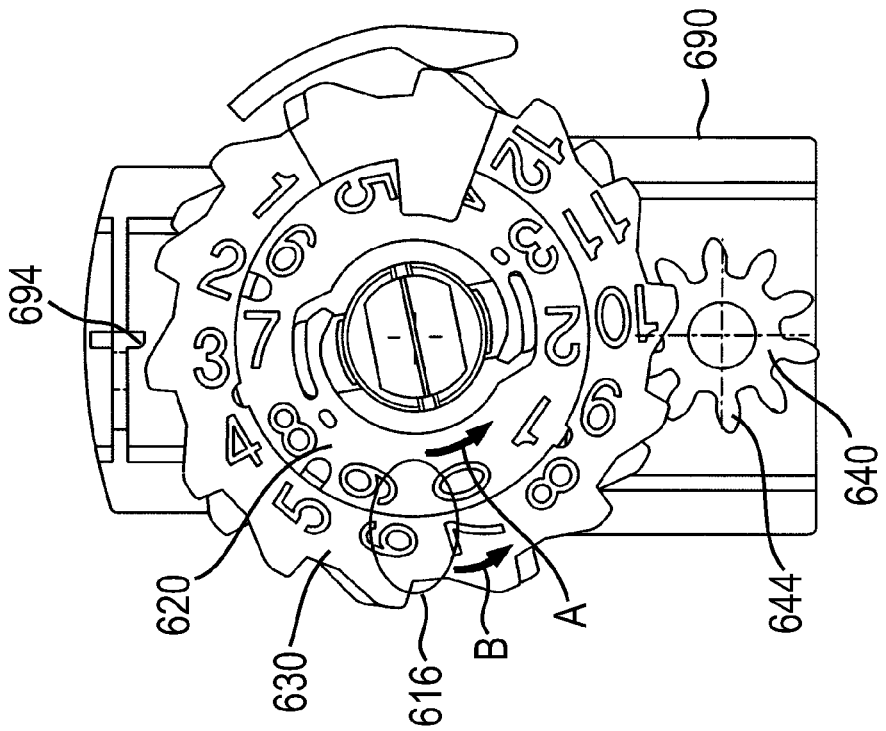

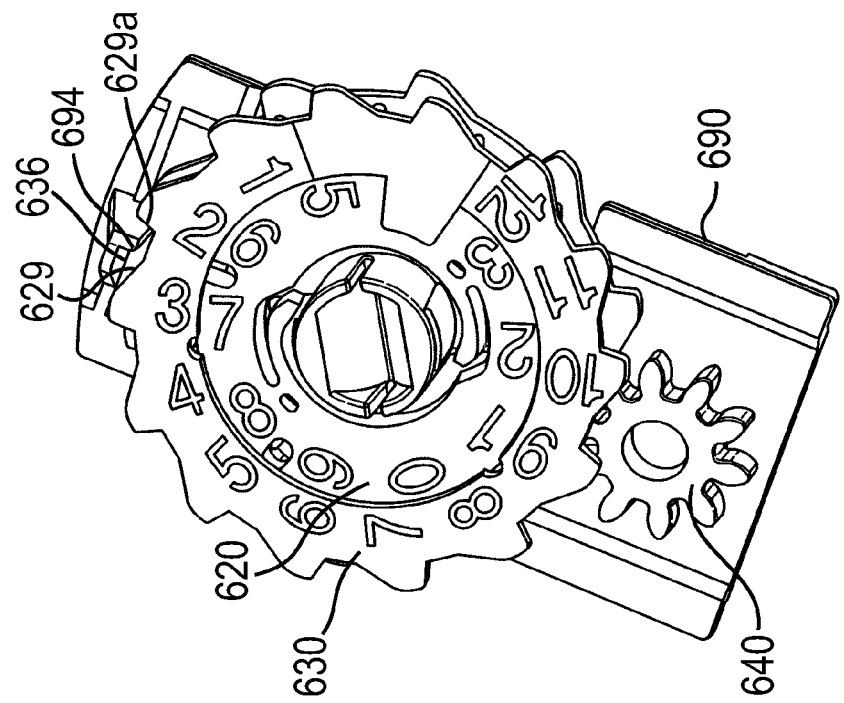
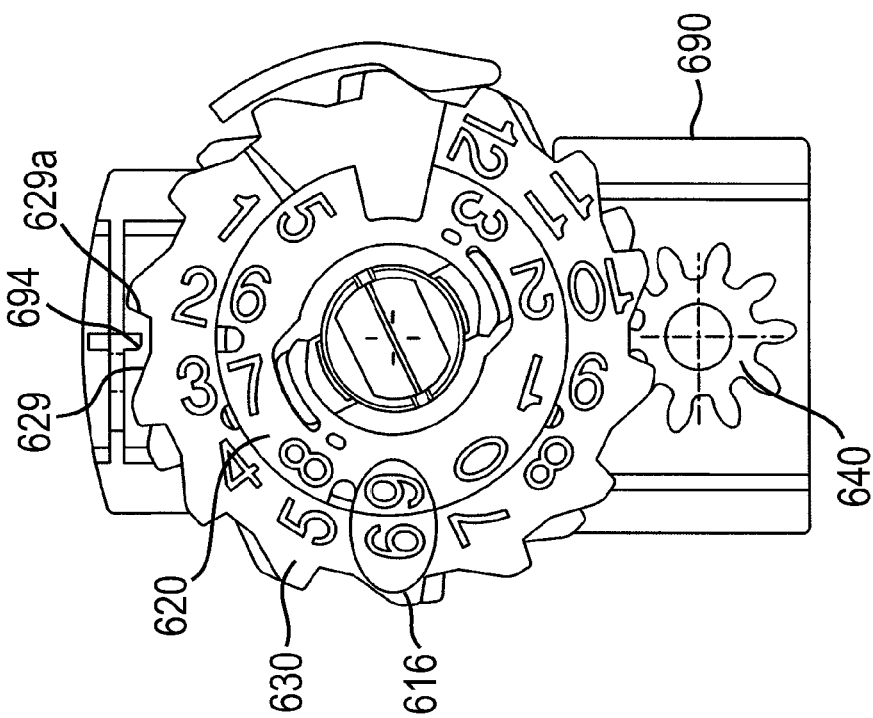

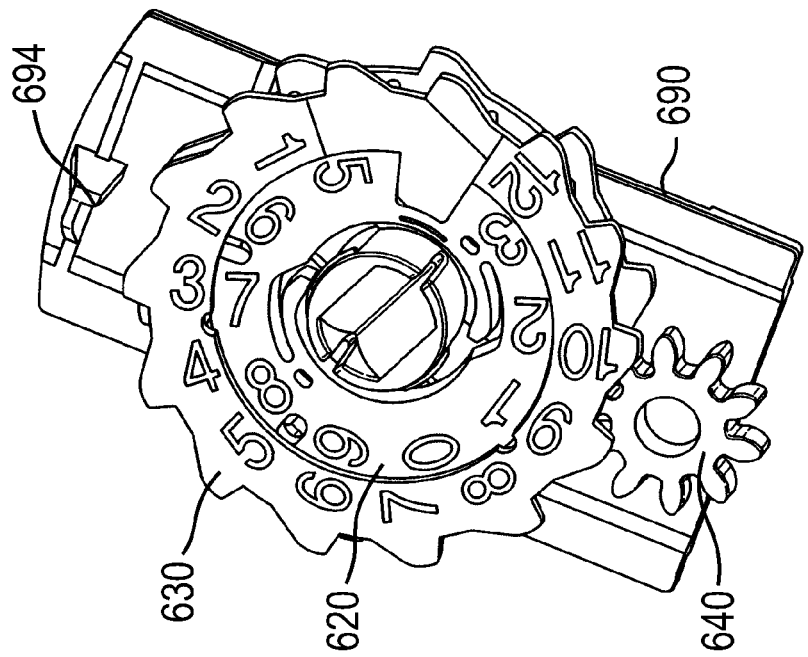

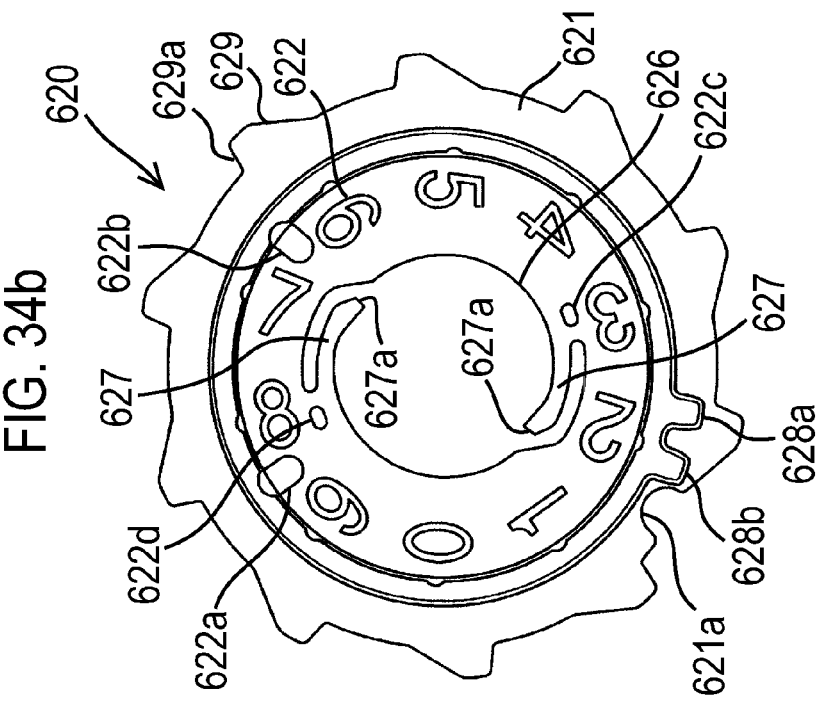
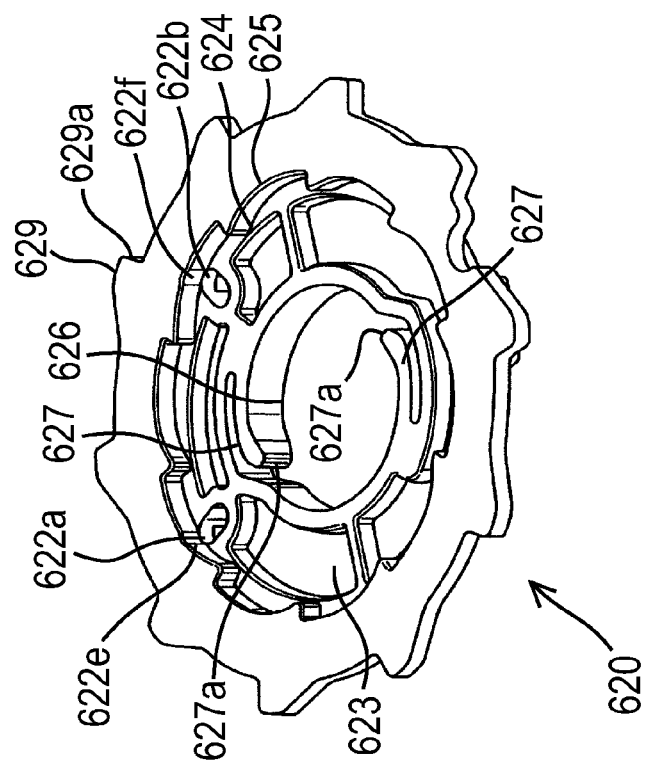
FIG. 34b
FIG. 34a

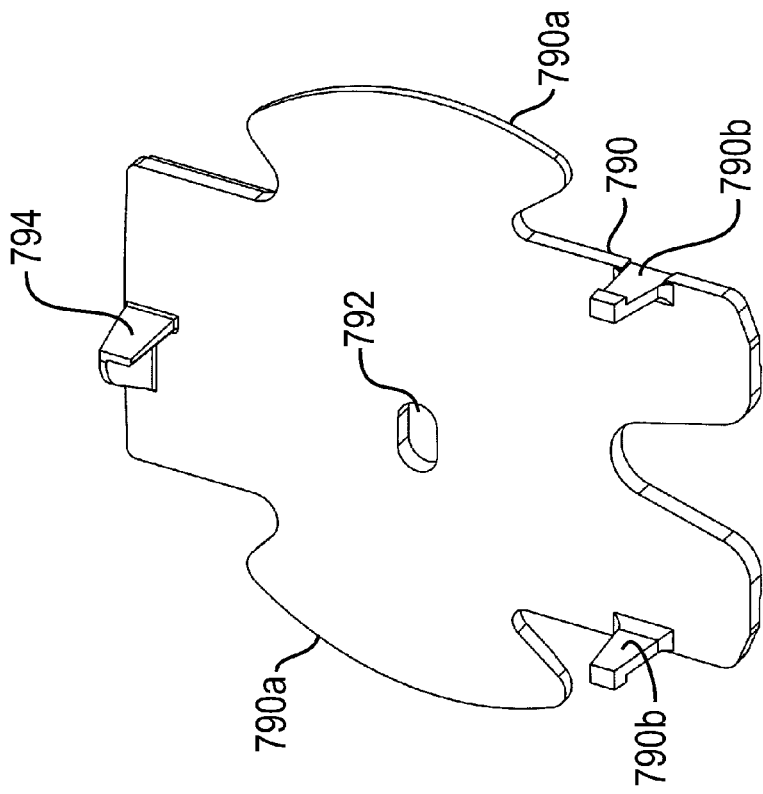
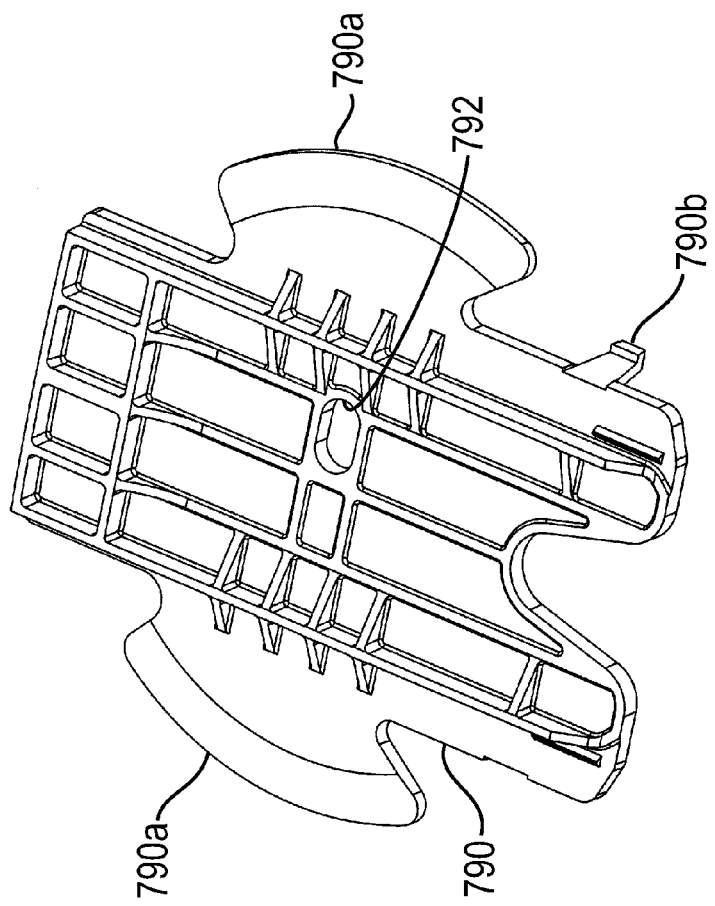

000
ACTUATION COUNTER

CROSS-REFERENCE TO RELATED APPLICATIONS

This application is filed pursuant to 35 U.S.C. 371 as a United States National Phase Application of International Application No. PCT/EP2009/051876 filed Feb. 17, 2009, which claims priority from U.S. Provisional Ser. No. 61/029,458 filed Feb. 18, 2008.

The present application claims priority from U.S. Provisional Application No. 61/029,458 filed 18 Feb. 2008, the entire content of which is incorporated herein by reference.

The disclosures of the following U.S. Provisional Applications are incorporated herein by reference in their entirety: U.S. Provisional Application Nos. 60/823,134, 60/823,139, 60/823,141, 60/823,143, 60/823,146, 60/823,151 and 60/823,154, all filed on 22 Aug. 2006; U.S. Provisional Application No. 60/894,537 filed on 13 Mar. 2007; and U.S. Provisional Application Nos. 60/956,947 and 60/956,950 filed on 21 Aug. 2007. The disclosures of the following International (PCT) Patent Applications and in particular the U.S. national phase applications designated therein, are all also incorporated herein by reference in their entirety: PCT Patent Application Nos. PCT/EP2007/058678 (WO-A-2008/023018); PCT/EP2007/058679 (WO-A-2008/023019); PCT/E P2007/058676 (WO-A-2008/023017); PCT/EP2007/058672 (WO-A-2008/023015); PCT/EP2007/058670 (WO-A-2008/023014); PCT/EP2007/058669 (WO-A-2008/023013) and PCT/US2007/076347 (WO-A-2008/024728), all filed on 21 Aug. 2007; PCT Patent Application No. PCT/EP2008/052967 (WO-A-2008/110584) filed 12 Mar. 2008; and PCT Patent Application No. PCT/EP2008/060861 filed 19 Aug. 2008.

The present invention relates to an actuation counter suitable for use with a drug dispenser and in particular to an actuation counter for use with a drug dispenser for delivering metered doses of aerosol or fluid drug formulation and adapted for use as an oral or nasal inhaler.

It is known to provide a drug dispenser, in which a drug dose is dispensed via a mouthpiece or nozzle upon the application of a force by a user to an actuating lever or similar actuating members. Typically, displacement of the actuating lever is arranged to transfer actuating force to a dispensing mechanism (e.g. a valve or pump) provided to a drug container, which results in dispensing of the drug dose. Such dispensers may be arranged to dispense a single dose or may alternatively be arranged with a reservoir containing several doses to be dispensed.

It is further desirable that such drug dispensers are provided with an actuation counter for counting the number of dispensed drug doses (i.e. the number of effective actuations of the drug dispenser). However, a 'false count' problem can arise where the actuation counter is able to register a count in response to all actuating movements rather than only those actuations that are sufficiently strong to result in dispensing of drug dose. In addition or alternatively, a 'count overrun' problem can also potentially occur in situations where the actuation counter may register more than a single count step (i.e. overrun) in response to a particularly extreme actuating movement. Such 'false counting' or 'count overrun' events are of particular concern where the patient is reliant on the count displayed by the actuation counter to provide a correct indication of how many drug doses have been dispensed from or alternatively that remain in the drug container.

It is an aim of an aspect of the present invention to provide an actuation counter to address the problem of 'count overrun', and to thereby provide a more reliable indication of actuation.

Applicant's U.S. patent application Ser. Nos. 10/597,551 and 12/282,652 (derived from PCT Application Nos. WO-A-2005/079727 and WO-A-2007/104964, respectively) describe various embodiments of an actuation counter for use with a medicament dispenser, the contents of each of which are incorporated herein by reference. The actuation counter comprises a first count wheel arranged to rotate about a first axis of rotation, the first count wheel including a set of primary drive teeth arranged annularly thereon for drivable rotation of the first count wheel about the first axis of rotation; and a second count wheel arranged to rotate about the same first axis of rotation. A kick wheel is arranged to rotate about a second axis of rotation offset from the first axis of rotation and provides for intermittent motion of the second count wheel.

According to a first aspect of the present invention there is provided an actuation counter according to claim 1 hereof.

The term 'actuation counter' is used to mean any device or apparatus that is suitable for counting, indicating or gauging that an actuation has taken place. The count, indication or gauge may in embodiments, be shown by reference to count indicia (e.g. alphanumeric (numerals and/or letters)). In other embodiments, other indicators are employed such as colour scales, line or block scales or other sensory or visual indicators of actuation.

In embodiments, the actuation counter is suitable for use with a drug dispenser device and includes a mechanism for registering and displaying dose count information to the patient. Suitably, that dose count information relates to the number of doses of drug delivered from or remaining in the dispenser device. The information may be delayed in digital or analogue form, typically using standard count indicia (e.g. '999' to '000' indicia count display). Embodiments involving either 'counting up' or 'counting down' in increments are envisaged.

The actuation counter may adopt any suitable form. The actuation counter is in embodiments sized and shaped for effective receipt by the housing of the drug dispenser. In embodiments, the actuation counter is supplied as an assembly for insertion into the drug dispenser. In embodiments, the actuation counter is shaped such that an inner wall of the housing of the drug dispenser may act as a mounting for some or all of the parts of the actuation counter.

The actuation counter includes a count member. The count member includes one or more drive receipt elements arranged thereon for receipt of drive from said one or more driver elements of a driver feature for drivable movement of the count member.

In embodiments, the count member is a first count member and the counter further comprises a second count member.

In embodiments, the first count member is a first count wheel and a second count member is a second count wheel. Each count wheel is suitably provided with count indicia thereon.

In embodiments, the first count wheel is arranged to rotate about a first axis of rotation, said first count wheel including one or more drive receipt elements arranged thereon for receipt of drive for drivable rotation of the first count wheel about said first axis of rotation.

In embodiments, the second count wheel is arranged to rotate about the first axis of rotation, said second count wheel including a set of teeth arranged annularly thereon.

In embodiments, a kick wheel is arranged to rotate about a second axis of rotation offset from the first axis of rotation, said kick wheel including a set of kick teeth arranged annularly thereon and in meshed relationship with the set of teeth of the second count wheel such that rotary motion of the kick wheel results in rotary motion of the second count wheel.

In embodiments, the first count wheel further includes at least one fixed index tooth arranged for intermittent meshing with the kick teeth of the kick wheel such that rotary motion of the kick wheel results from rotary motion of the first count wheel only when said intermittent meshing occurs.

In embodiments, the preferred actuation counter is configured and arranged so that said intermittent meshing is able to occur a plurality of times.

By 'arranged annularly' herein it means arranged about a common radius (i.e. defining an annular arrangement).

The first or second count wheel may for example, take the form of a disc or a ring.

In embodiments, the drive receipt elements can take any suitable form including one or more teeth and/or indents. In embodiments, the drive receipt elements of the first count wheel are arranged annularly, such as about an inner or outer circumferential wall of the first count wheel.

In one embodiment, the one or more drive receipt elements of the first count wheel comprise a set of teeth arranged annularly thereon for drivable rotation of the first count wheel about the first axis of rotation. Drive of the teeth is in embodiments provided by a driver element provided to another part of the drug dispenser. In embodiments, the driver element is provided to a container collar or a container or to a driver feature connecting to the container collar or container.

In another embodiment, the preferred actuation counter is provided with a ratchet, and the one or more drive receipt elements of the first count wheel comprise one or more ratchet drive receipt elements arranged thereon for receipt of drive from said ratchet to rotate the first count wheel about said first axis of rotation.

The ratchet is in embodiments a ratchet wheel arranged for rotation about an axis, which is preferably common with the first axis of rotation about which the first count wheel rotates. The ratchet is in embodiments provided with one or more ratchet drive elements such as one or more ratchet drive tongues.

In embodiments, the ratchet is itself provided with one or more drive receipt elements for receipt of drive that results in movement (e.g. rotation) of the ratchet. Such drive receipt elements can take any form including one or more teeth, protrusions and/or indents. Drive of the drive receipt elements of the ratchet is in embodiments provided by a driver element provided to another part of the drug dispenser. In embodiments, the driver element is provided to a container collar or a container or to a driver feature connecting to the container collar or container.

In a preferred embodiment, the first count wheel is provided with a circular cavity (e.g. hollowed out portion) sized and shaped for receipt of the ratchet wheel. The ratchet drive receipt elements are arranged about the inner circumferential wall (i.e. about the periphery) of the cavity for suitable ratchet drive interaction with the ratchet wheel.

Alternatively, the first count wheel takes the form of a ring that is sized and shaped for disposed receipt of the ratchet wheel. The ratchet drive receipt elements are arranged circumferentially about (i.e. about the periphery of) the inner wall of the ring for suitable ratchet drive interaction with the ratchet wheel.

In embodiments, the first and second wheels may be arranged to rotate in the same direction or in opposing directions (i.e. one clockwise and one anti-clockwise).

The second count wheel includes a set of teeth arranged annularly (e.g. circumferentially) thereon. The teeth are therefore arranged in annular fashion at or about the circumference of the second count wheel.

In embodiments, the second count wheel is arranged concentric to the first count wheel. In one embodiment, the second count wheel takes the form of a ring and the first count wheel (e.g. disc or ring shape) is sized and shaped for receipt within the ring. The diameter of the first count wheel is therefore typically slightly less than that of the inner diameter (i.e. the ring hole diameter) defined by the ring-shaped second count wheel.

In one embodiment, the first and second count wheels are arranged concentrically and at the same level (i.e. they share the same plane of rotation).

In another embodiment, the first and second count wheels are arranged concentrically and at different levels (i.e. with different planes of rotation).

In embodiments, the plane of rotation of the second counter wheel is slightly raised relative to that of the first counter wheel. In one embodiment, the second count wheel is provided with a protrusion that in use, extends over and above part of the first count wheel and that may therefore function to shutter off part of the first count wheel.

In embodiments, the actuation counter includes a wheel coupler that is arranged for movement. The wheel coupler includes a set of coupling teeth arranged thereon and in meshed relationship with the set of teeth of the second count wheel such that motion of the wheel coupler results in rotary motion of the second count wheel. The first count wheel further includes at least one fixed index tooth arranged for intermittent meshing (i.e. coupling) with the coupling teeth of the wheel coupler such that motion of the wheel coupler results from rotary motion of the first count wheel only when said intermittent meshing occurs.

In embodiments, the wheel coupler is arranged for rotary movement about an axis of rotation.

In embodiments, the wheel coupler is a kick wheel arranged to rotate about a second axis of rotation offset from the first axis of rotation. In embodiments, the kick wheel includes a set of kick teeth arranged (e.g. annularly) thereon and in meshed relationship with the set of teeth of the second count wheel such that rotary motion of the kick wheel results in rotary motion of the second count wheel, wherein the at least one fixed index tooth of the first count wheel is arranged for intermittent meshing with the kick teeth of the kick wheel such that rotary motion of the kick wheel results from rotary motion of the first count wheel only when said intermittent meshing occurs.

The kick teeth are preferably arranged in annular fashion at or about the circumference of the kick wheel.

As the kick wheel is rotated the meshing of the kick teeth thereof with the teeth of the second count wheel results in rotation of the second count wheel.

The first count wheel further includes at least one fixed index tooth arranged for intermittent meshing with the kick teeth of the kick wheel. That is to say, the at least one index tooth is fixed to the first count wheel and may be brought into meshed relationship with the kick teeth of the kick wheel on an intermittent basis.

Rotary motion of the kick wheel results from rotary motion of the first count wheel only when said intermittent meshing of the at least one index tooth with the kick teeth occurs. When meshing occurs, a contact ratio of 1 between the at least one index tooth and the kick teeth is preferred, although other part or whole integer contact ratios (e.g. 1.5, 2, 3 . . . ) may be used.

Typically, the at least one index tooth is fixed at a point at or about the circumference of the first count wheel. Rotation of the first count wheel is then arranged to bring the at least one index tooth into meshed relationship with the kick teeth of the kick wheel at a particular point of the rotary cycle of the first count wheel. It may be appreciated that in this case, meshing occurs once during each complete rotation of the first count wheel.

In embodiments, either one or both counter wheels interact with a reverse rotation (e.g. ratchet) mechanism to prevent reverse movement of the counter wheels.

In embodiments, some or all gear teeth of some or all of the toothed parts herein have flanged form to enable effective meshing together thereof.

The actuation counter is actuable in response to drivable rotation of the first count wheel by one or more driver elements provided to a driver feature, which driver feature is itself arranged to be drivably movable in response to an actuating movement (e.g. of a drug dispenser device).

In embodiments, each of the one or more driver elements has the form of a protrusion (e.g. tooth), an abutment, a rib, an indent or a slot provided to the driver feature and arranged for drive interaction with the one or more drive receipt elements of the first count wheel.

In embodiments, the driver feature is arranged for connection with a movable element of a drug dispenser device, wherein that movable element moves in response to actuation of the drug dispenser device. In embodiments, that movable element comprises a container or container collar of the drug dispenser device, and in embodiments the container collar or container is movable along a longitudinal axis of the drug dispenser device during actuation thereof.

In embodiments, the driver feature comprises or consists of a driver plate.

The driver feature is provided with one or more brake elements arranged to selectively interact (e.g. interfere) with the counter member to prevent overrun thereof when registering a count (e.g. of an actuation of a drug dispenser device).

In embodiments, the driver feature is provided with one or more brake elements arranged to selectively interact (e.g. interfere) with a first counter wheel and/or a second counter wheel to prevent overrun thereof when registering a count of an actuation (e.g. of a drug dispenser device). In essence, the one or brake elements are arranged such as to prevent the first and/or second counter wheels overrunning (i.e. rotating too much) such that any one actuation registers only a single counting step.

In embodiments, the one or more brake elements are arranged to selectively interact with the first counter wheel and/or the second counter wheel to allow only a pre-determined degree of rotation thereof during an actuation counting operation. It will be appreciated that the pre-determined degree of rotation will be selected to ensure that count overrun is prevented, and also that the pre-determined degree of rotation relating to the first and second counter wheels may either correspond or be different dependent upon the relative spacing of count indicia thereon.

In embodiments, the one or more brake elements are initially spaced from the first counter wheel and/or the second counter wheel and brought into proximity for selective interaction therewith in response to drivable movement of the driver feature. In embodiments, the one or more brake elements are brought into such proximity for selective interaction at a point in the actuation counting operation corresponding to when a single count has been registered (i.e. after the first and/or the second count wheels have been rotated sufficiently on that a single count is registered).

In embodiments, each of the one or more brake elements has the form of a protrusion (e.g. tooth), an abutment, a rib, an indent or a slot provided to the driver feature and arranged for braking interaction with the first counter wheel and/or the second counter wheel.

In embodiments, the one or more brake elements are arranged for selective interaction with one or more brake receipt elements of the first count wheel and/or the second count wheel. In embodiments, each of the one or more brake receipt elements has the form of a protrusion (e.g. tooth), an abutment, an indent, a rib or a slot provided to the first count wheel and/or the second count wheel and arranged for braking interaction with the one or more brake elements of the driver feature.

In embodiments, the one or more brake elements are arranged annularly e.g. circumferentially about (i.e. about the periphery of) the first and/or the second count wheel. Where the first and/or the second count wheel have the form of a ring such arrangement of one or more brake elements is circumferentially about the ring form thereof.

In embodiments, the actuation counter includes a counter housing, which houses some or all of the other elements of the actuation counter. In embodiments, the counter housing is defined at least in part by the housing of a drug dispenser for use with the actuation counter herein.

In embodiments, the counter housing is shaped to define the first axis of rotation and the second axis of rotation. In embodiments, the first count wheel mounts to the counter housing for rotation about the first axis of rotation and the kick wheel mounts to the counter housing for rotation about the second axis of rotation.

In embodiments, the counter housing includes a viewing window through which the count may be viewed. In embodiments, the counter housing includes a bezel and/or lens cover for the count wheels and through which indicia of the count wheels are generally visible.

In one embodiment, a shutter is provided to close off the viewing window at a predetermined point in the actuation counter operation, particularly at the 'end of life' of the drug product, which typically corresponds to the point at which all doses in the normal (prescribed) delivery cycle have been provided. In embodiments, the shutter may be provided as a separate element of the actuation counter or drug dispenser or be formed as an integral part of the second counter wheel, as described hereinbefore.

In embodiments, the first and second count wheels are adapted in use to rotate in the same sense about the first axis.

In embodiments, the drug dispenser for use with the actuation counter has a display region through which the first and second count wheels are rotatable and a shutter which is movable to a shuttering position in which it shutters the display region. In embodiments, the actuation counter is so configured and arranged that the shutter is only movable to the shuttering position when the first and second count wheels are in predetermined angular positions about the first axis. In embodiments, the actuation counter is configured and arranged so that the shutter is only able to be moved to the shuttering position when the first count wheel has rotated through a plurality of revolutions about the first axis. In embodiments, the actuation counter is configured and arranged such that the shutter moves to its shuttering position in response to movement of at least one of the count wheels.

In embodiments, the shutter is moved to its shuttering position by the at least one count wheel. In embodiments the shutter is carried to the shuttering position by the at least one count wheel. In embodiments, the at least one count wheel is the second count wheel. In embodiments, the at least one count wheel and the shutter have cooperating parts through which, in use, the at least one count wheel moves the shutter to its shuttering position.

In embodiments, the actuation counter is configured and arranged to display a count sequence with the count wheels and to cause the shutter to move to its shuttering position at the end of the count sequence.

In embodiments, the shutter is comprised in one of the count wheels. In embodiments, the count wheel is integrally formed with the shutter. In embodiments, the shutter overlies the other count wheel. In embodiments, the shutter is comprised in the second count wheel.

In embodiments, the actuation counter is configured and arranged to sequence from a count mode of operation, in which the first count wheel is able to drive rotation of the second count wheel through the kick wheel, to a non-count mode of operation, in which the first count wheel is unable to drive rotation of the second count wheel through the kick wheel. In embodiments, the actuation counter is arranged to sequence from the count mode to the non-count mode when the first count wheel has completed a predetermined number of revolutions about the first axis. In embodiments, the actuation counter is adapted to sequence from the count mode to the non-count mode when the second count wheel is disposed in a predetermined angular orientation about the first axis.

In embodiments, the actuation counter is configured and arranged such that in the non-count mode meshing of the kick teeth with the at least one index tooth and/or the second count wheel teeth is unable to occur. In embodiments, a gap is provided in the set of kick teeth or the second count wheel teeth to disable meshing in the non-count mode.

In an embodiment of the invention, the actuation counter is a dose counter for counting the number of doses of drug dispensed from the drug dispenser device and comprises first and second count wheels which are concentrically arranged for rotation on a common axis of rotation, each count wheel having count indicia thereon; a display region positioned for the count indicia of each count wheel to register with and display the count of the counter; a ratchet for incrementally rotating the first count wheel in a predetermined sense to change the count indicia thereof registering with the display region; and a mechanism adapted to intermittently transmit the incremental rotation of the first count wheel into an incremental rotation of the second count wheel in a predetermined sense to change the count indicia thereof registering with the display region.

The actuation counter herein is suitable for use with a drug dispenser device. The drug dispenser device typically comprises a housing. The housing may have any suitable form but is in embodiments sized and shaped for ready accommodation by the hand of a patient. In particular, the housing is sized and shaped to enable one-handed operation of the dispenser device.

In embodiments, extending from the housing, there is provided an outlet for insertion into a body cavity of a patient. Where the patient body cavity is the mouth of a patient, the outlet is generally shaped to define a mouthpiece. Where the patient body cavity is the nose of a patient, the outlet is generally shaped in nozzle form for receipt by a nostril of the patient. The outlet may be provided with a removeable protective cover such as a mouthpiece cover or nozzle cover.

In embodiments, provided to the housing and moveable with respect thereto, there is a drug discharge device. The drug discharge device has a longitudinal axis and comprises a container for storing a drug formulation to be dispensed. In embodiments, the container adopts a generally cylindrical form and the longitudinal axis is defined by the central axis of the cylinder. The container is in embodiments arranged to have a neck at one end.

The container is typically provided with a discharge mechanism, which communicates with a discharge channel extending from the container for discharge of the drug formulation to the outlet of the dispenser device. In embodiments, the discharge channel extends out from a neck of the container.

Typically, the discharge mechanism is provided with a spring mechanism (or other biasing mechanism) that provides a degree of bias that must be overcome in order to allow discharge of drug from the discharge mechanism. Typically, that spring mechanism also acts as a return mechanism to assist with return of the discharge mechanism to its rest state after firing thereof.

In embodiments, the discharge channel is received by a cavity or passage provided to a part (e.g. block form) of the housing, which cavity or passage enables communication with the outlet for dispensing of discharged drug to a patient.

In one embodiment, where the discharge channel is the valve stem of a valved aerosol canister, the valve stem is received within a stem block provided to the housing, which stem block includes a passage which acts such as to channel discharged aerosolized drug from the valve stem to the outlet.

In another embodiment, where the discharge channel is the discharge tube of a fluid pump discharge device, the discharge tube is received within a discharge tube block provided to the housing, which discharge tube block includes a passage which acts such as to guide discharged fluid drug from the discharge tube to the outlet.

In one embodiment, the drug discharge device is suitable for dispensing aerosolized drug and thus, generally comprises an aerosol canister provided with a discharge valve of the type well-known for use in metered dose inhaler (MDI) type drug dispensers. The canister is generally formed of metal (e.g. aluminium). The valve generally includes a return spring such that once the valve has been fired it is returned to an 'at rest' position ready for subsequent firing thereof.

In a metered dose inhaler (MDI) the discharge device is for dispensing drug in aerosol form, wherein the drug is comprised in an aerosol container suitable for containing a propellant-based aerosol drug formulation. The aerosol container is typically provided with a metering valve, for example a slide valve, which acts as the discharge mechanism for release of the aerosol form drug formulation to the patient. The aerosol container is generally designed to deliver a predetermined dose of drug upon each actuation by means of the valve, which can be opened by compressing the valved aerosol container, for instance by depressing the valve while the container is held stationary or by depressing the container while the valve is held stationary.

Where the drug container is an aerosol container, the valve typically comprises a valve body having an inlet port through which a drug aerosol formulation may enter said valve body, an outlet port through which the aerosol may exit the valve body and an open/close mechanism by means of which flow through said outlet port is controllable.

The valve may be a slide valve wherein the open/close mechanism comprises a sealing ring and receivable by the sealing ring a valve stem having a dispensing passage, the valve stem being slidably movable within the ring from a valve-closed to a valve-open position in which the interior of the valve body is in communication with the exterior of the valve body via the dispensing passage.

Typically, the valve is a metering valve. The metering volumes are typically from 10 to 100 µl, such as 25 µl, 50 µl or 63 µl. In embodiments, the valve body defines a metering chamber for metering an amount of drug formulation and an open/close mechanism by means of which the flow through the inlet port to the metering chamber is controllable. Preferably, the valve body has a sampling chamber in communication with the metering chamber via a second inlet port, said inlet port being controllable by means of an open/close mechanism thereby regulating the flow of drug formulation into the metering chamber.

The valve may also comprise a 'free flow aerosol valve' having a chamber and a valve stem extending into the chamber and movable relative to the chamber between dispensing and non-dispensing positions. The valve stem has a configuration and the chamber has an internal configuration such that a metered volume is defined therebetween and such that during movement between its non-dispensing and dispensing positions the valve stem sequentially: (i) allows free flow of aerosol formulation into the chamber, (ii) defines a closed metered volume for pressurized aerosol formulation between the external surface of the valve stem and internal surface of the chamber, and (iii) moves with the closed metered volume within the chamber without decreasing the volume of the closed metered volume until the metered volume communicates with an outlet passage thereby allowing dispensing of the metered volume of pressurized aerosol formulation.

In embodiments any of the inner parts of the valve (e.g. those which in use, will contact the drug formulation) are coated with material (e.g. fluoropolymer material) that reduces the tendency of drug to adhere thereto. Suitable fluoropolymer materials include polytetrafluoroethylene (PTFE) and fluorinated ethylene-propylene co-polymer (FEP). Any movable parts may also have coatings applied thereto, which enhance their desired movement characteristics. Frictional coatings may therefore be applied to enhance frictional contact and lubricants used to reduce frictional contact as necessary.

In another embodiment, the drug discharge device is a fluid discharge device suitable for dispensing of fluid drug formulation (e.g. non-pressurised/propellant-free) and thus, generally comprises a fluid container provided with a compression pump. Such pumped discharge devices are most commonly used in dispensers for dispensing fluid form drug for nasal delivery.

A suitable fluid discharge device comprises a container for storing a fluid to be dispensed having a neck at one end, a compression pump having a suction inlet located within the container and a discharge tube extending out from the neck of the container for transferring said fluid from the pump. The pump generally includes a return spring such that once the pump has been fired it is returned to an 'at rest' position ready for subsequent firing thereof.

A suitable pre-compression pump would be a VP3, VP7 or modifications, model manufactured by Valois SA. Typically, such pre-compression pumps are typically used with a bottle (glass or plastic) container capable of holding 8-50 ml of a formulation. Each spray will typically deliver 50-100 µl of such a formulation and the device is therefore capable of providing at least 100 metered doses.

The container collar is in embodiments in essentially fixed relationship with (i.e. it fixes to) the drug discharge device, e.g. the container. In embodiments, the container collar engages (e.g. in essentially fixed relationship) with a neck of the container.

The container collar may engage with the drug discharge device, e.g. (the neck of) the container, by any suitable permanent or temporary engagement including a snap-fit engagement mechanism. Preferably, as in the illustrated embodiments hereinafter, the container collar is permanently connected to the container through use of a split-ring collar as described in U.S. patent application Ser. Nos. 10/110,611 (WO-A-01/28887) and US-A-2006/0082039.

There is further provided connecting (via a biasing mechanism as later described) to the container collar and moveable with respect thereto along the longitudinal axis of the drug discharge device, a transfer element. The transfer element may have any suitable form but preferably comprises an extension collar that is sized and shaped for receipt by the container and arranged in suitable fashion relative to the container collar. In one embodiment, the extension collar is sized and shaped for receipt around (i.e. external to) the container collar.

The transfer element includes an actuating portion. The actuating portion is shaped for interaction with the at least one finger operable member, and may take any form that facilitates and accommodates that interaction including abutment (e.g. flange or shelf), rack and pinion gear and indent forms. In embodiments, the actuating portion defines an abutment surface.

The housing is provided with the at least one finger operable member. Preferably, the at least one finger operable member is moveable transversely with respect to the longitudinal axis of the drug discharge device. In alternative embodiments, the at least one finger operable member may therefore directly contact the actuating portion of the transfer element or be coupled thereto to enable the necessary transfer of force.

The at least one finger operable member is in embodiments shaped for direct interaction with the actuating portion, and may take any form that facilitates and accommodates that direct interaction including abutment and indent forms. In embodiments, the at least one finger operable member defines a bearing surface arranged for interaction with the actuating portion of the transfer element.

The term at least one finger operable member is meant to encompass such members operable by action of the finger or thumb, or combinations thereof of a typical user (e.g. an adult or child patient).

In embodiments, the at least one finger operable member is arranged to apply mechanical advantage. That is to say, the at least one finger operable member applies mechanical advantage to the user force to adjust (generally, to enhance or smooth) the force experienced by the transfer element. The mechanical advantage may in one embodiment, be provided in either a uniform manner such as by a constant mechanical advantage enhancement, for example by a ratio of from 1.5:1 to 10:1 (enhanced force:initial force), more typically from 2:1 to 5:1. In another embodiment, the mechanical advantage is applied in a non-constant manner such as progressive increase or progressive decrease of mechanical advantage over the applied force cycle. The exact profile of mechanical advantage variation may be readily determined by reference to the desired dispensing performance of the dispenser device.

In embodiments, the at least one finger operable member has a form, which naturally gives rise to mechanical advantage such as a lever.

In embodiments, the at least one finger operable member comprises of at least one lever pivotally connected to part of the housing and arranged to transfer force to the transfer element (e.g. acting directly thereupon) so as to urge the transfer element in the first direction when the or each lever is moved by a user.

In one preferred embodiment, there are two opposing levers, each of which pivotally connect to part of the housing and may be arranged to act upon the transfer element so as to urge the transfer element in the first direction when the two levers are squeezed together by a user.

In one embodiment, the movement of the two opposing levers is coupled, which coupling acts to wholly or partly compensate for uneven force being applied in use, by a patient to one lever as applied to the other lever. Any suitable coupling mechanism may be employed. In one embodiment, the two opposing levers are provided with meshing teeth, which teeth are arranged to mesh together thereby providing a coupling action.

In embodiments, the or each lever is pivotally supported at a lower end within the housing. By 'at a lower end within the housing' it is generally meant at that end of the housing which in normal use of the drug dispenser device by a patient is lowermost.

The use of a lower end pivoted lever configuration has the advantage that a long lever can be used thereby maximising the mechanical ratio between the input force and the force applied to actuate the transfer element. In addition the use of a lever pivotally supported at its lower end is ergonomically more efficient than using a lever pivotally supported at an upper end due to the fact that a user will normally grasp the dispenser device with their thumb positioned close to the end of the lever. With a lever pivotally supported at an upper end (again, relative to the normal 'in use' configuration) the location of a patient's thumb is close to the position about which the lever pivots and hence the maximum leverage is not obtained.

Optionally, there is provided to the drug dispenser device a locking mechanism for reversibly locking/unlocking the movement of the at least one finger operable member and/or the container collar. The purpose of the locking mechanism is to prevent unintended movement of the at least one finger operable member and/or container collar and hence, to prevent unintended actuation of the dispenser device.

In embodiments, the locking mechanism comprises a locking element comprising any suitable limb, protrusion, or abutment which acts such as to interfere with the unintended movement of the at least one finger operable member and/or container collar. Such unintended movement may for example, arise as a result of patient misuse of the dispenser device or during transport of the device (e.g. when carried in the pocket or bag of a patient).

In one embodiment, the locking mechanism is provided to a removeable cover for the outlet (e.g. mouthpiece or nozzle cover). Thus, in use the patient would remove the outlet cover thereby simultaneously revealing the outlet and unlocking the locking mechanism. Conversely, after the use the outlet cover is replaced to again lock the at least one finger operable member and/or container collar. In alternative embodiments, the locking mechanism may comprise an integral part of the removeable cover or by provided as a fixed add-on thereto or be provided as a moveable (e.g. rotatable or translatable) add-on thereto.

In one embodiment, the locking mechanism is arranged to prevent unintended movement of the container collar and hence, firing of the discharge mechanism, but does not impede the movement of the at least one finger operable member and/or of the transfer element. Thus, when the container collar is in its locked state (i.e. locking mechanism is performing its locking function) the at least one finger operable member (e.g. lever) may still be moved and that movement transfer energy via the biasing mechanism to move the transfer element, but all movement of the container collar is prevented. This form of locking arrangement has the advantage that unintended force applied to the finger-operable (e.g. levers) allows for travel thereof without damage thereto or to the device as a whole, but without any actuation of the dispenser device (e.g. by firing of the discharge mechanism).

In one embodiment, the container collar is provided at its underside with one or more (e.g. two) downward protrusions and the mouthpiece is provided with a locking mechanism in the form of one or more interference elements. In embodiments, the interference element(s) is P-shaped and joined to the mouthpiece by means of a suitable hinge (e.g. living hinge) about which the interference element(s) may rotate. In an embodiment, there are two interference elements joined together by a bridge element. When, the mouthpiece engages with the body of the dispenser device (i.e. in the mouthpiece-closed position) the interference element(s) abuts the downward protrusion(s) to thereby prevent (i.e. lock) any downward movement of the container collar. Unintended movement of the container collar and hence, unintended actuation of the dispenser device (i.e. firing of the discharge mechanism) is hence prevented. In embodiments, however the at least one finger operable member and transfer element are free to move, even when the container collar is in its locked state.

One particular locking mechanism, in which one or more rotatable interference elements are provided to the mouthpiece, is described in Applicant's co-pending U.S. patent application Ser. No. 12/066,048, derived from PCT Patent Application No. WO-A-2007/028992 which claims priority from UK Patent Application No. 0518355, each of these Applications being hereby incorporated herein by reference.

There may further be provided a biasing mechanism which acts such as connect the container collar to the transfer element. The biasing mechanism acts to store biasing energy on moving the transfer element relative to the container collar along the longitudinal axis in the first direction.

In embodiments, the biasing mechanism comprises one or more springs or other resiliently compressible or expandable mechanical members for storing mechanical energy. Preferably, the biasing mechanism comprises an arrangement of two springs locating one on either side of the container collar (i.e. at a 180° radial spacing).

The Applicant realizes that for effective actuation of the discharge mechanism (e.g. valve or pump) of the drug discharge device the biasing mechanism should be capable of storing (and releasing) sufficient biasing energy to both overcome the pre-determined force of the pre-load mechanism and to actuate that discharge mechanism. Thus, for example where the discharge mechanism comprises a valve or pump having a return spring, the biasing mechanism should be capable of providing sufficient biasing energy to overcome that return spring to reliably fire the valve or pump.

The Applicant however realizes that it is desirable that the actuating force, which is applied by the patient to the at least one finger operable member be kept to a minimum. Desirably also, the overall size of the device is kept relatively small (e.g. fits comfortably in the patient's hand) from both an ergonomics and aesthetics standpoint. Desirably also, the dispenser device is made of plastic components, although this brings with it the challenge that the mechanical strength of certain plastics reduces with time, particularly if they are left in a tensed state.

Thus, the biasing mechanism is in embodiments arranged to provide an initial high biasing tension (e.g. to be equal to or greater than the force required to actuate a return spring of the valve or pump, but necessarily also less than that of the pre-determined threshold force of the pre-load mechanism), and further to have a low spring rate (i.e. the tension therein increases by only a low rate as the biasing mechanism is moved in response to user-actuation of the at least one finger operable member). Applicant realizes that it can be difficult to achieve this with a compression spring since it would require making a spring with a low spring rate then compressing it a given distance to achieve the initial high biasing tension, and then assembling it into the device. It would therefore always be putting a load upon any plastic components of the device.

Thus, in embodiments the biasing mechanism comprises one or more extension springs.

In embodiments, the degree of extension of the or each extension spring is greater than that of the degree of spring extension required to overcome any return spring (e.g. valve or pump return spring) of the discharge mechanism to fire that discharge mechanism.

Preferably, the extension springs have a closed coil form, which in embodiments defines an initial biasing tension in its 'at rest' state. In embodiments, that initial biasing tension provided by the one or more extension springs in combination is just below (e.g. from 1 to 15N, such as from 3 to 10N below) that of the pre-determined threshold force of the pre-load mechanism.

In embodiments, the one or more extension springs define a low spring rate. That is to say extension thereof does not require undue user force to be applied. This is advantageous in that extension thereof in response to user actuation of the at least one finger operable member does not thereby, put undue strain on the user. In embodiments, the spring rate of the or each extension spring is in the range from 0.5 to 5 N/mm, such as from 1 to 4 N/mm.

There is further provided to the container collar, a pre-load mechanism to prevent transfer of the biasing energy to the container collar to both (i) move said discharge device along the longitudinal axis in the first direction to actuate the discharge mechanism and also (ii) to actuate said actuation counter until a pre-determined threshold force is overcome.

Thus, initially as the transfer element moves along the longitudinal axis in response to patient actuation of the at least one finger operable member the spacing (along the longitudinal axis) between the transfer element and the container collar (which does not move) increases and biasing energy builds up in the biasing mechanism. Once however, the pre-determined threshold force as defined by the pre-load mechanism is exceeded, the biasing energy is released and the container collar is thereby, drawn along the longitudinal axis and in the first direction, which action results in actuation of the discharge mechanism resulting in discharge of drug formulation through the discharge channel and to the outlet for delivery to the patient.

In other words, the pre-load mechanism acts such as to prevent actuation of the discharge mechanism of the drug discharge device until a pre-determined threshold force is applied to the at least one finger operable member. The pre-determined threshold force may thus, be thought of as a 'barrier' force which must first be overcome before the energy stored in the biasing mechanism may be released to actuate the discharge mechanism. In essence, the pre-load mechanism acts as a 'commitment' feature, which allows release of actuating energy to the discharge mechanism only when the 'barrier' force has been exceeded.

The quantum of pre-determined force that is to be overcome before actuation of the discharge mechanism is enabled is selected according to various factors including the typical user profile, nature of the drug formulation and the desired discharge characteristics.

Typically, the pre-determined threshold force is in the range from 5 to 40N, more typically from 10 to 30N (e.g. 15-25N). That is to say, typically from 5 to 40N, more typically from 10 to 30N (e.g. 15-25N) of force must be applied to overcome the pre-determined threshold before actuation of the discharge mechanism is enabled. Such values tend to correspond to a force which presents a suitable 'barrier force' to a weak, nondescript or unintended finger movement whilst readily being overcome by the determined finger (or thumb) action of a user. It will be appreciated that if the device is designed for use by a child or elderly patient it may have a lower pre-determined force than that designed for adult usage.

In embodiments, the pre-load mechanism is interposed between the container collar and the housing.

In embodiments, the pre-load mechanism comprises one or more detents formed on the container collar for engagement with part of the housing, the or all of the detents being disengageable from the housing when the pre-determined threshold force is applied to the transfer element via the at least one finger operable member so as to allow the container collar to move along the longitudinal axis in such a way that the discharge mechanism is actuated.

Preferably, each detent comprises a flexible (e.g. resilient) support limb, such as a support leg which engages (e.g. latches to) a step or abutment provided to the housing. When the pre-determined threshold force is overcome, the or each flexible support limb disengages from the step or abutment to allow the container collar to move along the longitudinal axis such that the discharge mechanism is actuated. In embodiments, the or each support limb is provided to the lower end of the container collar (i.e. that end which is closest to the outlet). An arrangement of from two to four (e.g. three) flexible support limbs is particularly preferred. Alternatively, the or each support limb may have a hinged or articulated form.

In embodiments, a guide mechanism is provided to the transfer element (e.g. extension collar) to guide the disengagement of the flexible support limb from its respective step or abutment on the housing. Preferably, such guide mechanism comprises a guide ramp, which interacts with a shaped head of each flexible support limb.

In embodiments, a reseat guide mechanism is provided to the transfer element (e.g. extension collar) to guide the re-engagement of the flexible support limb with its respective step or abutment on the housing. Preferably, such reseat guide mechanism comprises a reseat guide ramp, which interacts with a shaped reseat head of each flexible support limb.

In embodiments the 'disengagement' guide mechanism (e.g.) ramp interacts with an outer shaped head of each flexible support limb and the 're-engagement' reseat guide mechanism (e.g. ramp) interacts with an inner shaped reseat head of each flexible support limb.

Alternatively, the pre-load mechanism may comprise of one or more detents formed on the housing for engagement with part of the container collar, the or all of the detents being disengageable from the container collar when the pre-determined threshold force is applied to the transfer element via the at least one finger operable member so as to allow the discharge mechanism to be actuated.

The pre-load mechanism herein acts such as to prevent transfer of biasing energy to the container collar to actuate the actuation counter until a pre-determined threshold force is overcome. Thus, a count is registered by the actuation counter only in response to a user actuation that is sufficient to overcome the 'barrier' force provided by the pre-load mechanism and which thereby results in dispensing of a dose from the drug container.

Embodiments are envisaged in which the drug discharge device is reversibly removable from the housing of the drug dispenser device. In such embodiments the drug dispenser device comprises a housing assembly and a drug discharge device receivable thereby.

Embodiments are also envisaged where there is provided a kit of parts comprising a housing assembly as described above and a drug discharge device receivable thereby. The drug discharge device has a longitudinal axis and comprises a container for storing a drug formulation to be dispensed, a discharge mechanism and a discharge channel extending from said container for discharge of said drug formulation.

It is also envisaged that the housing assembly could be supplied as a separate item, into which a user or pharmacist later fits a suitable drug discharge device.

In embodiments, the drug dispenser device comprises a housing which comprises an outlet for insertion into a body cavity of a patient. In embodiments, the drug discharge device in the housing comprises a container for storing a drug formulation to be dispensed and a discharge mechanism for discharge of said drug formulation from said container to said outlet, the drug discharge device disposed in the housing such that the discharge mechanism is held stationary and the container is movable in a first direction relative to the discharge mechanism to put the device in a discharge mode where the formulation is discharged from the container to the outlet.

In embodiments, there is provided a catapult (or loading) arrangement for catapulting (or loading) the container in the first direction relative to the discharge mechanism comprising a first part attached to the container, a second part connected to the first part so that the first and second parts are movable towards and away from each other, a biasing force (mechanism) for biasing the first and second parts to a resting configuration thereof, a latch adapted in use to latch the first part against movement in the first direction when the second part is moved away from the first part in said first direction against the biasing force (mechanism), and a latch release adapted for releasing the latch, when the second part has moved a predetermined distance from the first part in the first direction, to enable the biasing force (mechanism) to move the first part in the first direction towards the second part and carry the container in the first direction relative to the discharge mechanism to put the drug discharge device in its discharge mode.

In embodiments, the actuation counter herein is configured and arranged to be actuated by movement of the first part or the container in the first direction on release of the latch.

The latch may be provided on the first part and the latch release may be provided on the second part. The first part may be a collar. The second part may be a collar, for instance of annular form. The latch may be formed by one or more projections of the first part. The latch release may be formed by a surface thereof for contacting the latch for release thereof. The biasing force (mechanism) may be provided by a resilient element, typically a spring. The device may have an actuating mechanism for moving the second part of the catapult (loading) arrangement in the first direction the predetermined distance from the first part for the latch release to release the latch. The actuating mechanism may comprise at least one finger operable member, for instance one or more levers, such as in the embodiments hereinafter to be described with reference to the drawings.

The drug dispenser device is in embodiments, an inhaler, more suitably of the well-known "metered dose inhaler" (MDI) type, and yet more suitably a hand-held, hand-operable breath-coordinated MDI. In such a MDI, the patient manually actuates the MDI for release of the drug from the drug discharge device while concurrently inhaling at the outlet. Thus inhalation and actuation are coordinated. This is in distinction from breath-operated MDIs, where the inhalation event itself actuates the MDI so that no coordination is required.

According to another aspect of the present invention there is provided method of use of an actuation counter according to claim 81 hereof.

Additional aspects and features of the present invention are set forth in the claims and in the description of exemplary embodiments of the present invention which now follow with reference to the accompanying Figures of drawings. Such exemplary embodiments may or may not be practiced mutually exclusive of each other, whereby each embodiment may incorporate one or more features of one or more of the other embodiments. It should be appreciated that the exemplary embodiments are set forth to illustrate the invention, and that the invention is not limited to these embodiments.

Figure 1:
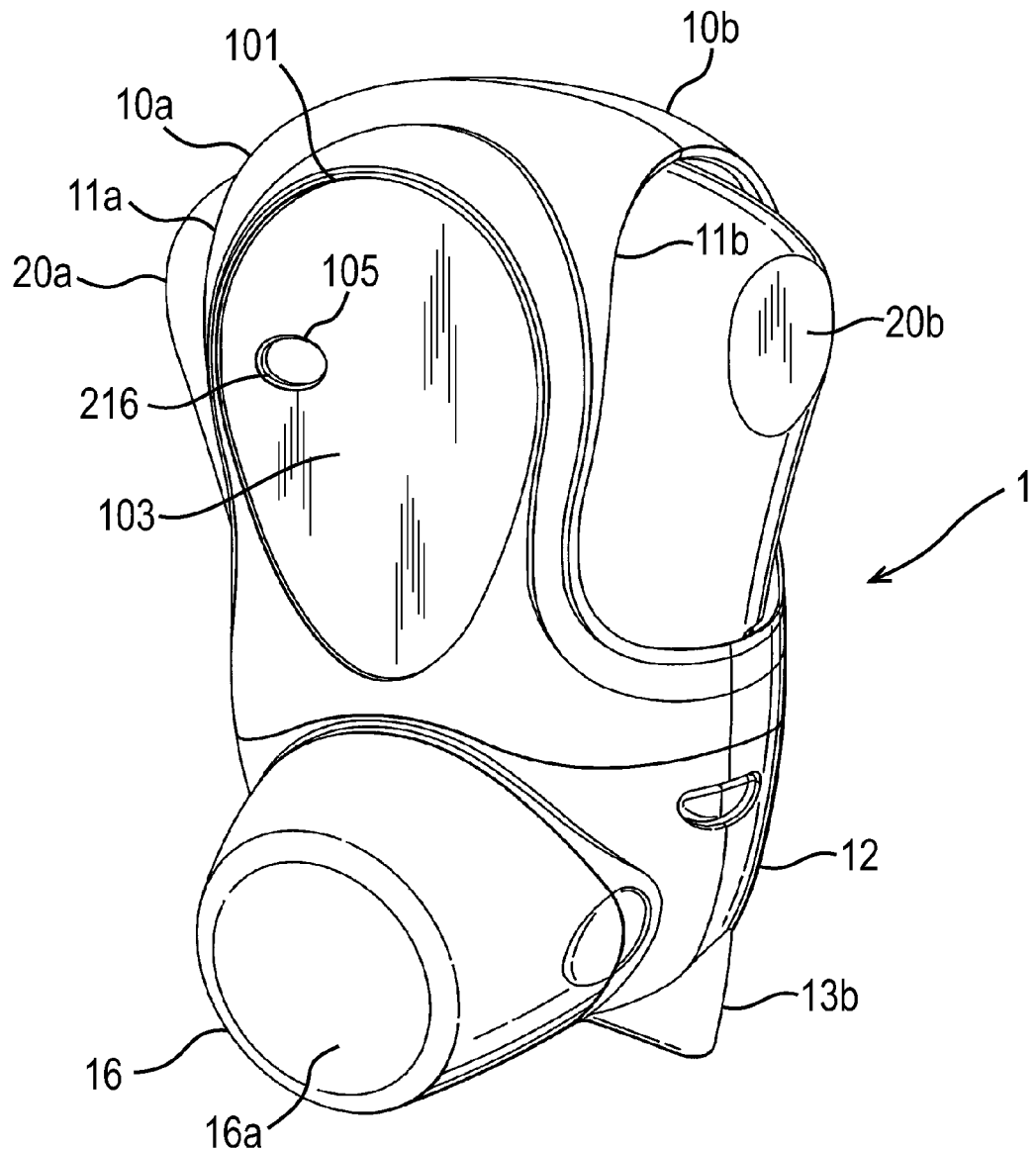
FIG. 1 shows a perspective view of a hand-held, hand-operable, breath coordinated drug dispenser device of the MDI type herein in the 'at rest' position.
Figure 3B:
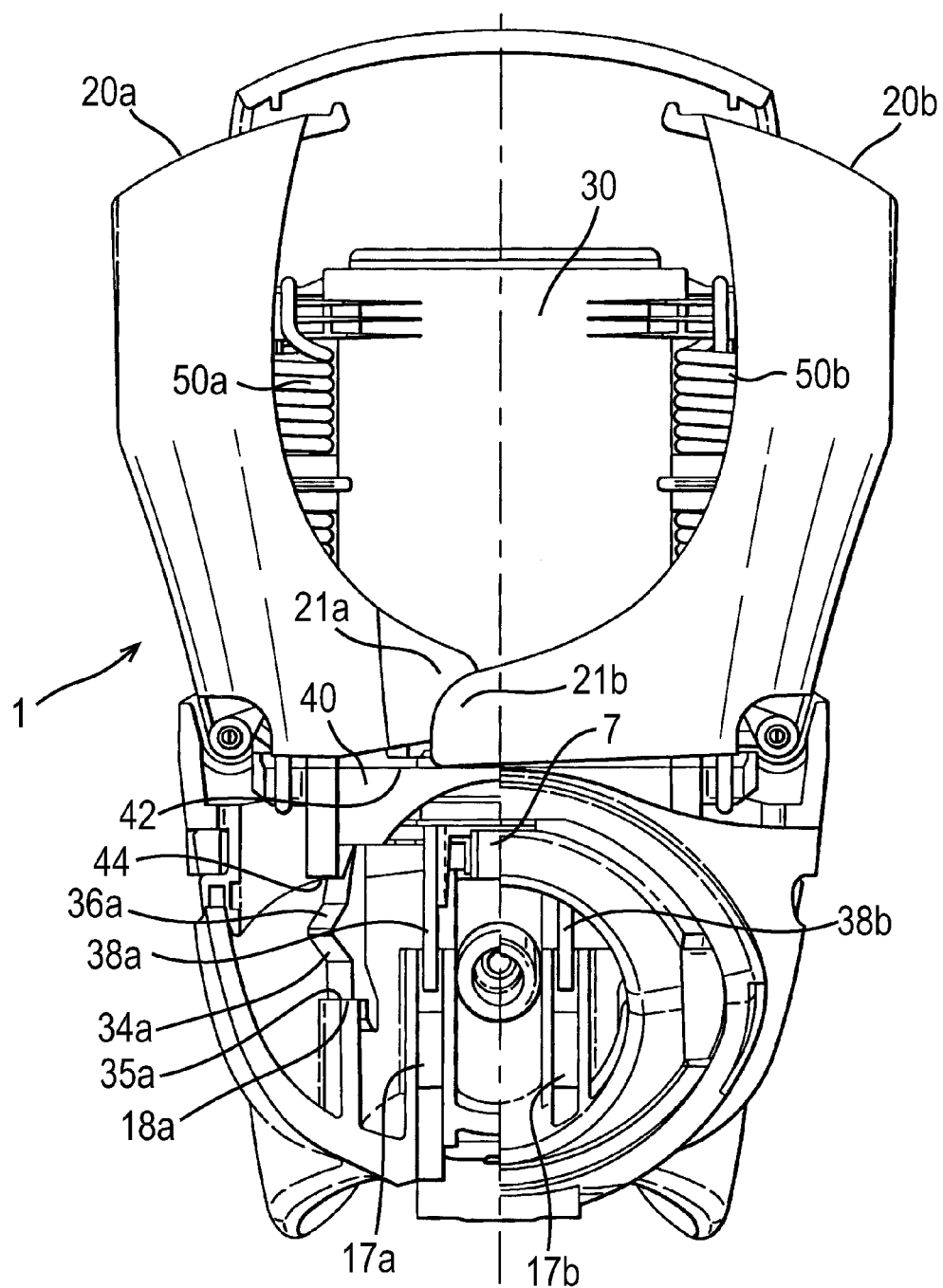
Figure 4A:
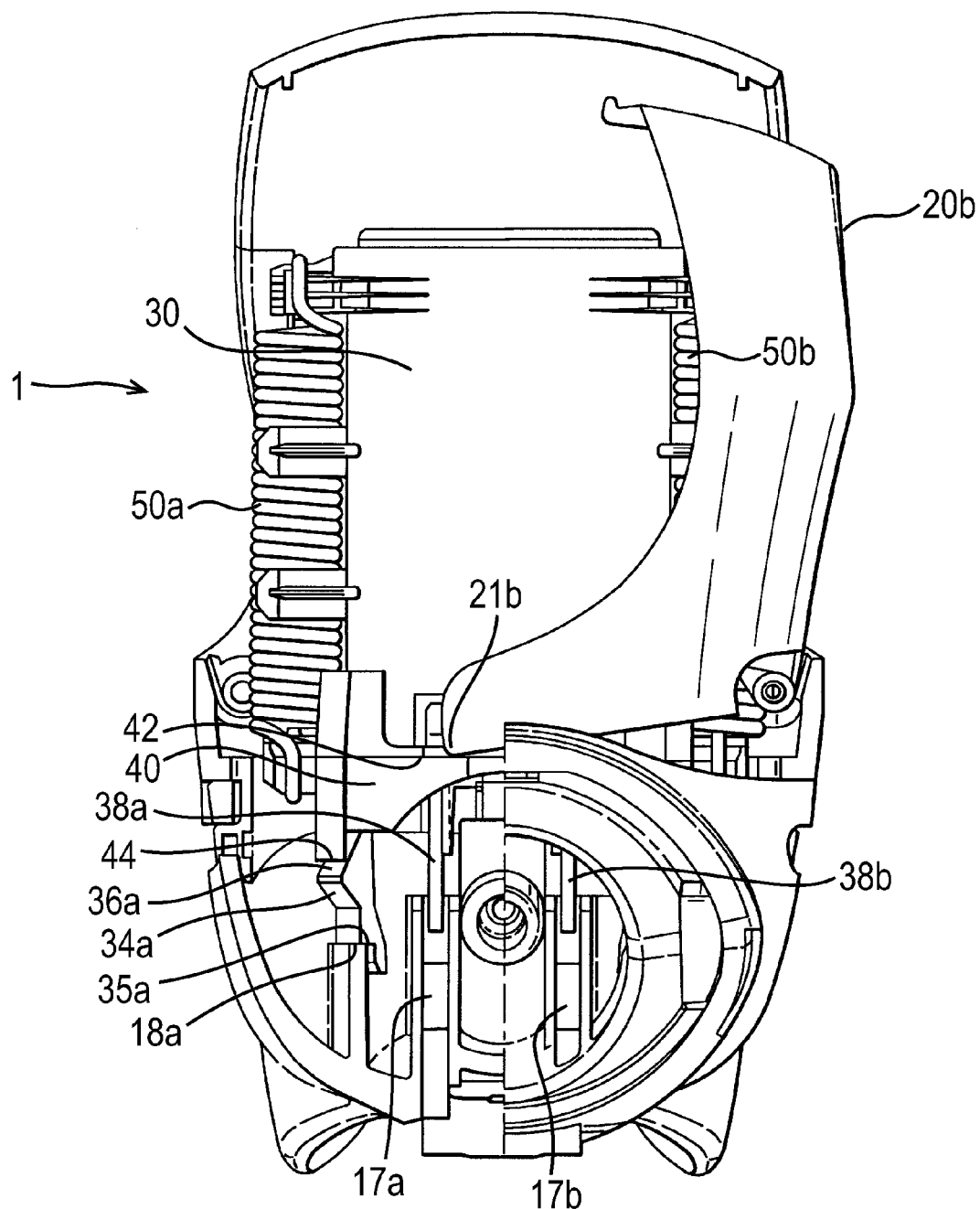
Figure 4B:
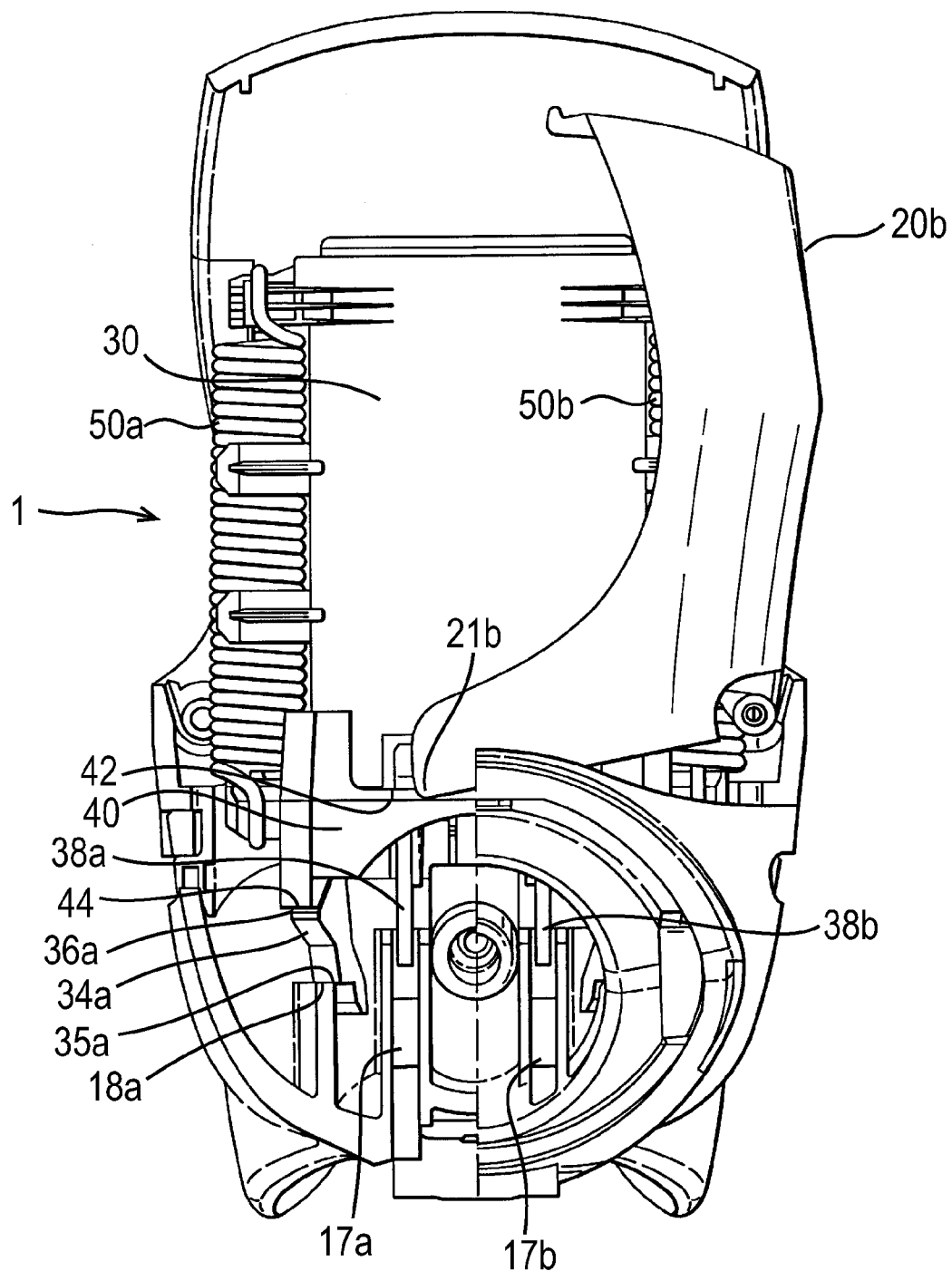
Figure 4C:
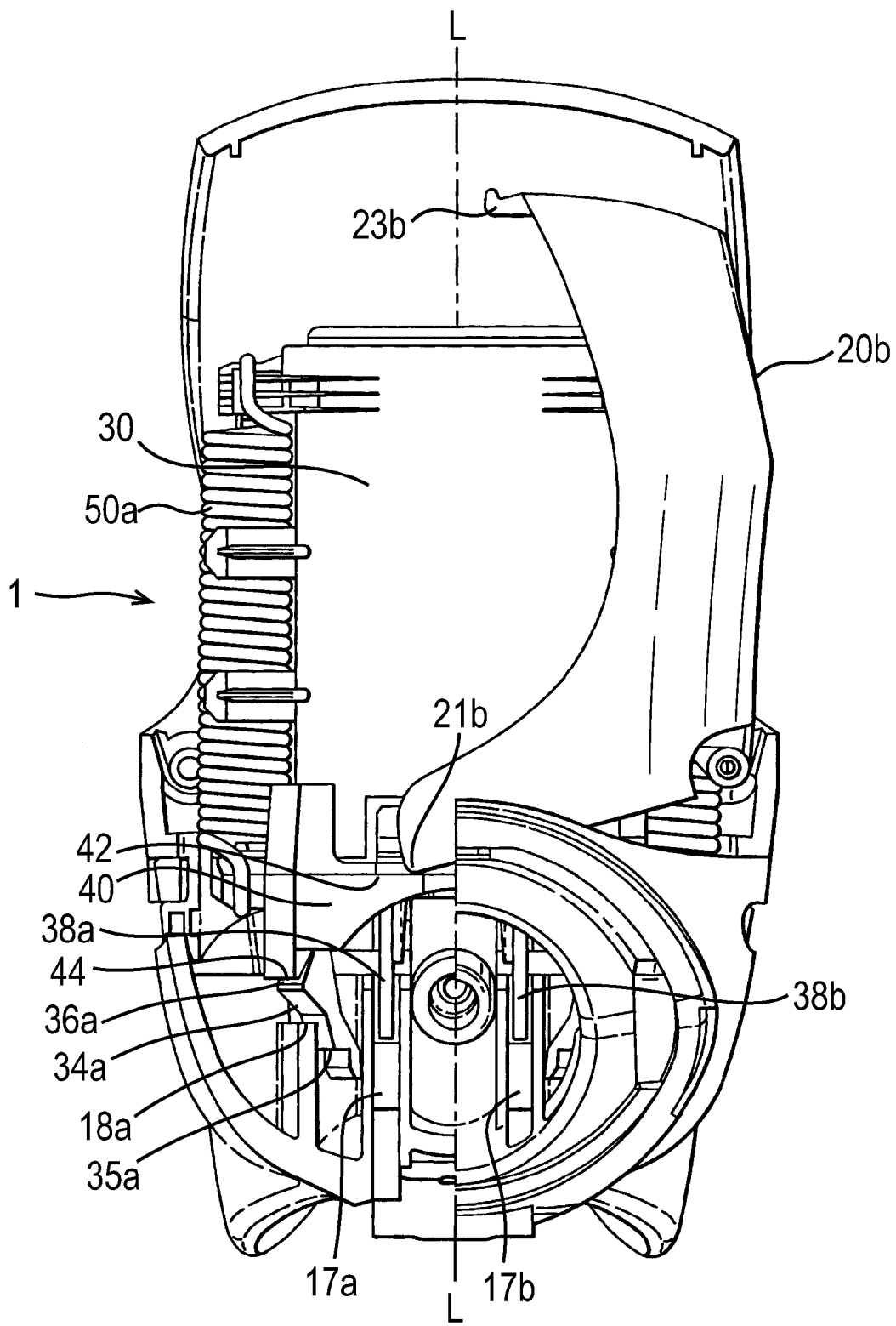
Figure 6:
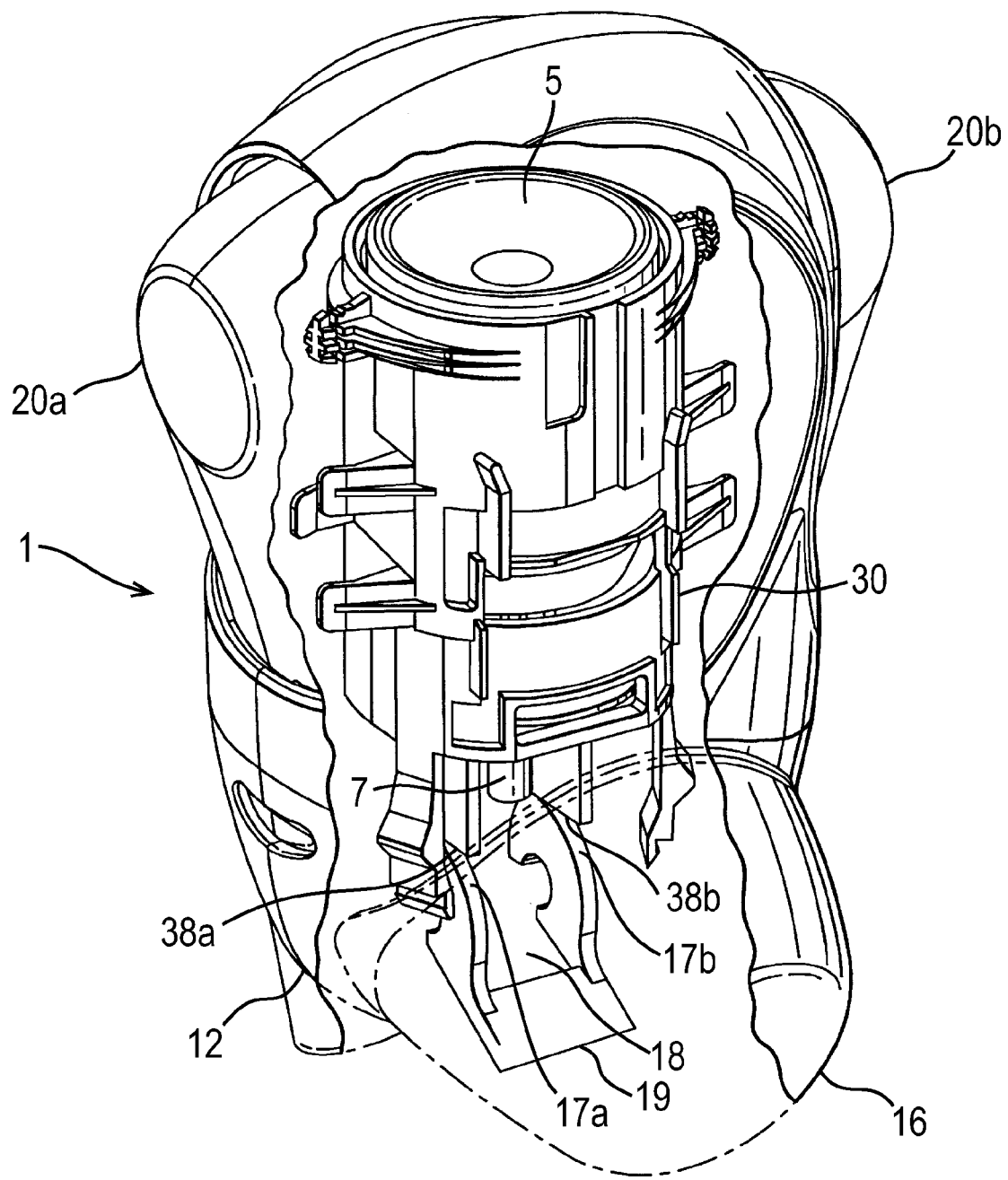
Figure 7:
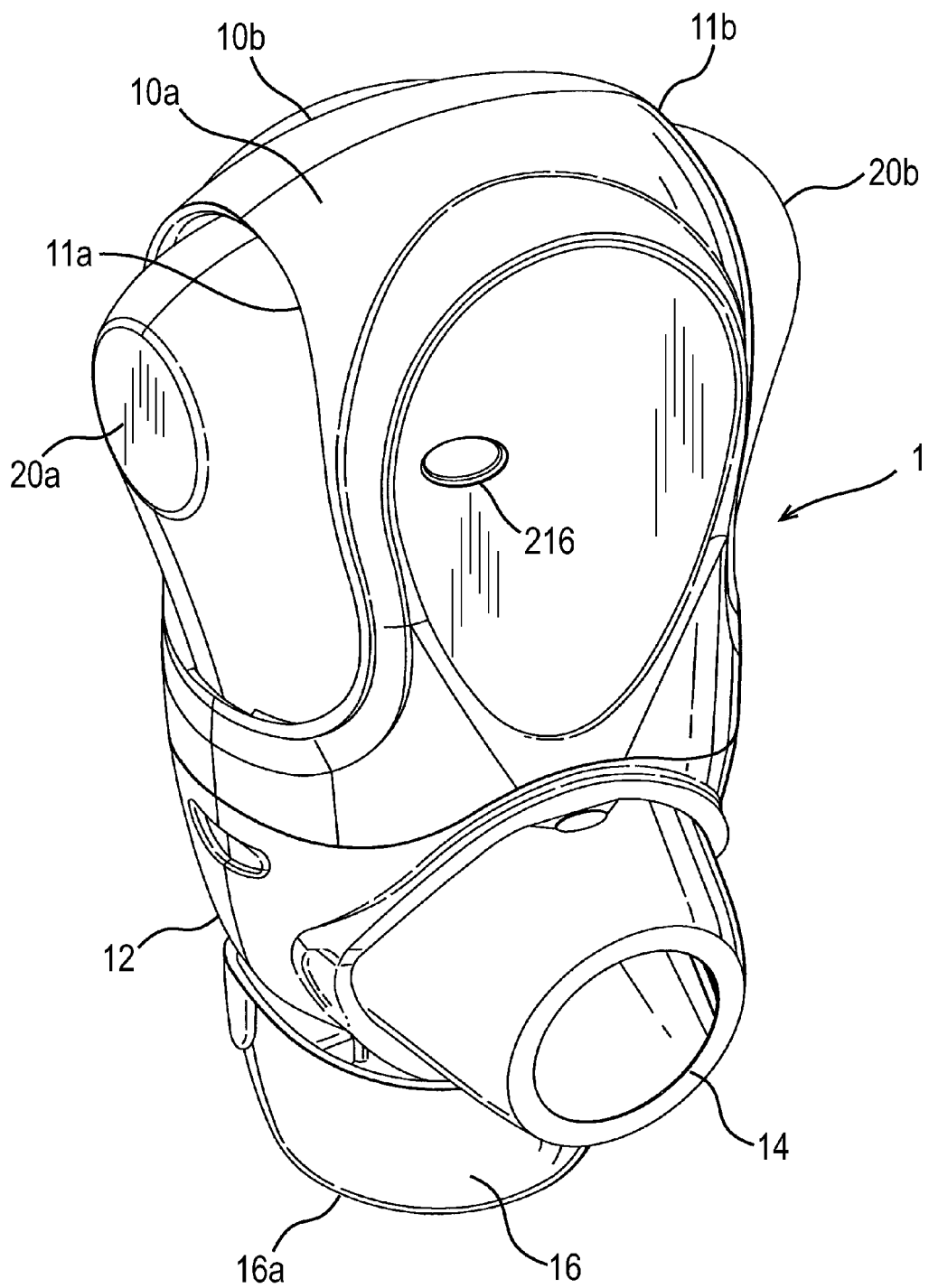
Figure 8:
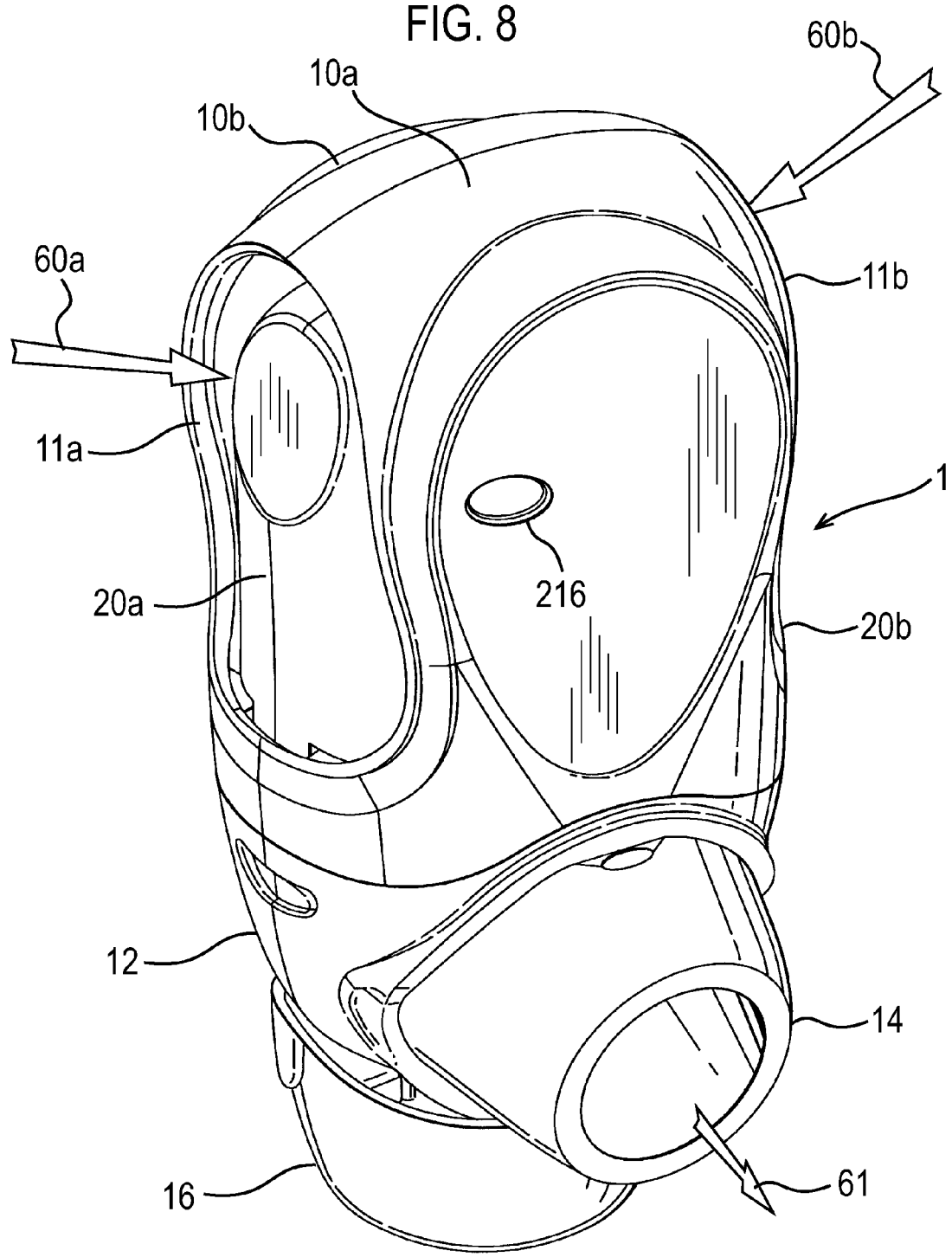
Figure 9:
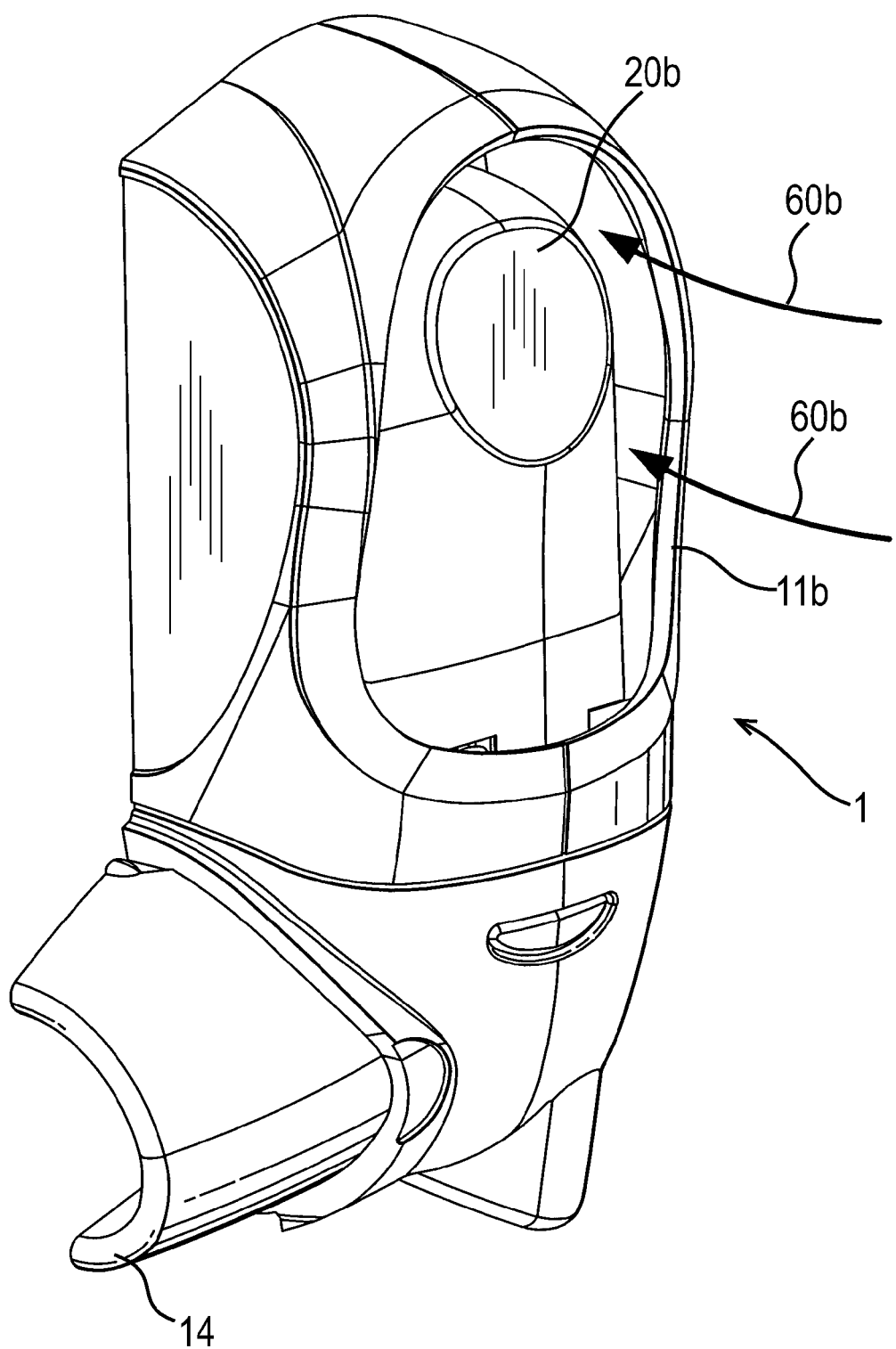
Figure 10:
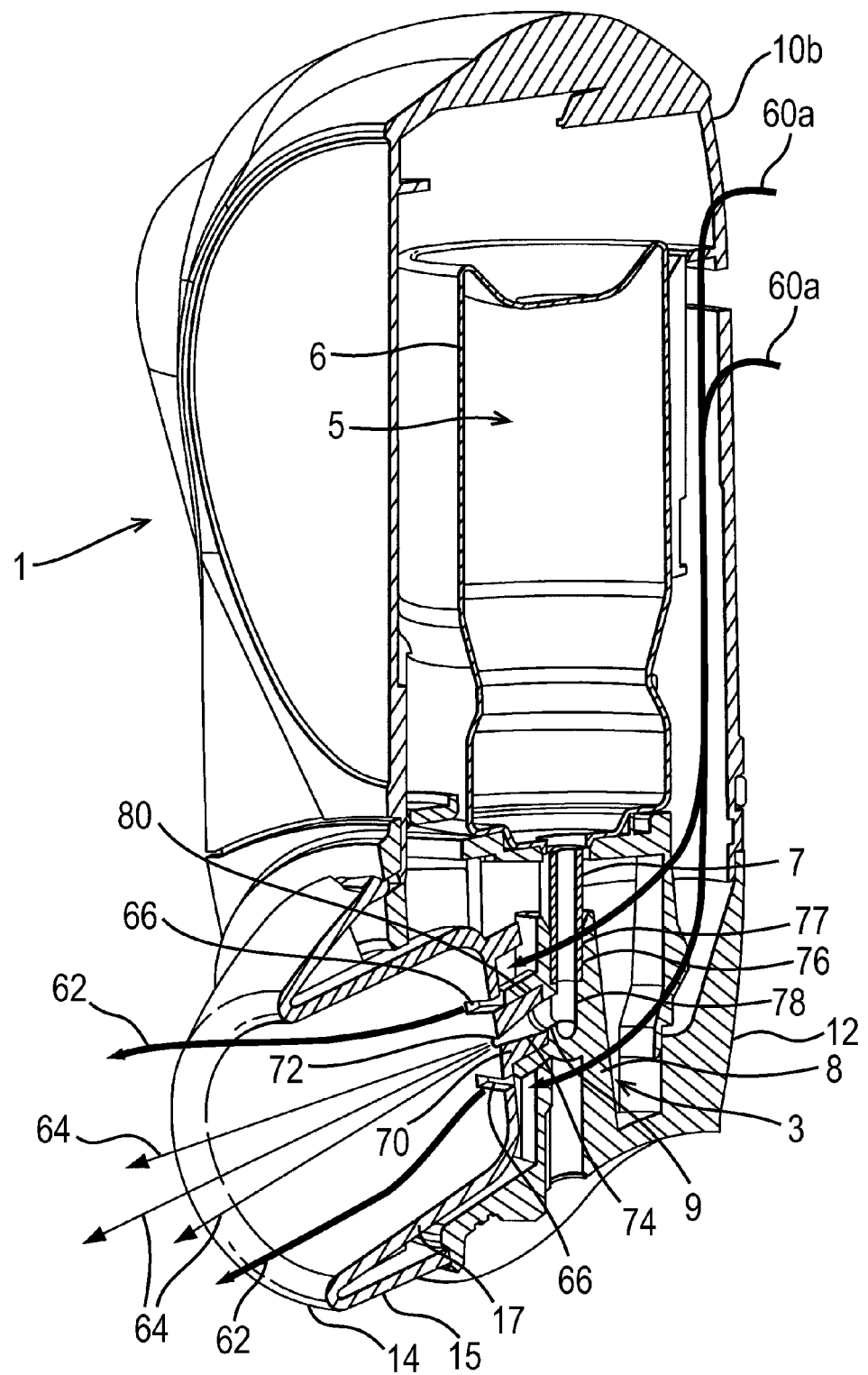
Figure 11:
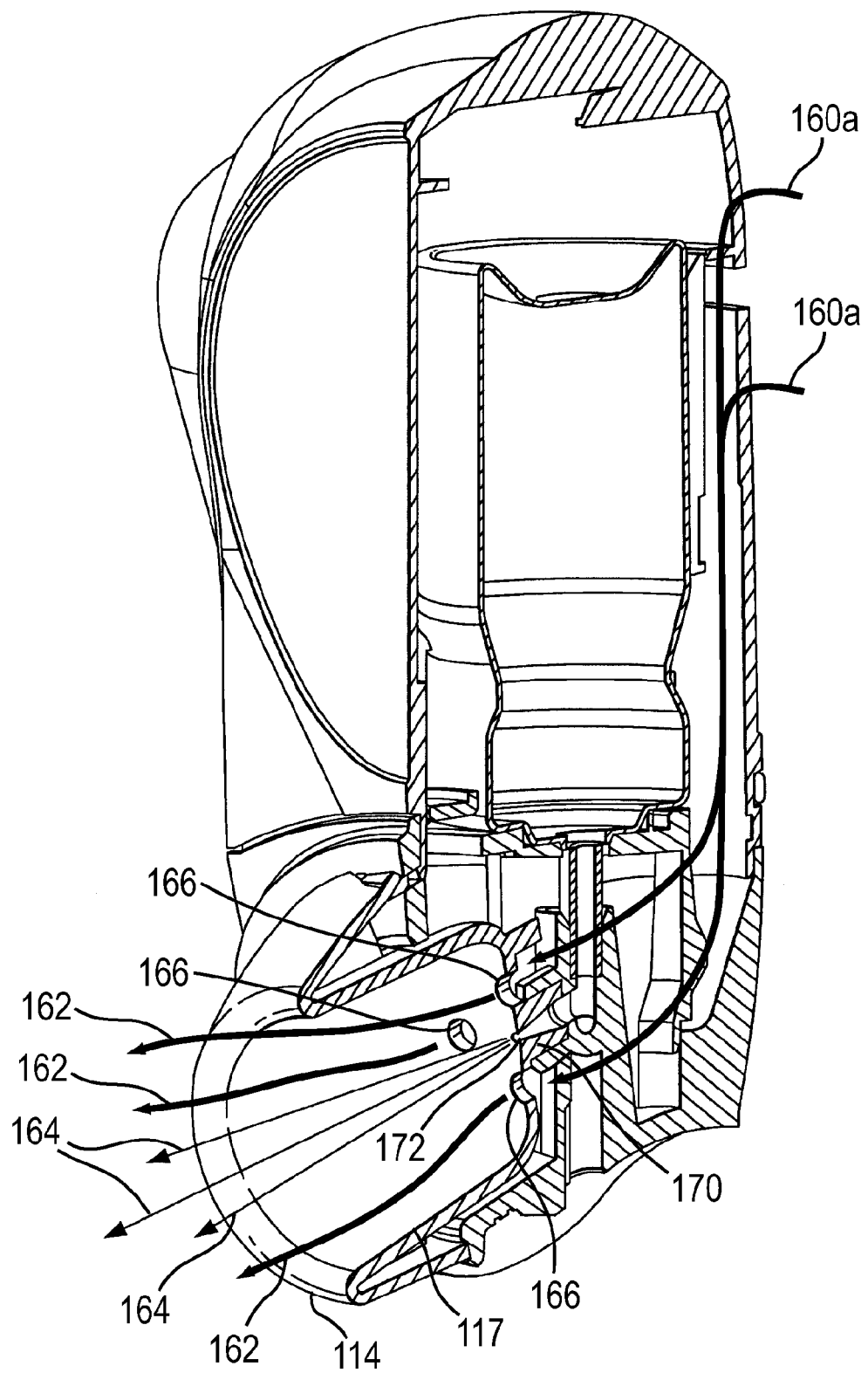
Figure 14A:
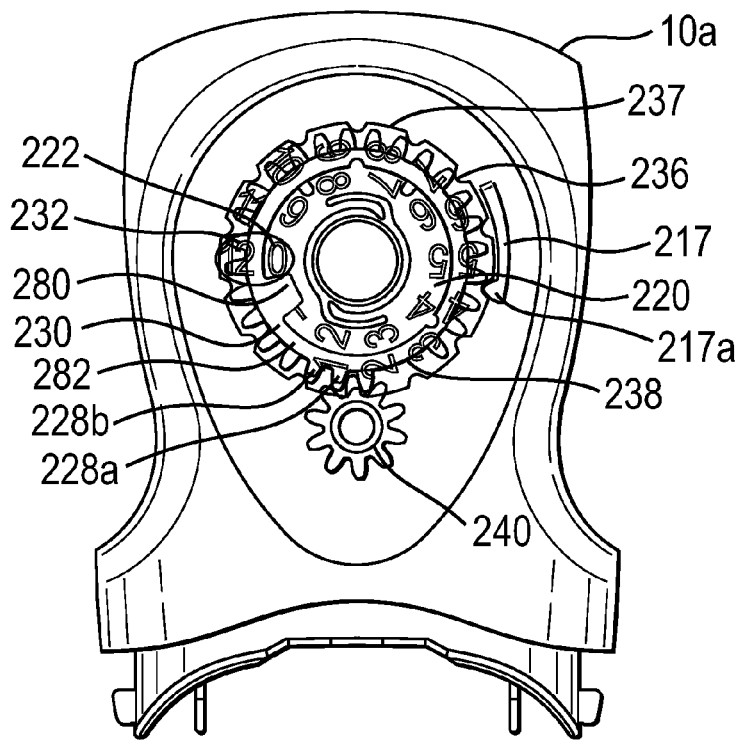
Figure 14B:
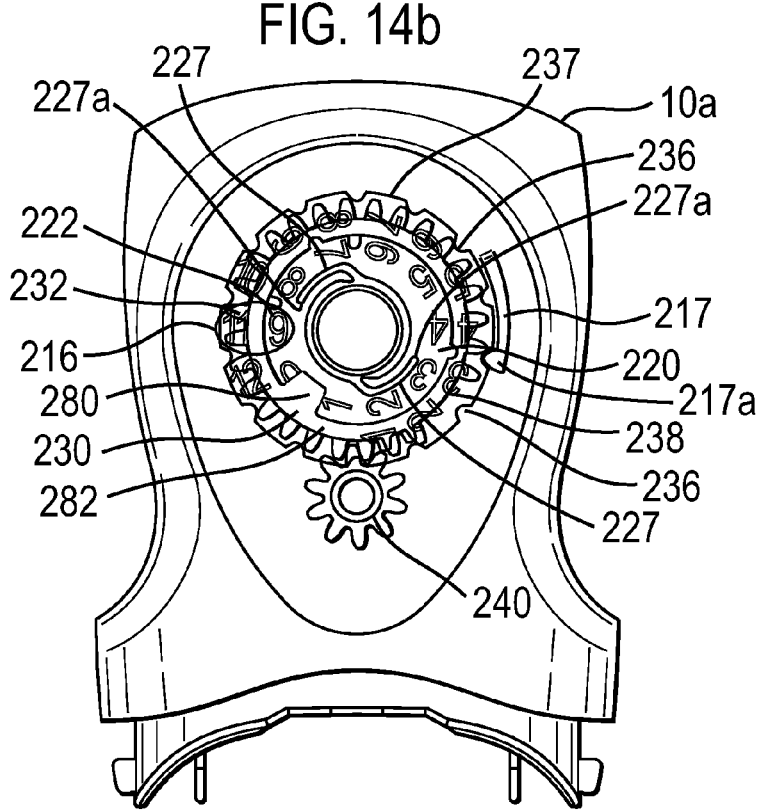
Figure 15A:
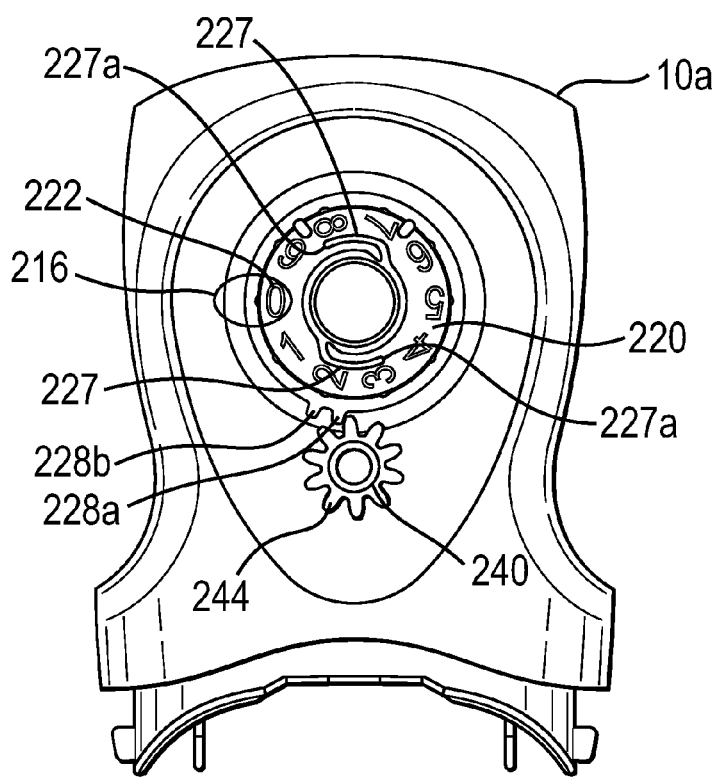
Figure 15B:
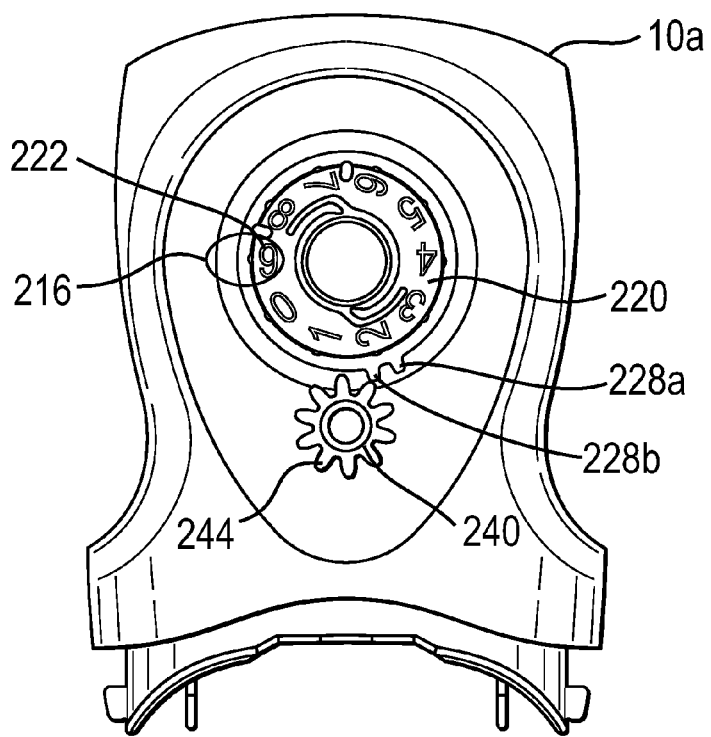
Figure 16A:
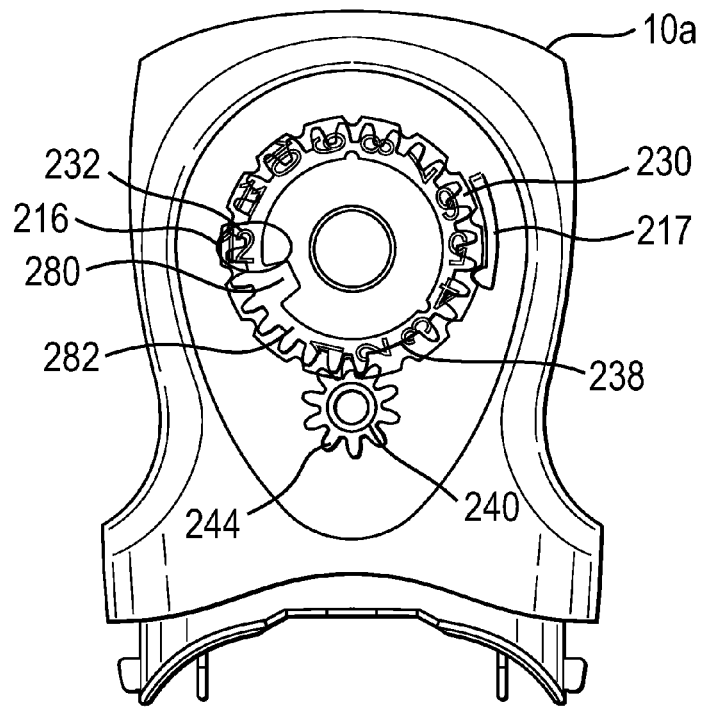
Figure 16B:
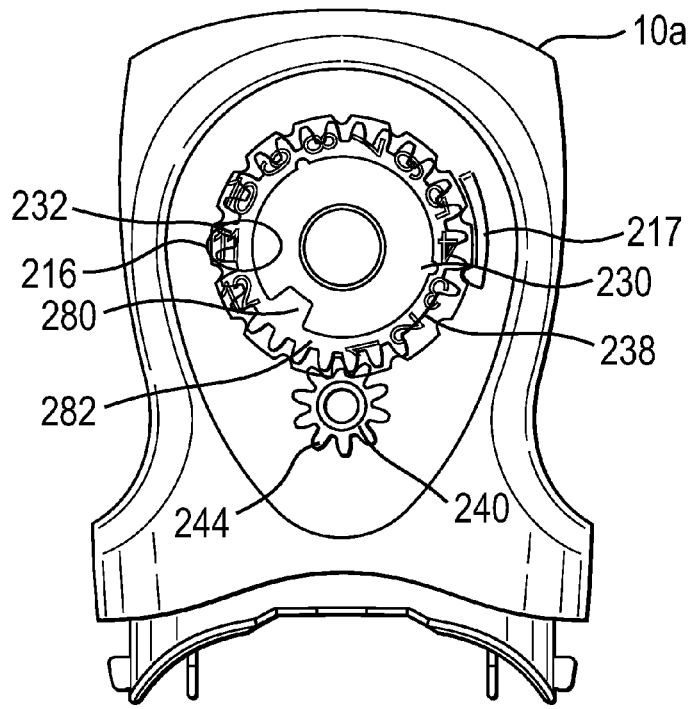
Figure 17A:
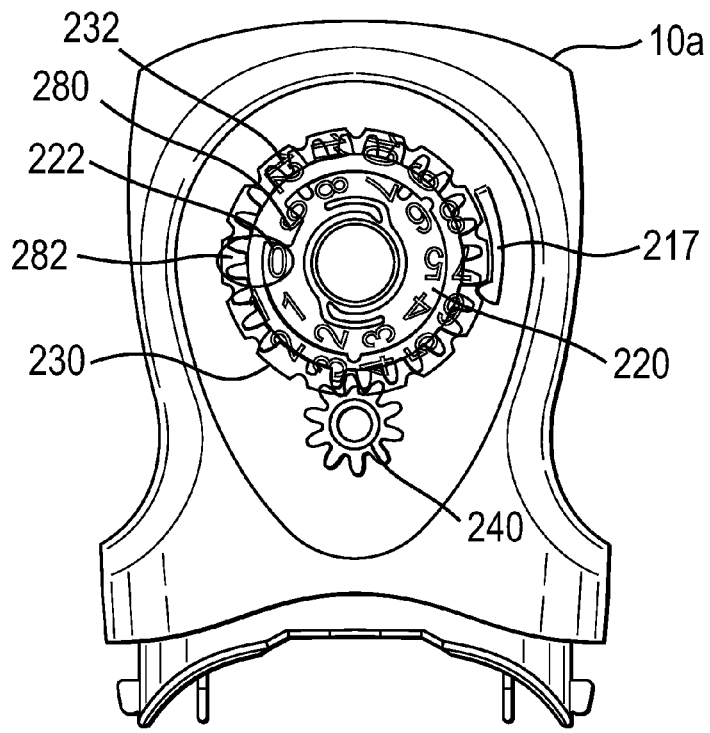
Figure 17B:
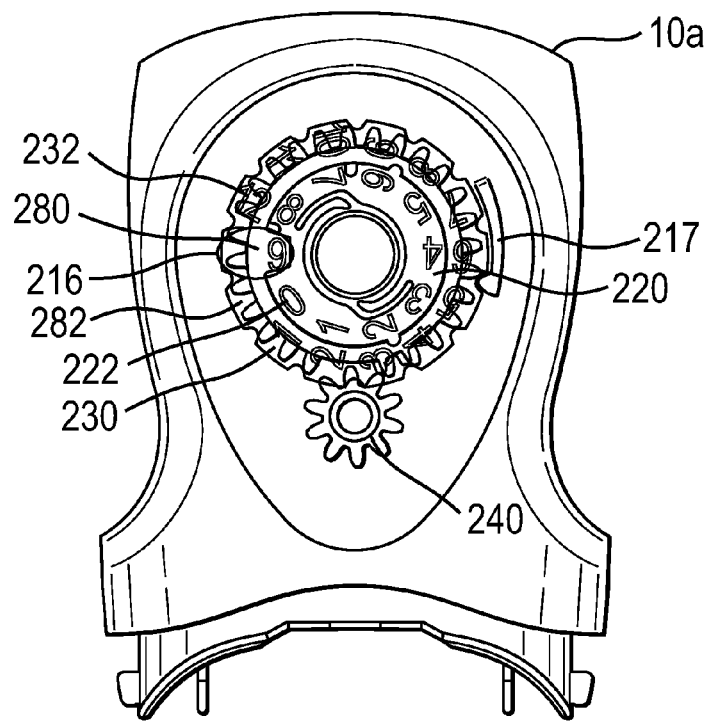
Figure 20:
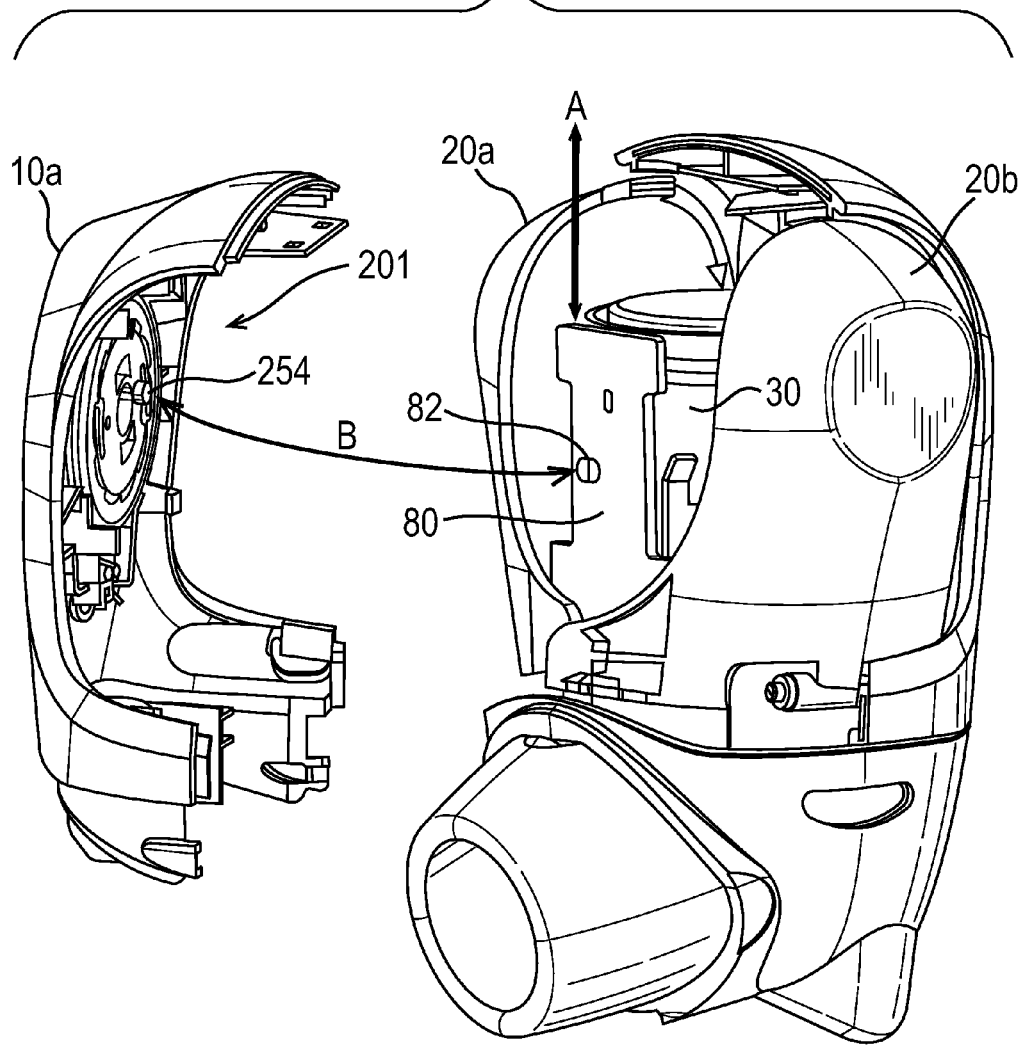
Figure 21:
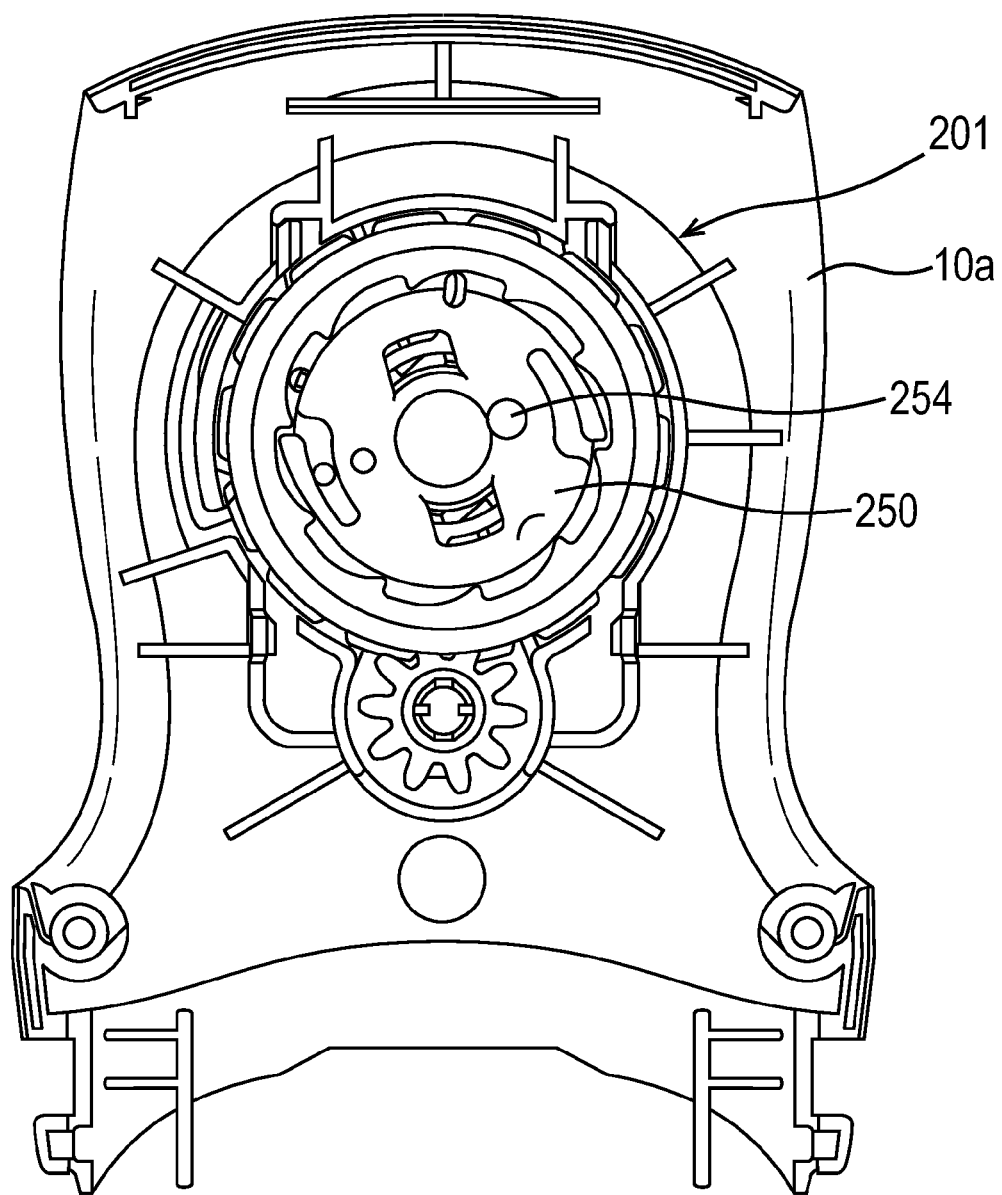
Figure 22:
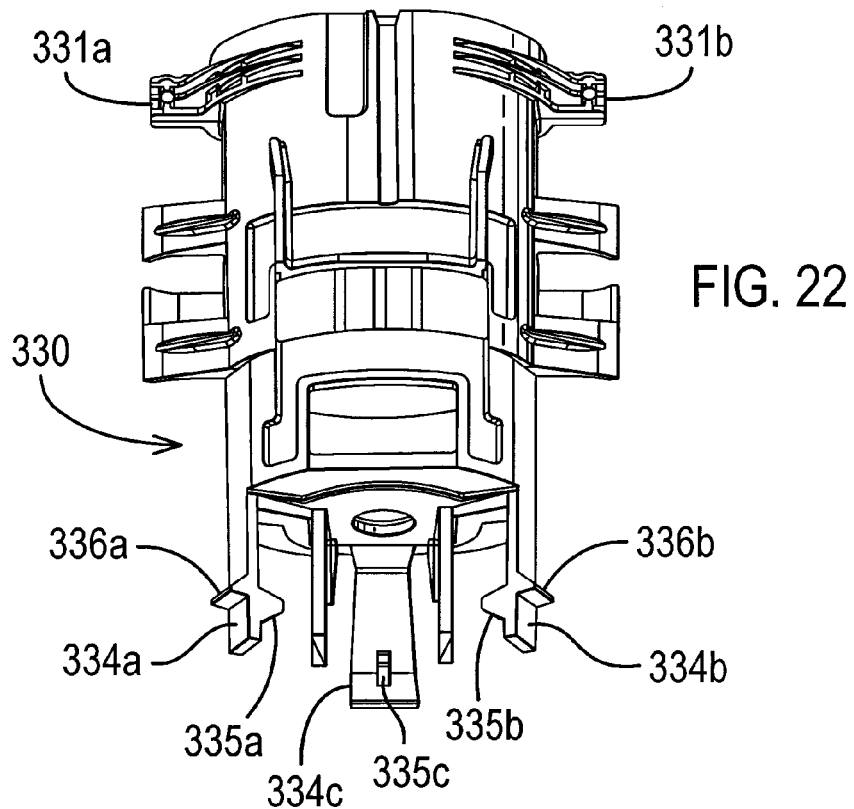
Figure 23:
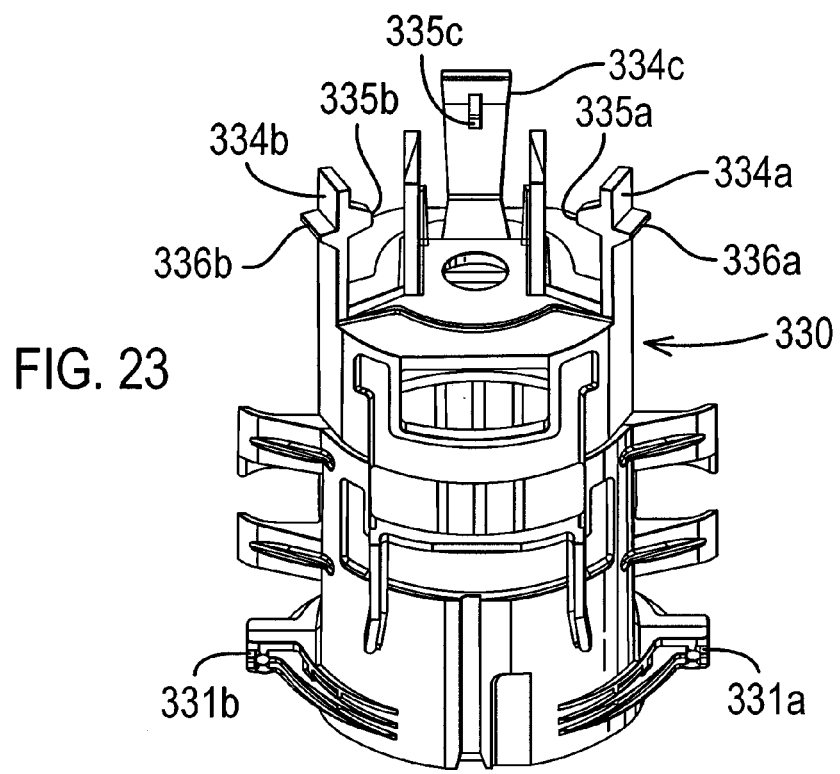
Figure 24:
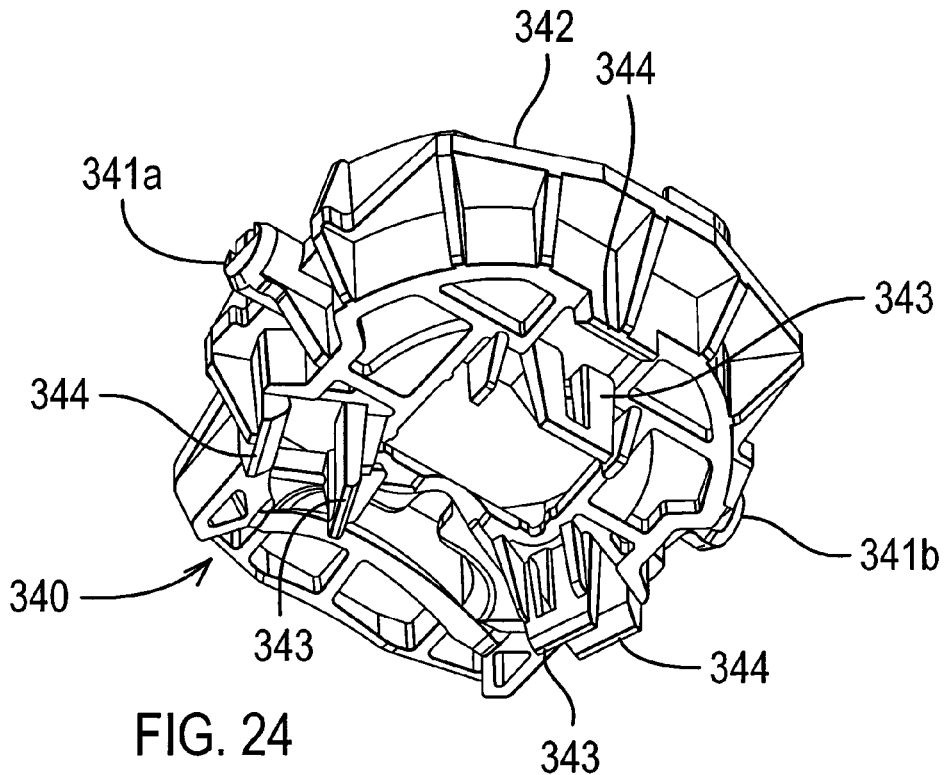
Figure 25:
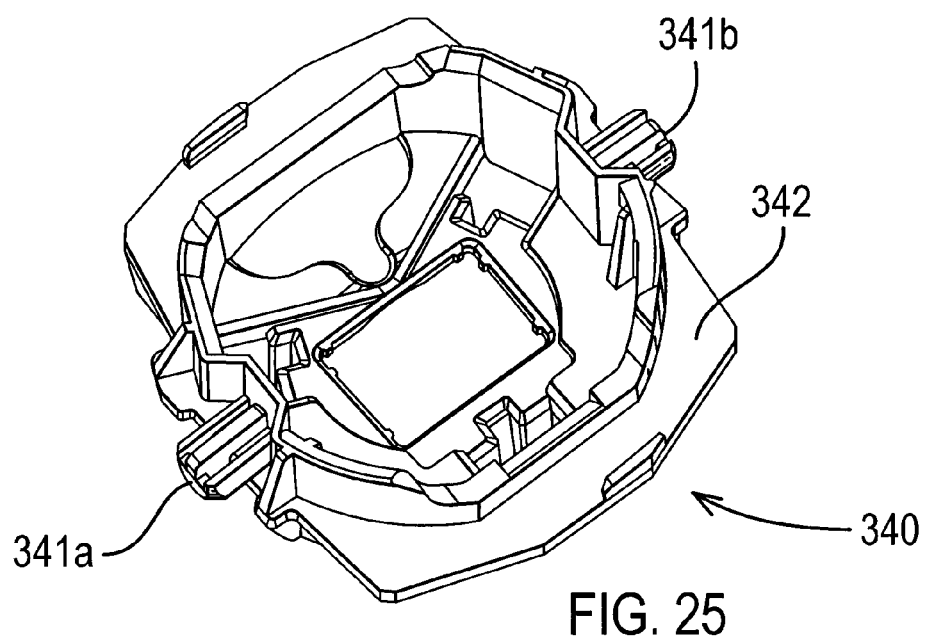
Figure 26C:
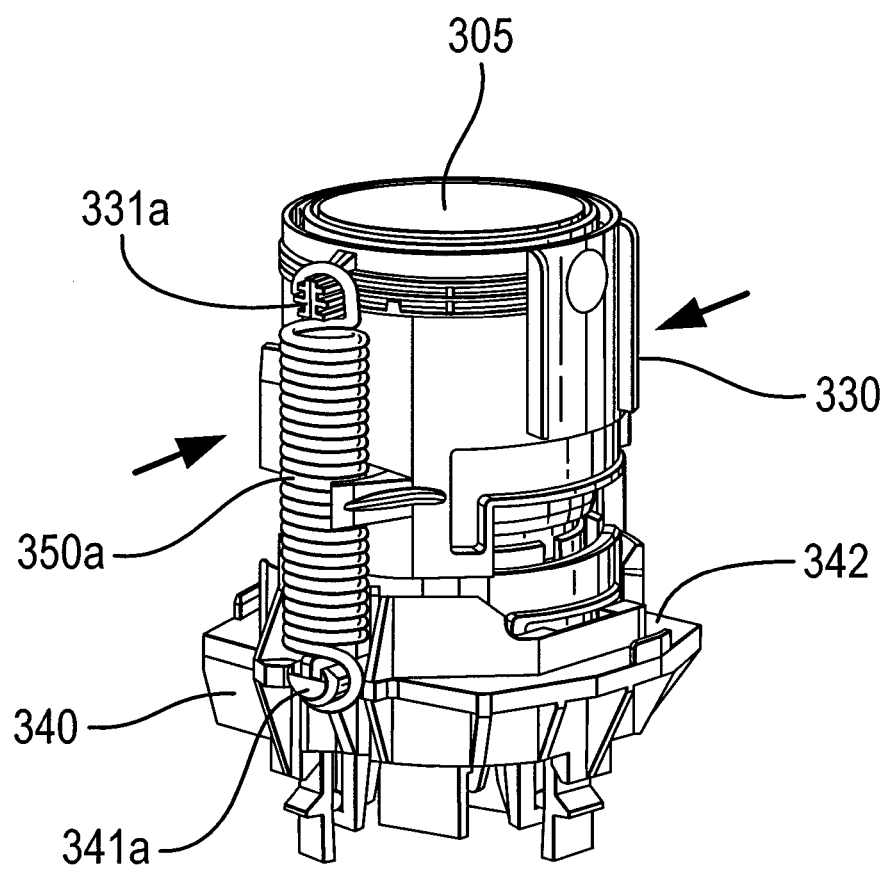
Figure 27A:
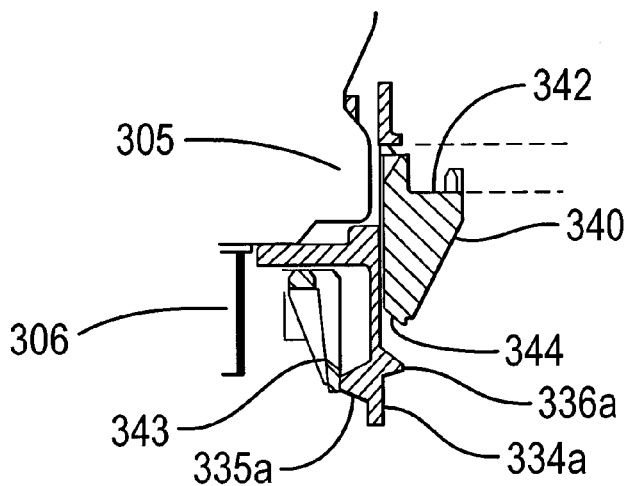
Figure 27B:
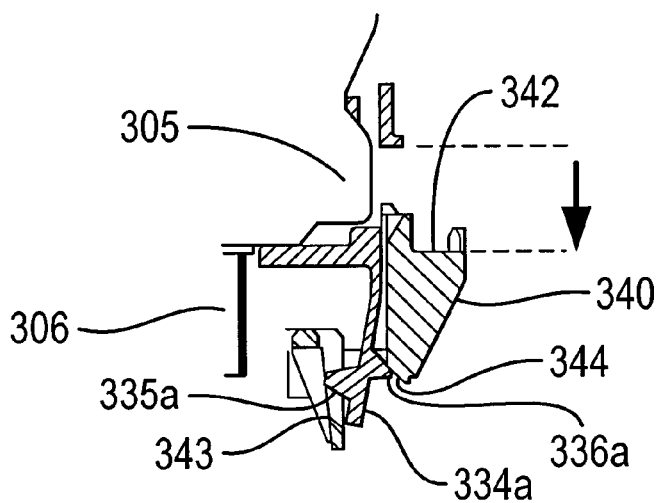
Figure 27C:
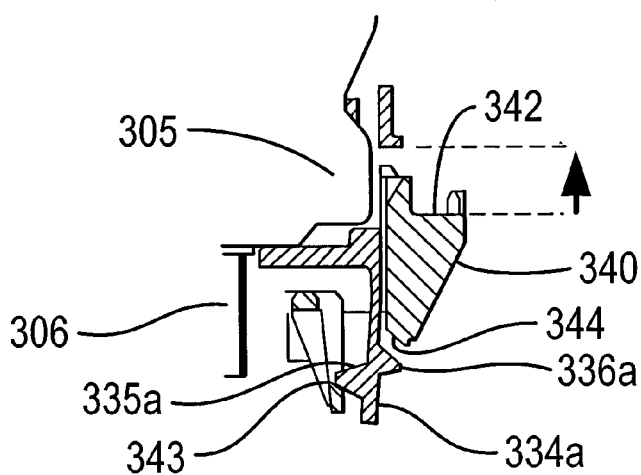
Figure 29A:
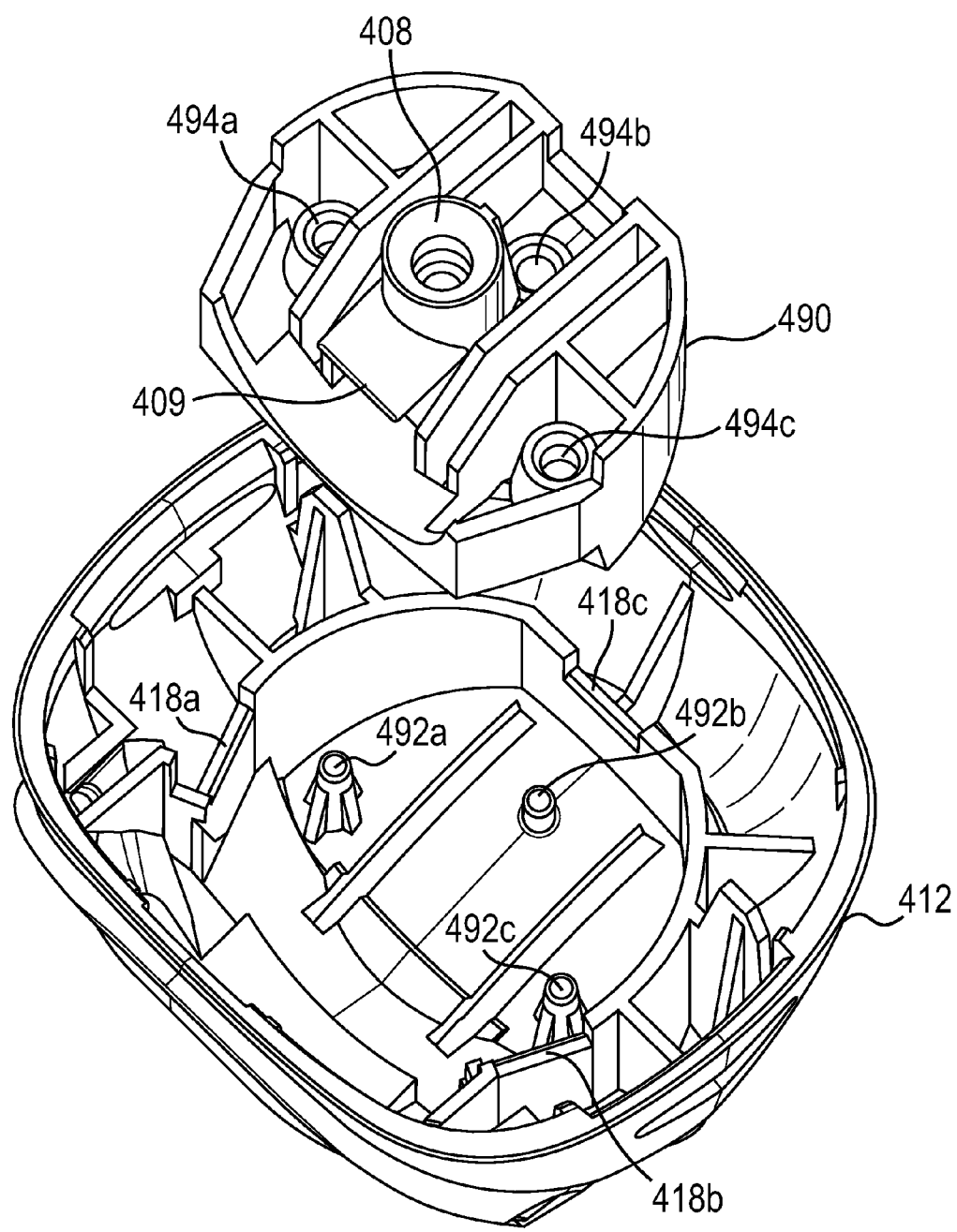
Figure 29B:
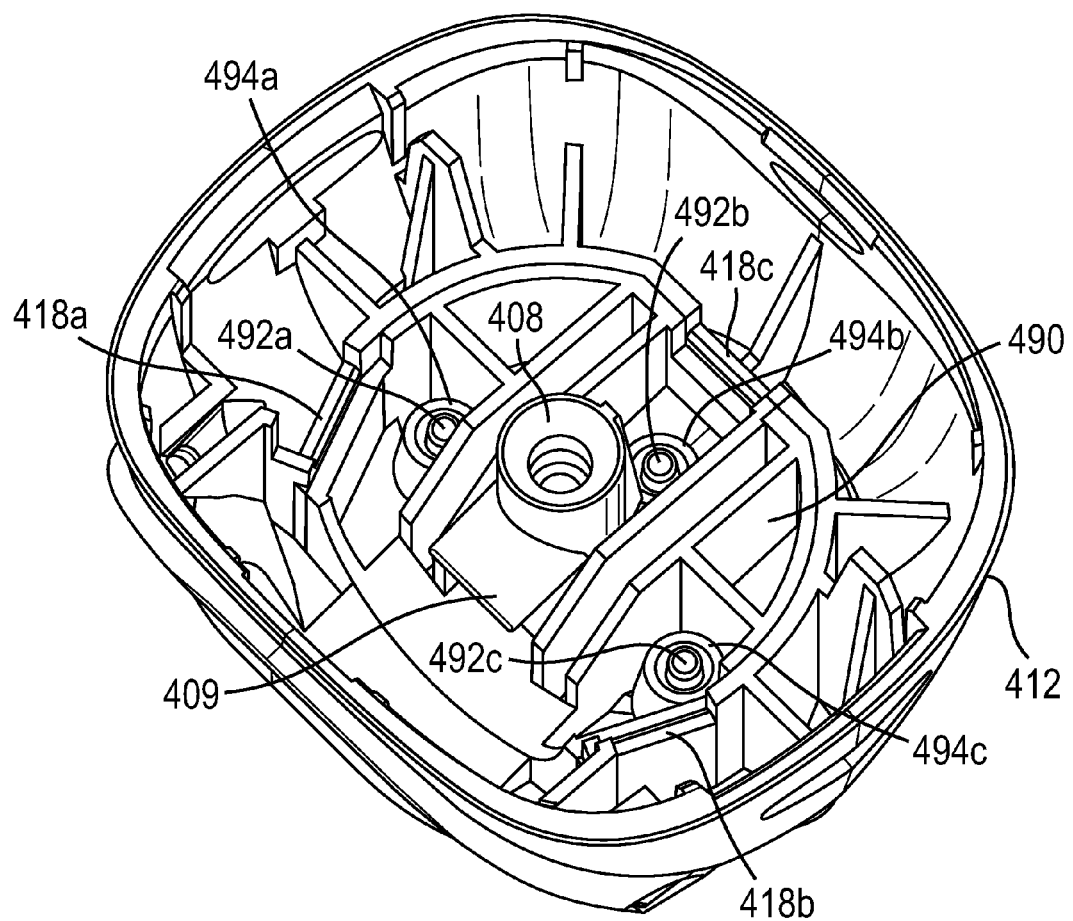
Figure 30A:
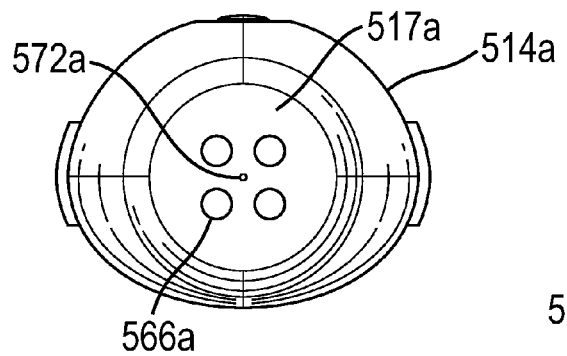
Figure 30B:
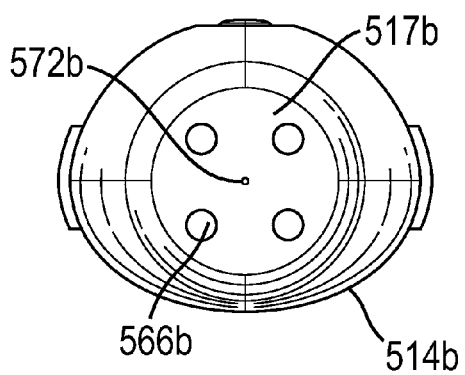
Figure 30C:
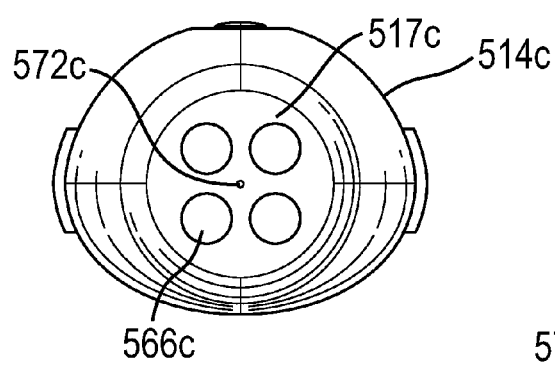
Figure 30D:
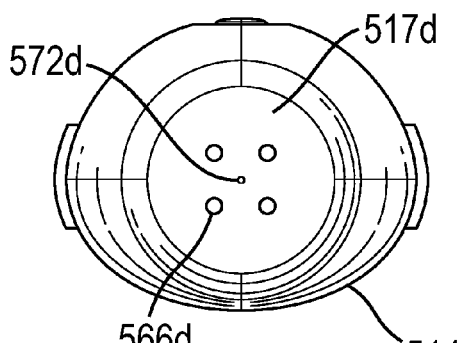
Figure 30E:
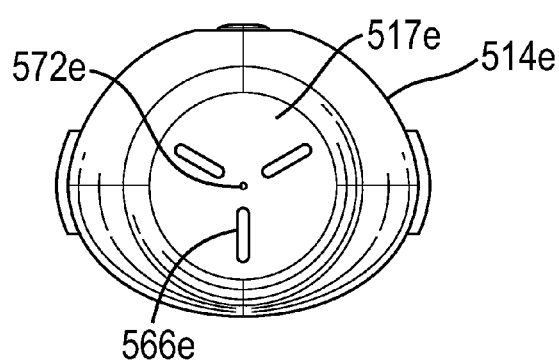
Figure 30F:
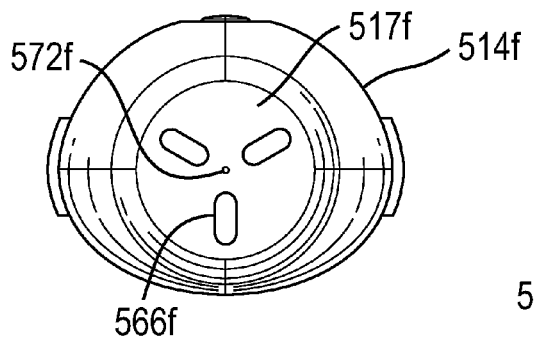
Figure 30G:
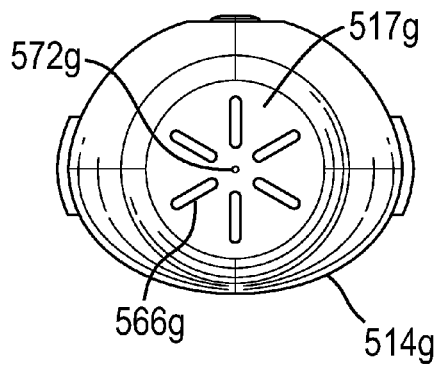
Figure 30H:
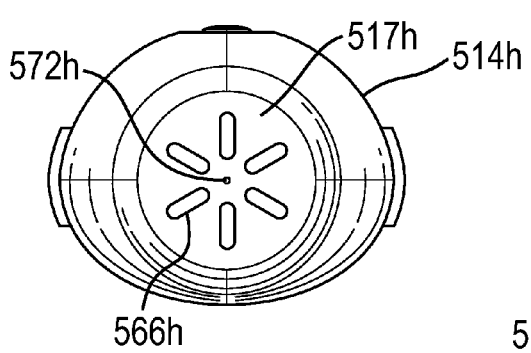
Figure 30I:
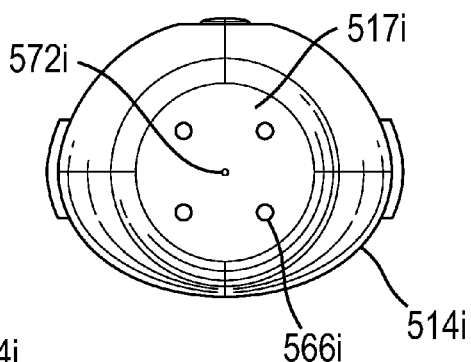
Figure 30J:
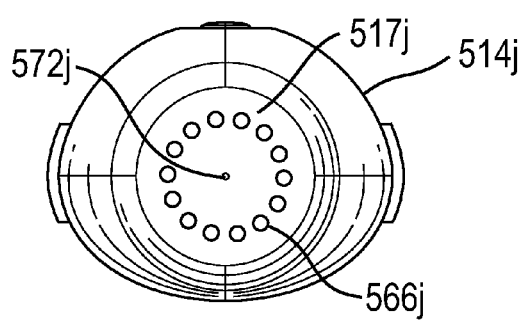
Figure 30K:
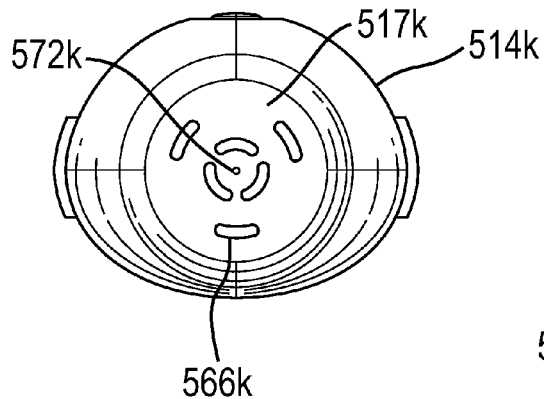
Figure 30L:
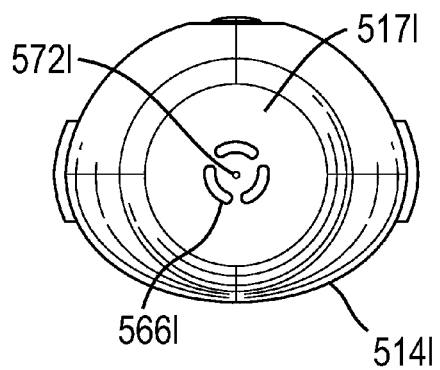
Figure 30M:
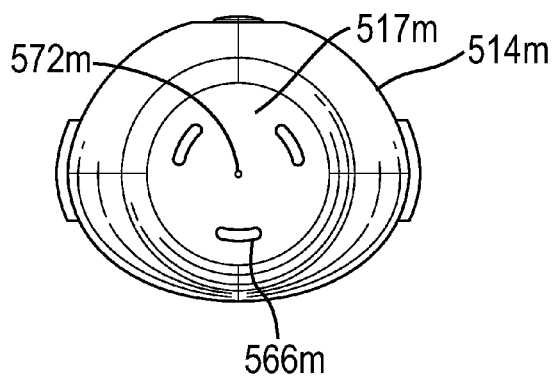
Figure 30N:
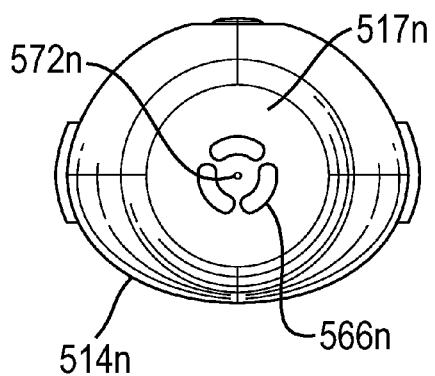
Figure 35B:
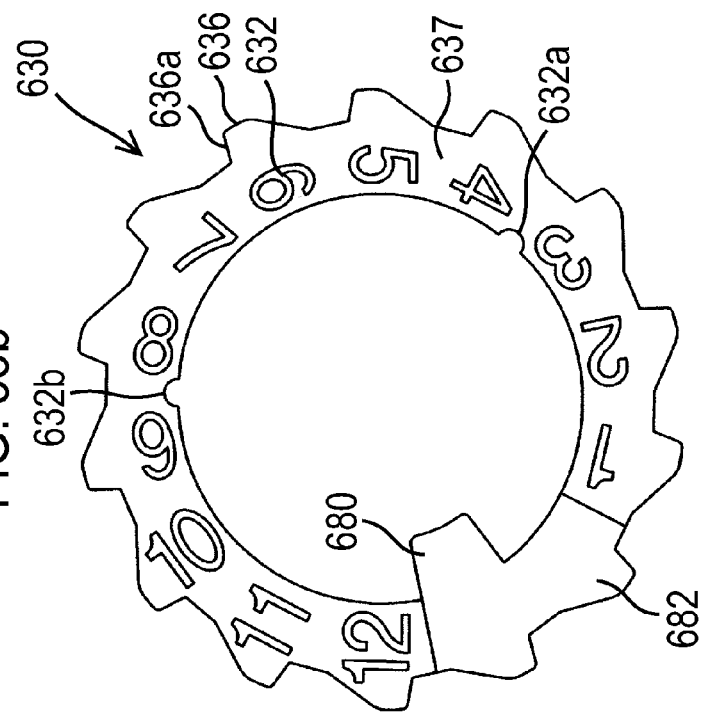
Figure 35A:
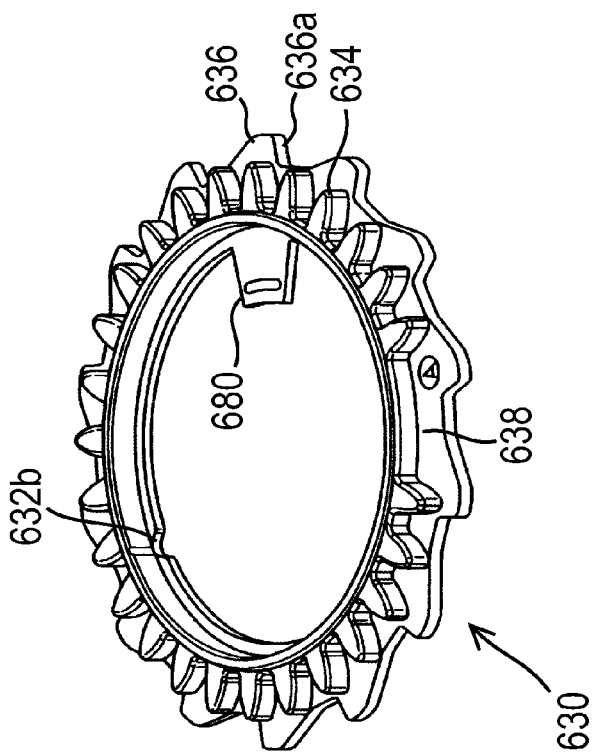
Figure 37B:
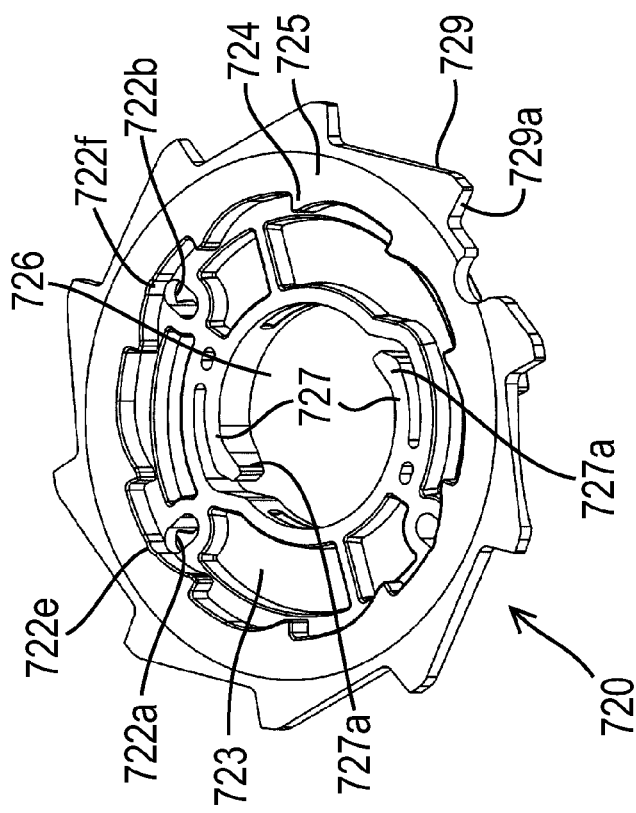
Figure 37A:
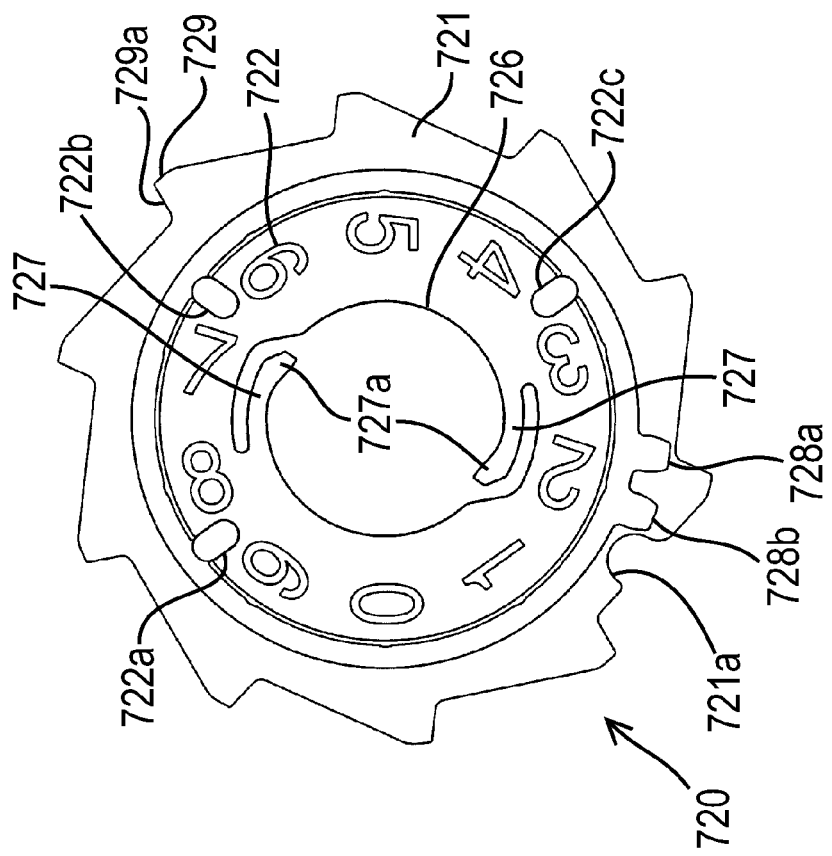
Figure 38B:
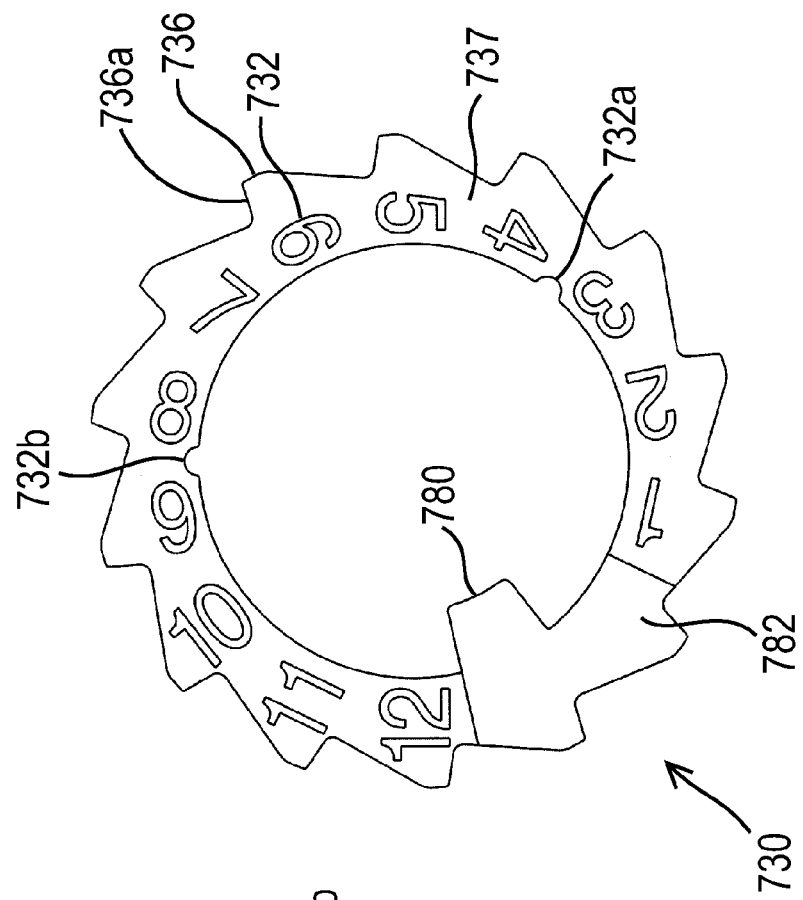
Figure 38A:
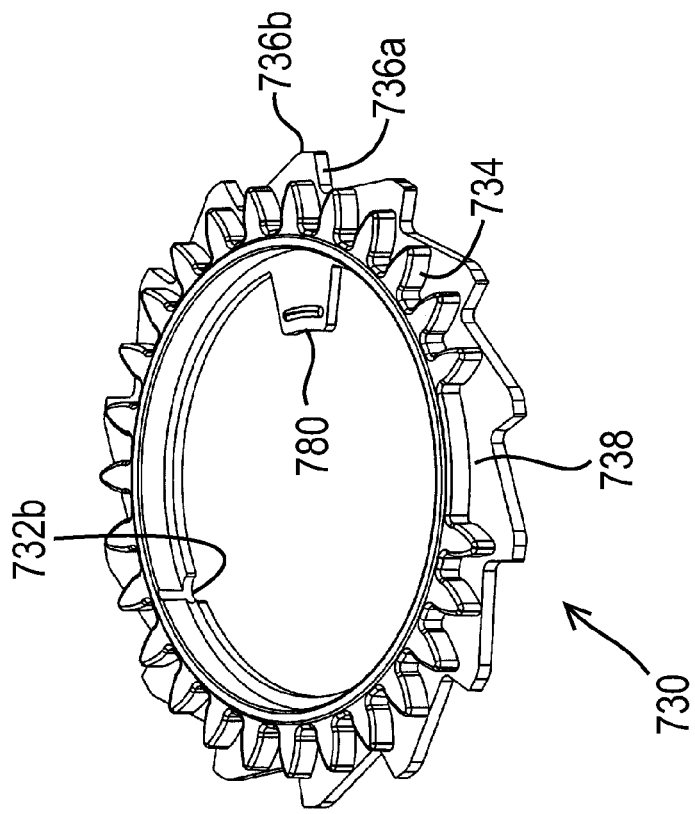

FIGS. 3*a* to 3*b* show front views of the drug dispenser device of FIG. 1 with upper front cover part, actuation counter, driver plate and mouthpiece cover removed and the left lower front cover part and left-side of mouthpiece shown in cut-away section, the device respectively being shown in 'at rest' and first stage of actuation positions;

FIGS. 4*a* to 4*c* show front views of the drug dispenser device of FIG. 1 with upper front cover part, actuation counter, driver plate, mouthpiece cover and left lever removed and the left lower front cover part and left-side of mouthpiece shown in cut-away section, the device respectively being shown in second, third and fourth stages of actuation positions;

FIG. 5 shows an exploded view from the front of part of the internal mechanism of the drug dispenser device of FIG. 1 with driver plate removed;

FIG. 6 shows a schematic view of part of the internal mechanism of the drug dispenser device of FIG. 1 with driver plate removed, and in particular, the 'interlock' mechanism provided to block actuation thereof when the mouthpiece is covered by the mouthpiece cover;

FIG. 7 shows a perspective view of the drug dispenser device of FIG. 1 with the mouthpiece cover removed from the mouthpiece and thus, in a 'ready to use' position;

FIG. 8 shows a perspective view of the drug dispenser device of FIG. 1 with the mouthpiece cover removed from the mouthpiece and the levers depressed and thus in the 'in use' position;

FIG. 9 illustrates a perspective view of a first half of the drug dispenser of FIG. 1 showing air flow into the housing in the 'in use' position thereof;

FIG. 10 illustrates a perspective cut-away view of a second half of the drug dispenser device of FIG. 1 (with actuation counter and details of internal mechanism omitted) showing air flow through the chambers of the housing in the 'in use' position thereof;

FIG. 11 illustrates a perspective cut-away view of a second half of a drug dispenser device that is a slight variation of that drug dispenser device of FIG. 1 (with actuation counter and details of internal mechanism omitted) showing air flow through the inhaler body in the 'in use' position thereof;

FIG. 12 shows an exploded view of an actuation counter herein arranged for receipt within the upper front cover part of the first drug dispenser of FIG. 1 or second drug dispenser device of FIG. 11;

FIGS. 13a and 13b respectively show underside and top views of the actuation counter of FIG. 12 received in the upper front cover part;

FIGS. 14a and 14b show cut-away views of the actuation counter of FIG. 12 at respectively 'count 120' and 'count 119' positions;

FIGS. 15a and 15b respectively show cut-away views corresponding to FIGS. 2514a and 14b of the actuation counter of FIG. 12 absent the decimals count wheel;

FIGS. 16a and 16b respectively show cut-away views corresponding to FIGS. 14a and 14b of the actuation counter of FIG. 12 absent the numerals count wheel;

FIGS. 17a and 17b show cut-away views of the actuation counter of FIG. 12 at respectively 'count_0' and 'shuttered' positions;

FIGS. 18a and 18b respectively show cut-away views corresponding to FIGS. 17a and 17b of the actuation counter of FIG. 12 absent the numerals count wheel;

FIG. 19 shows a front view of the drug dispenser device of FIG. 1 with upper front cover part and actuation counter removed, the device being in the 'at rest' position;

FIG. 20 shows a perspective view of the drug dispenser device of FIG. 1 with the upper front cover part and actuation counter disposed therein shown detached from the remainder of the device, the device being shown in an 'at rest' position;

FIG. 21 shows a plan view of the inner side of the upper front cover part of the drug dispenser device of FIG. 1 and showing the actuation counter disposed therein;

FIGS. 22 and 23 show perspective views of a container collar part for use in an alternative internal mechanism for use with the drug dispenser device herein, as respectively shown in upright and inverted configurations;

FIGS. 24 and 25 respectively show perspective underside and top views of an extension collar part for use in an alternative internal mechanism for use with the drug dispenser device herein;

FIGS. 26a to 26c show perspective views of sequential steps in the assembly of an alternative internal mechanism for use with the drug dispenser device herein, and employing the container collar of FIGS. 22 and 23 and the extension collar of FIGS. 24 and 25;

FIGS. 27a to 27c show sectional side views of interaction of key parts of the container collar of FIGS. 22 and 23 with the extension collar of FIGS. 24 and 25 during sequential operational steps of the alternative mechanism assembled as shown in FIGS. 26a to 26c;

FIG. 28 shows a perspective view from above of the lower housing part and mouthpiece assembly (shown separated) of the drug dispenser device of FIG. 1;

FIGS. 29a and 29b show an alternative 'two part form' lower housing part, as respectively shown separated and as assembled, for use with the drug dispenser device of FIG. 1;

FIGS. 30a to 30n respectively show front views of mouthpiece forms, which may be employed in the drug dispenser devices of FIG. 1 or 11 as an alternative to the mouthpieces thereof;

FIGS. 31a and 31b respectively show back and front views of a driver plate for use with a modified version of the actuation counter of FIGS. 12 to 18b;

FIGS. 32a to 32g and FIGS. 33a to 33g respectively show corresponding plan and perspective views of sequential operation steps of key parts of a modified version of the actuation counter of FIGS. 12 to 18b incorporating the driver plate of FIGS. 31a to 31b;

FIGS. 34a and 34b respectively show perspective underside and top views of a numerals wheel for use in the modified actuation counter of FIGS. 32a to 33g;

FIGS. 35a and 35b respectively show perspective underside and top views of a decimals wheel for use in the modified actuation counter of FIGS. 32a to 33g;

FIGS. 36a and 36b respectively show back and front views of a driver plate for another modified version of the actuation counter of FIGS. 12 to 18b;

FIGS. 37a and 37b respectively show perspective underside and top views of a numerals wheel for use with the drive plate of FIGS. 36a and 36b; and FIGS. 38a and 38b respectively show perspective underside and top views of a decimals wheel for use with the driver plate of FIGS. 36a to 36b.

For the convenience of the reader, in the following description of the illustrated exemplary embodiments of the present invention like reference numerals are used to designate like features in the alternative/different embodiments.

The modified actuation counter, exemplary elements or which are shown at FIGS. 31a to 38b, is in accord with the present invention, whereas the unmodified counter, elements of which are shown at FIGS. 12 to 21, is not in accordance with the present invention.

Turning now to the drawings, FIG. 1 shows a drug dispenser device 1 herein which is in the form of a hand-held, hand-operable, breath coordinated pressurised metered dose inhaler (MDI). This type of device requires a patient to coordinate their inhalation at a dispensing outlet of the device (in this embodiment, a mouthpiece 14) with manual actuation of the device so that the inhalation is coordinated with release of drug from the device so that drug is entrained by the inhalation airflow to the target location in the respiratory tract (in this case, the lungs) of the patient.

The device 1 comprises a housing defined in combination by front 10a and rear 10b upper housing parts and lower housing part 12, all of which are, in this embodiment, formed from plastic (e.g. ABS). It will be noted that the overall form of the housing is arranged for ease of receipt by a user's hand such that in general terms the rear of lower housing part 12 is received by the user's palm. Mouthpiece 14 (not visible in FIG. 1, but see FIG. 7) is protected by removeable mouthpiece cover 16, and extends from the front of lower housing part 12 and is arranged in use, for insertion into the mouth of a patient for inhalation therethrough. The mouthpiece 14 may be made from polypropylene (PP).

A ledge 13a, 13b is provided to the base of the lower housing part 12 such that the device may be arranged to 'stand upright' on the ledges 13a, 13b and mouthpiece cover 16, when cover 16 covers the mouthpiece 14. As will be understood from FIG. 7, when the cover 16 is moved to its 'mouthpiece uncovered' position, the device is able to 'stand upright' on the end face 16a of the cover 16 itself, with the ledges 13a, 13b and mouthpiece cover 16 optionally being provided with releasable complementary connectors, e.g. complementary male and female snap-fit connectors, (not shown) to releasably connect the mouthpiece cover 16 to the ledges 13a, 13b in the position shown in FIG. 7. Such complementary connectors may be respectively provided on the outer surface of the ledges 13a, 13b and the inner surface of the mouthpiece cover 16.

A viewing window 216 is provided to the front upper housing part 10a for viewing of count indicia displayed by (i) a counter 201 locating within that part 10a and described in more detail hereinafter with reference to FIGS. 12 to 21, or (ii) one of the modified counters in accordance with the invention described in more detail hereinafter with reference to FIGS. 31 to 38.

Opposing levers 20a, 20b protrude from apertures 11a, 11b provided to the front 10a and rear 10b upper housing parts. The levers 20a, 20b are shaped such as to respectively accommodate the finger(s) and thumb of a patient in use, thereby facilitating one-handed operation of the device. The levers may be made from ABS.

FIG. 28 shows the lower housing part 12 and mouthpiece 14 (shown separated from each other, in this view) of the drug dispenser device of FIG. 1. Provided to the lower housing part 12 is stem block 8, which is arranged to receive valve stem 7 of an aerosol canister 5 (see also FIG. 2). The stem block 8 also includes a passage 9, which in use acts such as to guide discharged aerosolized drug from the valve stem 7 to the mouthpiece 14. Step portions 18a, 18b, 18c, the purpose of which will be described in more detail in the later description, are also provided to the lower housing part 12.

FIGS. 29a and 29b show an alternative 'two part form' lower housing part 412, as respectively shown separated and as assembled, for use with the drug dispenser device of FIG. 1 as an alternative to the lower housing part 12 of FIG. 28. This two part form comprises lower housing part 412, which is arranged to receive separate stem block part 490. That separate stem block part 490 includes stem block 408 and stem block passage 409. As before, the lower housing part 412 defines step portions 418a, 418b, 418c. During assembly the separate parts 412, 490 are brought together and sockets 494a, 494b, 494c on the stem block part 490 aligned with posts 492a, 492b, 492c on the lower housing part. The parts 412, 490 are then joined to each other by means of heat welding 'heat staking') at each respective post 492a, 492b, 492c to socket 494a, 494b, 494c mating point.

Advantages of using the alternative 'two part form' lower housing part 412 and stem block part 490 assembly are that the precision features of the stem block part 490 are easier to produce and inspect. Additionally, the lower housing part 412 and the stem block part 490 may be made from different plastics/polymer materials (typically by moulding), each material being particularly suited to the particular function(s) of the lower housing part 412 and the stem block 408. The stem block part 490 is generally made from a plastic/polymer selected for ease of drug delivery, and in particular suitable for contact with the drug propellant formulation which will, in use, be discharged through the stem block 408. To this end, polypropylene (PP) may be used to form the stem block part 490, especially when the propellant is HFA-134a or HFA 227 infra. The lower housing part 412, on the other hand, may be formed of ABS or another plastics/polymer material which equally provides rigidity to the step portions 418a, 418b, 418c to thereby facilitate disengagement of flexible support legs 34a, 34b therefrom in actuation of the device 1, as described in more detail hereinafter.

It will be appreciated that the stem block part and lower housing part may have different complementary forms and connections than shown in FIGS. 29a and 29b without departing from the raison d'être for the two-part form for the lower housing part of the device 1.

Figure 2:
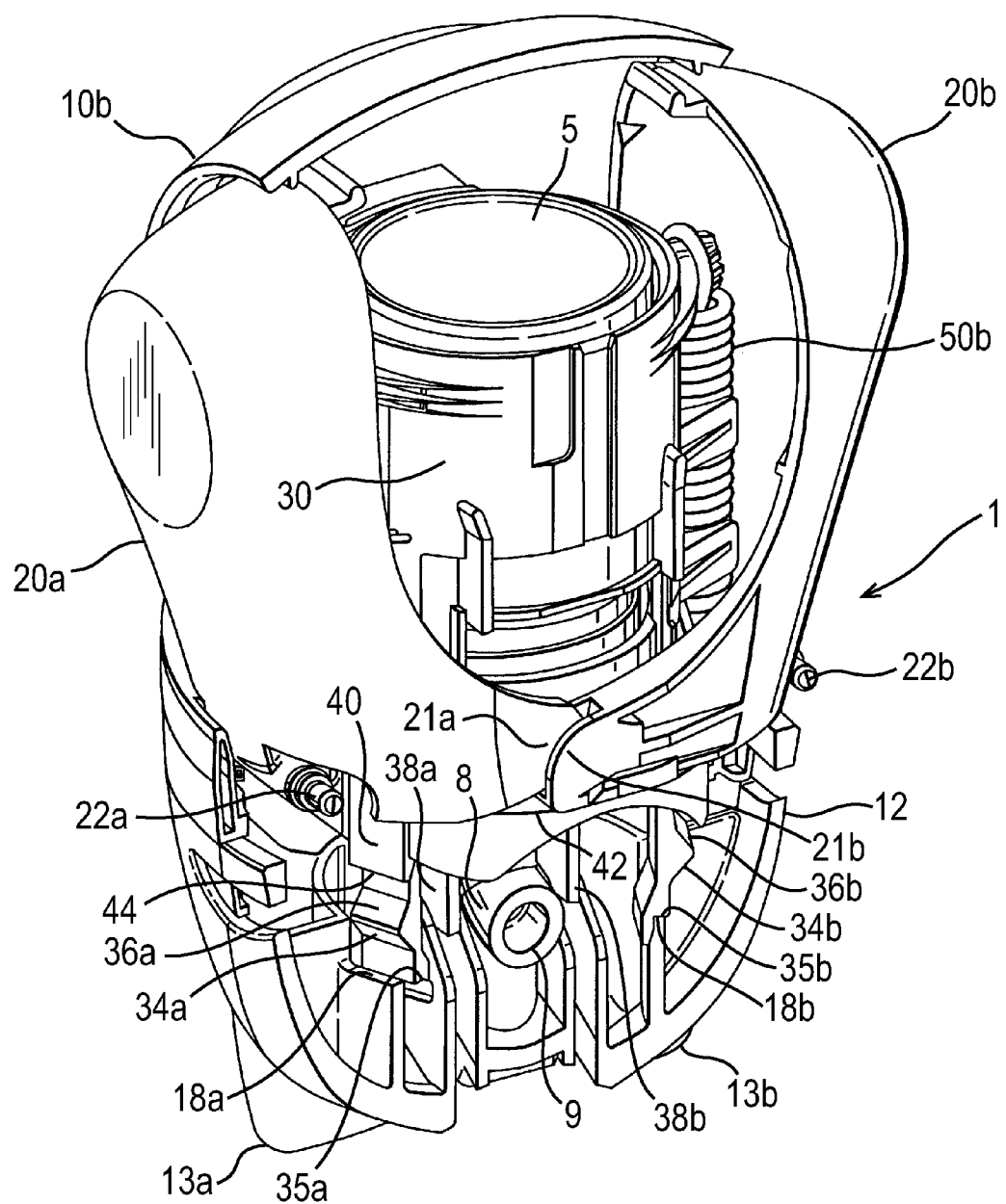
FIG. 2 shows a perspective view of the drug dispenser device of FIG. 1 with upper front cover part, actuation counter, driver plate, mouthpiece and mouthpiece cover removed and the lower front cover part shown in cut-away section, the device again being shown in the 'at rest' position.

Details of the inner workings of the device 1 of FIG. 1 may be appreciated by reference to FIG. 2, in which the upper 10a front housing part and mouthpiece cover 16 have been removed. It will be seen that each opposing lever 20a, 20b pivotally connects to the upper housing part 10a, 10b by means of pivot connector 22a, 22b. The positioning of the pivotal connection is selected to facilitate the desired finger-thumb operability of the levers 20a, 20b by a squeezing movement. It will also be seen that the lower ends 21a, 21b of each lever 20a, 20b mesh together, thereby tending to the couple the motion of each respective lever 20a, 20b one to the other.

Although not shown, each lever 20a, 20b has a lower end 21a, 21b on either side thereof providing a generally U-shape to each lever 20a, 20b at its lower end in plan view.

Provided to the housing, but largely obscured from view by container collar 30, there is provided a drug discharge device, which takes the form of cylindrical valved aerosol canister 5 of the type commonly known for use in an MDI. A valve stem 7 of the drug discharge device is received within the stem block 8 provided to the housing, which stem block 8 includes the passage 9 which acts such as to guide discharged aerosolized drug from the valve stem to the mouthpiece 14.

The levers 20a, 20b are arranged in the device such that the lower ends 21a, 21b of each lever 20a, 20b are disposed on opposing sides (front and rear) of the drug discharge device.

In this particular embodiment, and referring to FIG. 5, the canister 5 has a body 6 made of metal, for instance of stainless steel or, more preferably, of aluminium or an aluminium alloy. The canister contains a pressurised drug aerosol formulation. The formulation comprises the drug (one or more drug actives) and a fluid propellant, and optionally one or more excipients and/or adjuvants. The drug is in solution or suspension in the formulation. The propellant is typically a CFC-free propellant, suitably a liquid propellant, and preferably is a HFA propellant, such as HFA-134a or HFA-227 or a combination thereof. The drug active(s) is typically of the type for use in treatment of a respiratory disease or condition, such as asthma or chronic obstructive pulmonary disease (COPD). The active(s) may also be for prophylaxis or palliation of a respiratory disease or condition.

The canister 5 may have its inner surface coated with a fluorocarbon polymer, optionally in a blend with a non-fluorocarbon polymer, such as a blend of polytetrafluoroethylene and polyethersulphone (PTFE-PES), as disclosed in U.S. Pat. Nos. 6,143,277; 6,511,653; 6,253,762; 6,532,955; and 6,546,928. This is particularly preferred if the drug is in suspension in the formulation, and especially if the suspension formulation is composed only, or substantially only, of the drug and HFA propellant.

The valve stem 7 forms part of a metering valve (not shown) mounted in the canister 5, as will be understood by the skilled person in the art, and as commercially available from manufacturers well known in the aerosol industry, for example, from Valois, France (e.g. DF10, DF30, DF60), Bespak plc, UK (e.g. BK300, BK356, BK357) and 3M-Neotechnic Ltd, UK (e.g. Spraymiser™). The metering chamber of the metering valve may be coated with a fluorinated polymer coating, such as formed from perfluoro-hexane, for instance by cold plasma polymerisation, as detailed in US-A-2003/0101993.

As may be further understood with reference also to FIG. 5, which shows an exploded view of key parts of the internal mechanism, the container collar 30 permanently engages via split-ring collar 33 with the neck 5a of the canister 5 such that the so-engaged parts are moveable together relative to the housing in a direction defined by the longitudinal axis L-L of the canister 5 (i.e. generally up and down when the device 1 is upright). The split-ring collar 33 permanently engages the container collar 30 to the canister 5 as described in U.S. patent application Ser. No. 10/110,611 (WO-A-01/28887) and US-A-2006/0082039, hereby incorporated herein by reference.

The container collar 30 connects via closed coil extension springs 50a, 50b and respective spring connection points 31a, 31b and 41a, 41b to extension collar 40, which is provided at its lower end with a ramp 44. This multi-collar arrangement is such that the extension collar 40 is moveable with respect to the container collar 30 (and hence the canister 5) along the longitudinal axis L-L of the drug discharge device.

The container collar 30, split-ring collar 33 and extension collar 40 may all be made from acetal.

The springs 50a, 50b will typically be formed of metal, for instance stainless steel, such as 302 grade stainless steel.

As shown in FIG. 5, the extension collar 40 includes an actuating portion, in the form of shelf 42, on opposing sides which are arranged for interaction with the lower ends 21a, 21b of the opposing levers 20a, 20b such that when the levers are squeezed together (i.e. inwards relative to the housing) the shelf 42 and hence, extension collar 40 are pushed downwards (i.e. towards the stem block 8).

In this particular embodiment, the levers 20a, 20b have an asymmetric arrangement in that, for each lever 20a, 20b, one of the lower ends (i.e. lower end 21b of lever 20b) extends further towards the other lever than the other lower end, and in this case the longer lower end (i.e. lower end 21b of lever 20b) extends across the central axis H—H of the device 1. Only the longer lower end of each lever 20a, 20b acts on the actuating portion/shelf 42 of the extension collar 40, whereby only one lever 20b acts through its longer lower end 21b on the front side of the actuating portion 42 and only the other lever 20a acts on the rear side of the actuating portion 42 through its longer lower end. As regards the shorter lower ends of each lever 20a, 20b, these link the levers 20a, 20b together at their lower ends, as can be seen most clearly in FIG. 2.

In a modification, however, the levers 20a, 20b may adopt a symmetrical arrangement in which the lower ends 21a, 21b of each lever 20a, 20b have the same extent and both act directly on opposing sides of the actuating portion 42 of the extension collar 40. In this case, the lower ends 21a, 21b would typically not extend across the central axis H-H. The mechanical advantage of this symmetrical arrangement may provide a larger mechanical advantage (e.g. 4:1) than the asymmetrical arrangement (e.g. 1.4-1.5:1). The selection of an asymmetric or symmetric arrangement may depend on various factors, including the force needed to open the valve and/or the spring force of the springs 50a, 50b.

The container collar 30 is further provided with flexible support legs 34a, 34b each of which is provided with a protruding foot 35a, 35b for latching engagement with a respective step 18a, 18b provided to the housing (see FIG. 2). Each leg 34a, 34b also has a shaped head 36a, 36b the purpose of which will become clearer from the later description.

In the 'at rest' position of FIGS. 2 and 3a, each foot 35a, 35b is slightly spaced from its respective step 18a, 18b on the housing. A third flexible support leg (not visible, but associated with third step 18c as visible on FIG. 28) locates at the rear of the container collar (i.e. there are three flexible support legs 34a, 34b). In one embodiment, the two support legs 34a, 34b on either side of the mouthpiece 14 are spaced at 113.4° intervals relative to a third support leg (not visible) which locates rearwards to the mouthpiece 14.

The container collar 30 is further provided with downward protrusions 38a, 38b, the purpose of which will become clear from the later description.

In general operational terms, referring now also to FIG. 3a, the opposing levers 20a, 20b are moveable transversely with respect to the longitudinal axis L-L of the drug discharge device to apply a force to the shelf 42 of the extension collar 40 to move the extension collar 40 downwards along that longitudinal axis (i.e. towards stem block 8 and mouthpiece 14).

The closed coil extension springs 50a, 50b that connect the container collar 30 via connector points 31a, 31b with the extension collar 40 act as a biasing mechanism to store biasing energy on moving the extension collar 40 downwards along the longitudinal axis L-L in response to squeezing of the levers 20a, 20b. In embodiments, an initial biasing tension—inherent in the closed coil form thereof—is present in the closed coil extension springs 50a, 50b even when in their 'at rest' state.

The flexible support legs 34a, 34b act to provide a pre-load mechanism to prevent transfer of that biasing energy to the container collar 30 to move the canister 5 downwards along the longitudinal axis L-L to actuate the valve 7 thereof (and hence, to fire the aerosolized drug dose) until a pre-determined threshold force is overcome.

Further details of the operation of the device 1 (which results from an effective user actuation thereof) may be appreciated by making reference to FIGS. 3a to 4c, in which for clarity only selected parts relevant to the particular stage of operation represented are labelled.

FIG. 3a shows how the device 1 is configured in the 'at rest' position, in this instance also with the mouthpiece 14 covered by the mouthpiece cover 16. The levers 20a, 20b are splayed apart and catch retainers 24a, 24b provided to an inner part of the protruding end 23a, 23b of each respective lever 20a, 20b locate close to 'stop' positions defined by notches 15a, 15b provided to the top parts 10a, 10b of the housing. The lower ends 21a, 21b of each lever 20a, 20b seat against the shelf 42 of the extension collar 40 but no force acts on the extension collar 40. The closed coil extension springs 50a, 50b are therefore in their 'at rest' state with no externally-applied (i.e. by lever 20a, 20b actuation) biasing energy stored therein (but only any initial biasing tension—inherent in the closed coil form of the extension springs 50a, 50b—present). Each foot 35a, 35b of the flexible support legs 34a, 34b is slightly spaced from its respective step 18a, 18b on the housing.

In FIG. 3b, the device is shown at a first early stage of operation, after removal of the mouthpiece cover 16 from the mouthpiece 14, in which the levers 20a, 20b have been squeezed very slightly together. The lower ends 21a, 21b of each lever 20a, 20b push slightly down on the shelf 42 of the extension collar 40 such that the extension collar 40 is moved slightly downwards. That downwards movement of the extension collar 40 is transferred via the extension springs 50a, 50b to the container collar 30, which also moves slightly downwards. Importantly, this downwards movement of the container collar 30 brings each foot 35a, 35b of the flexible support legs 34a, 34b into latching engagement with its respective step 18a, 18b on the housing. As a result of this latching engagement, further downwards movement of the container collar 30 is impeded.

In FIG. 4a, the device is shown at a second stage of operation, in which the levers 20a, 20b have been squeezed further together. The lower ends 21a, 21b of each lever 20a, 20b push further down on the shelf 42 of the extension collar 40 such that the extension collar 40 is moved downwards. That downwards movement of the extension collar 40 however, cannot now be transferred via the extension springs 50a, 50b to the container collar 30 because of the latching engagement of each foot 35a, 35b of the flexible support legs 34a, 34b with its respective step 18a, 18b on the housing. That latching engagement impedes the downwards movement of the container collar 30. The downwards movement of the extension collar 40 therefore results in the extending of each closed coil extension spring 50a, 50b, thereby resulting in biasing energy being stored in the now-extended springs 50a, 50b.

In FIG. 4b, the device is shown at a third stage of operation, in which the levers 20a, 20b have been squeezed even further together. The lower ends 21a, 21b of each lever 20a, 20b push even further down on the shelf 42 of the extension collar 40 such that the extension collar 40 is moved even further downwards. That further downwards movement of the extension collar 40 still cannot now be transferred via the extension springs 50a, 50b to the container collar 30 because of the latching engagement of each foot 35a, 35b of the flexible support legs 34a, 34b with its respective step 18a, 18b on the housing. The further downwards movement of the extension collar 40 therefore results in further extension of each extension spring 50a, 50b, thereby resulting in further biasing energy being stored in the now well-extended springs 50a, 50b.

Further, in the position shown in FIG. 4b, ramps 44 provided to the extension collar 40 respectively engage with the shaped heads 36a, 36b of the flexible legs 34a, 34b and act on the already-tensed flexible legs 34a, 34b such that each foot thereof 35a, 35b is at the point of becoming displaced from its respective step 18a, 18b. In essence, the ramp 44 acts to 'guide' the displacement action. Thus, FIG. 4b corresponds to the position at which the latching engagement of the flexible legs 34a, 34b with their steps 18a, 18b is just about to be overcome for release of the biasing energy stored in the extension springs 50a, 50b. This position therefore corresponds to the threshold (or 'tipping point') of the pre-load/stored biasing energy system defined by the components of the device. Applying any further squeeze force to the levers 20a, 20b will result in that threshold being exceeded, and effective user actuation of the device 1.

Conveniently, the device 1 is adapted such that the threshold is exceeded only by the user applying at least a total grip force of 15 to 25N, more conveniently 20-25N, to the levers 20a, 20b. In other words, this is the minimum total grip force that the user needs to apply for actuation of the device 1. In practice, this would typically means applying half the total grip force to each lever 20a, 20b or all the total grip force to one lever 20a, 20b (noting that the levers 20a, 20b are coupled so that movement of one causes movement of the other). However, the total grip force could also be applied by other unequal application of forces to the levers 20a, 20b. Of course, the actual pre-load threshold force for unlatching the collar legs 34a, 34b and releasing the stored energy in the springs 50a, 50b would be greater than the minimum total grip force due to the use of a pair of levers 20a, 20b which each provide a mechanical advantage. This makes it easier for the user to "fire" the device 1 than would otherwise be the case, although not so easy to "fire" unintentionally.

In FIG. 4c, which corresponds to a fourth stage of operation, such further force has been applied to the levers 20a, 20b. The protruding end 23a, 23b (see also FIG. 3a) of each respective lever 20a, 20b touches off one against the other, thereby preventing any further lever 20a, 20b travel. Most importantly, the flexible legs 34a, 34b have become displaced from their respective steps 18a, 18b through the action of the ramps 44. The container collar 30 may now move freely downwards and indeed, will do so as a result of its experience of the biasing energy stored in the extension springs 50a, 50b. The container collar 30 and canister 5 in permanent engagement therewith move rapidly downwards propelled by the stored biasing energy of the springs 50a, 50b. The valve of the canister 5 is thereby opened to release aerosolized drug through the passage 9 in the stem block 8 which guides that discharged aerosolized drug to the mouthpiece 14 for inhalation by the patient.

It will be appreciated that once the threshold force has been overcome (i.e. just past the 'tipping point' of the device) a uniform actuating force resulting from the energy stored in the springs 50a, 50b is experienced by the container collar 30 and canister 5 regardless of how much extra force is applied by the patient to the levers 20a, 20b. A consistent actuation (opening) of the valve 7 of the canister 5 is thereby, enabled by the configuration of the device 1.

The springs 50a, 50b are adapted to store sufficient energy therein as to overcome the force for opening the metering valve 7 when released. For a typical standard force of approximately 40N for opening a MDI metering valve, each spring would be configured to produce an equal force which is marginally greater than one-half the metering valve opening force. If a 55N force was needed to open the metering valve 7, each spring may be selected to produce a nominal 29N force.

Following actuation, the coiled coil extension springs 50a, 50b return to their 'at rest' state (i.e. with no externally-applied biasing energy, but only any initial biasing tension inherent in the closed coil form of the extension springs 50a, 50b present). As will be appreciated by the skilled reader in the art, the return spring (not shown) of the valve of the valved canister provides energy to move the canister 5, container collar 30, extension collar 40 and levers 20a, 20b back to the 'at rest' position as shown in FIG. 2. Further actuating operations may therefore be conducted until the canister 5 is exhausted of its drug formulation contents.

FIG. 6 shows a particular detail of the first drug dispenser device of FIGS. 1 to 5. For succinctness, only those parts relevant to this detail are now described further.

As previously described, the container collar 30 is provided at its underside with two downward protrusions 38a, 38b. The mouthpiece cover 16 is further provided with P-shaped cam interference elements 17a, 17b joined together by bridge element 18 and joining to the mouthpiece cover 16 by means of living hinge 19 about which the bridged interference elements 17a, 17b may pivot. When, as shown in FIG. 6, the mouthpiece cover 16 engages with the body 12 of the dispenser device 1 to close the mouthpiece 14 (i.e. in the mouthpiece-closed position) the interference elements 17a, 17b adopt a position in which they locate underneath the downward protrusions 38a, 38b in close proximity or abutment therewith to thereby prevent any downward movement of the container collar 30. See also FIG. 3a. Unintended movement of the container collar 30, and hence unintended actuation of the dispenser device 1, is prevented.

In a subtle point, it is noted that when the mouthpiece cover 16 is in place such that the interference elements 17a, 17b prevent the downward movement of the container collar 30, the levers 20a, 20b, extension springs 50a, 50b, and extension collar 40 are not locked and are therefore free to move. The levers 20a, 20b may thus still be compressed to the point at which their protruding ends 23a, 23b touch off, but without any movement of the container collar 30 and actuation of the dispenser device 1. When the protruding ends 23a, 23b are so touched off the user will also not be able to apply further, potentially damaging, force to the interference elements 17a, 17b or to the stem block 8.

The relative positioning of the interference elements 17a, 17b and the collar protrusions 38a, 38b in the various stages of operation of the device 1 is shown in FIGS. 3 and 4. FIG. 3a shows the spatial relationship when the mouthpiece cover 16 is in the mouthpiece-closed position, whilst FIGS. 3b and 4a-4c show the spatial relationship with the cover 16 removed and the levers being depressed inwardly to fire the device 1.

The mouthpiece cover 16 may take one of the particular forms described in U.S. patent application Ser. No. 12/066,048, derived from PCT Patent Application No. WO-A-2007/028992, which claims priority from UK patent application No. 0 518 355 filed 8 Sep. 2005, the entire content of which applications are incorporated herein by reference.

A modified mouthpiece cover which may be used in place of the mouthpiece cover 16 is disclosed with reference to FIGS. 38 to 40 of WO-A-2008/110584 which designates the United States of America, the content of which Application, and any subsequent US(PCT) Patent Application derived therefrom, is hereby incorporated herein by reference. It will be appreciated that this modified mouthpiece cover is also suitable for use in the drug dispenser device 101 of FIG. 11.

FIGS. 7 to 10 illustrate aspects of the air flow into and through the housing of the drug dispenser device of FIG. 1 during use thereof. For succinctness, only those parts of the drug dispenser relevant to these aspects are now described.

FIG. 7 shows the drug dispenser device 1 of FIG. 1 in a 'ready to use' position with the mouthpiece cover 16 removed from the mouthpiece 14. It will be noted that in this position, the mouthpiece cover 16 is pivoted to a position underneath the lower housing part 12. The opposing levers 20a, 20b, which protrude from apertures 11a, 11b provided to the front 10a and rear 10b upper housing parts, are in their rest position. It will also be noted that in this position, the opposing levers 20a, 20b act to block off the apertures 11a, 11b such as to prevent ingress of dirt particles or other debris into the body of the device 1.

FIG. 8 shows the drug dispenser device 1 of FIG. 1 in the 'in use' position, in which the opposing levers 20a, 20b have been moved towards each other, typically in response to a patient finger and thumb squeezing action. In this position, the opposing levers 20a, 20b no longer act to block off the apertures 11a, 11b such that air 60a, 60b may flow through the opened up apertures 11a, 11b into the upper housing part 10a, 10b in response to patient inhalation 61 through the mouthpiece 14.

The air flow 'in use' through the device 1 is now described in more detail with reference to FIGS. 9 and 10.

FIG. 9 shows one half of the device 1 of FIG. 1 in the 'in use' position, in which the mouthpiece 14 is revealed, and in which lever 20b has been pushed inwards to open up aperture 11b. External air 60b may thus, now be drawn into the body of the device housing through this aperture 11b (and also similarly through aperture 11a on the other side) in response to patient inhalation 61 through the mouthpiece 14. In other words, the patient coordinates their inhalation 61 at the mouthpiece 14 to depression of the levers 20a, 20b so that the resulting airflow through the housing 10a, 10b, which enters via the opened apertures 11a, 11b and exits through the mouthpiece 14, is coincident with the release of the drug from the canister 5 caused through actuation of the levers 20a, 20b. The airflow thus entrains the drug into the respiratory tract of the patient.

FIG. 10 illustrates in more detail, the air flow 60a, 62 through the body of the device 1 during use thereof (i.e. again with the device 1 in the 'in use' position of FIGS. 8 and 9).

Referring to FIG. 10 in more detail, the device 1 may be seen to comprise a discharge assembly in the form of a stem block assembly 3 which is integrally formed with the lower body part 12 and provides for the delivery of an aerosol spray of a drug on actuation of the inhaler. Mouthpiece 14 is a separately formed part which is fitted to the lower body part 12 (see FIG. 28) and in use is gripped in the lips of the user to facilitate oral inhalation. Received within the enclosed chamber defined by the housing parts 10a, 10b, 12 there is provided aerosol canister 5 which contains drug to be delivered on actuation of the inhaler and is fitted in the main body and fluidly connected to the stem block assembly 3.

The mouthpiece 14 comprises an external section 15 which is configured to be gripped in the lips of a subject and defines a substantially cylindrical, open forward end through which an aerosol spray of a drug is in use delivered on actuation of the inhaler, an essentially 'bucket-shaped' open chamber form internal section 17 which has a closed rear section (other than air holes 66 and spray orifice 72 described hereinafter), and a discharge outlet in the form of a nozzle outlet 70 which is coupled to a rear end of the internal section 17, such as to provide for the delivery of an aerosol spray 64 into and through the internal section 17.

In response to patient inhalation, air 60a is drawn down the rear part 10b of the body of the device 1 past around the stem block assembly 3 and towards the rear of the internal section 17 of the mouthpiece 14, which is provided with a duality of slot-like air holes 66 at the rear (i.e. base of the 'bucket') thereof arranged about spray orifice 72. The air holes 66 may be equi-spaced from the spray orifice 72. As may be seen, when the air 60a is drawn through these dual air holes 66a duality of air flows 62 is defined within the mouthpiece 14. This provides for a partly annular air flow at the inner peripheral surface of the mouthpiece 14, which partly sheaths the aerosol spray 64 as delivered from the spray orifice 72 of the nozzle outlet 70, thereby partly entraining the aerosol spray 64 and reducing deposition at the internal surface of the mouthpiece 14.

In this embodiment the rear of the internal section 17 has a generally flat shape, which forms the base of the 'bucket'. The edges of the base curve outwards such that the internal section 17 has an increasing internal dimension in a direction away from the stem block assembly 3.

The nozzle outlet 70 includes the spray orifice 72 which provides for the delivery of an aerosol spray through the internal section 17 of the mouthpiece 14 and a delivery channel 74 which fluidly connects the delivery passage 9 of the stem block assembly 3 to the spray orifice 72.

In this embodiment the delivery channel 74 is a tapering channel which narrows towards the spray orifice 72. In this embodiment the delivery channel 74 has straight wall sections.

In this embodiment, the stem block assembly 3 comprises the stem block 8 for receiving the valve stem 7 of the canister 5, and the nozzle outlet 70 of the mouthpiece 14 which fluidly connected to the stem block 8, such as to provide for the delivery of an aerosol spray through the mouthpiece 14. The stem block 8 may be integrally formed with the lower body part 12.

The stem block 8 includes a tubular bore 76 for receiving the valve stem 7 of the canister 5, which in this embodiment is co-axial with the longitudinal axis H-H of the housing (FIG. 3a), which housing axis H-H in this embodiment is coincident with the longitudinal axis L-L of the drug discharge device when mounted in the drug dispenser device 1. The tubular bore 76 is open at one, the upper, end thereof and includes an upper section 77 which has an internal dimension which is substantially the same as the outer dimension of the valve stem 7 of the canister 5 and a lower section 78 which has a smaller dimension, which sections 77, 78 together define an annular seat for the distal end of the valve stem 7.

In this embodiment, the stem block 8 includes a lateral cavity 80 which slidingly receives the nozzle outlet 70 of the mouthpiece 14 and is fluidly connected to the tubular bore 76 thereof. The nozzle outlet 70 is configured to be a tight friction fit in the lateral cavity 80 in the stem block 8. Desirably, the tight friction fit provides a gas-tight seal. In other embodiments, other types of sealing method, also preferably arranged to provide a gas-tight seal, may be employed.

With this configuration of the stem block assembly 3, the nozzle outlet 70 (or mouthpiece 14) and the nozzle block 8 (or lower housing part 12) can be formed of different materials and to different specifications which are specifically suited to their purposes.

FIG. 11 shows a variation 101 of the drug dispenser device of FIGS. 1 to 10, with like features being identified with like reference numerals. The device 101 of FIG. 11 is identical to the embodiment of FIGS. 1 to 10 in all aspects other than that the dual horizontal slot-like air holes 66 visible in FIG. 10 are replaced by an arrangement of four circular air holes 166 (only three visible in FIG. 11) about the spray orifice 172 at the rear (i.e. base of the 'bucket') of the internal section 117 of the mouthpiece 114. It may be seen that the four air holes 166 are arranged in a generally circular arrangement about the spray orifice 172, in this embodiment being at 90° angular displacement relative to each other. The spray orifice 172 may be centrally located in the circular arrangement of the air holes 166. As may be seen in FIG. 11, when external air 160*a* is drawn through these plural spaced air holes 166 a plurality of air flows 162 is defined within the mouthpiece 114. This provides for an essentially annular air flow at the inner peripheral surface of the mouthpiece 114, which essentially sheaths the aerosol spray 164 as delivered from the spray orifice 172 of the nozzle outlet 170, thereby entraining the aerosol spray and reducing deposition at the internal surface of the mouthpiece 114.

FIGS. **30*a* to 30*n* show other mouthpiece forms 514*a* to 514*n*, which may be employed in the drug dispenser device of FIGS. 1 and 11 as an alternative to the mouthpieces 14, 114 thereof. These alternative mouthpiece forms 514*a* to 514*n* differ only in the size, shape and number of respective air holes 566*a* to 566*n* provided to the rear of the internal section 517*a* to 517*n* of these alternative mouthpiece forms 514*a* to 514*n*, which air holes 566*a* to 566*n* are as before, arranged about a spray orifice 572*a* to 572*n***.

Thus, FIGS. **30*a* to 30*d* and 30*i* show different arrangements of four circular air holes 566*a* to 566*d* and 566*i*; FIGS. 30*e* and 30*f* show different arrangements of three slot-like air holes 566*e*, 566*f*; FIGS. 30*g* and 30*h* show different arrangements of six slot-like air holes 566*g*, 566*h*; FIG. 30*j* shows an arrangement of many circular air holes 566*j*; FIG. 30*k* shows an arrangement of six curved slot air holes 566*k* arranged in two concentric rings; FIGS. 30*l* to 30*n* show different arrangements of three curved slot air holes 566*l* to 566*n*** arranged in a ring pattern.

FIGS. 36 and 37 of WO-A-2008/110584 supra show yet further alternative mouthpiece forms which may be employed in the drug dispenser device of FIGS. 1 and 11 as an alternative to the mouthpieces 14, 114 thereof.

Other air flow pathways through the drug dispenser device are possible, for instance such as those described in U.S. Provisional Application No. 60/823,146 filed on 22 Aug. 2006 and International (PCT) Patent Application PCT/EP2007/058670 (WO-A-2008/023014) supra, the contents of which Applications, and any subsequent US (PCT) Patent Application derived from the PCT Application, are hereby incorporated herein by reference.

The upper front part **10*a* of the drug dispenser device 1, 101 of FIGS. 1 and 11 is arranged for receipt and housing of an actuation counter 201. FIGS. 12 to 18*b* provide details of the workings of a suitable actuation counter 201. FIGS. 19 to 21 show more details of the interaction of the actuation counter with the actuating mechanism of the drug dispenser device 1, 101**.

Referring now to FIG. 12, this shows an actuation counter 201 for use with the drug dispenser device 1, 101 herein. FIGS. **13*a* and 13*b* respectively show underside and top views of the actuation counter 201. The actuation counter 201** is of the form disclosed in Applicant's U.S. patent application Ser. No. 10/597,551 derived from International (PCT) Patent Application WO-A-2007/104964, the contents of each of which are incorporated herein by reference.

The actuation counter 201 is comprised within upper front part **10*a* of the drug dispenser device 1 (or 101) which provides first 212 and second 214 spindle mountings, each capable of defining an axis of rotation and a circumferential wall 218 defining a bezel form retainer 219. A viewing window 216 is provided to the housing to enable the viewing of the count. As will be understood by a comparison of FIG. 1 with FIG. 13*b*, the oval-shaped front face 101 of the upper front part 10*a* is covered with a correspondingly shaped label 103 (e.g. of a polymeric material) to cover the apertures in the front face 101 shown in FIG. 13*b*, but not the viewing window 216. In other words, the label has an aperture 105 which registers with the viewing window 216. In an alternative embodiment, the label 103 may itself have a transparent portion in place of the aperture 105 to enable observation of the viewing window 216**.

Now describing the workings of the actuation counter in more detail: First, disc-shaped count wheel 220 has 'units' (i.e. numerals) count indicia 222 provided at spaced intervals on a top face thereof. The first count wheel 220 is provided with a central aperture 226 and a circular cavity 223 that is arranged for disposed receipt of ratchet wheel 250. Ratchet drive receipt teeth 224 are arranged about the inner circumferential wall 225 of the cavity for ratcheted drive interaction with the ratchet wheel 250. The ratchet wheel 250 itself, is sized and shaped for receipt by the circular cavity 223 of the first count wheel 220 and is provided with two oppositely-located drive tongues **252*a*, 252*b* for ratcheted drive interaction with the ratchet drive receipt teeth 224. The ratchet wheel 250 is also provided with a drive-receiving protrusion 254 arranged in use, for drivable rotation of the ratchet wheel 250**.

As will be described in more detail hereinafter with reference to FIGS. 19 to 20, the drive-receiving protrusion 254 receives drive in response to drive interaction with downward drive slot 82 provided to driver plate 80 in which the drive-receiving protrusion 254 is located. The driver plate 80 is permanently fixed to the container collar 30 so as to move in tandem/unison therewith. In this embodiment, the driver plate 80 is permanently fixed to the container collar 30 by ultrasonic welding.

Noting that the driver plate 80 moves on a linear path (along axis L-L) on actuation of the drug dispenser device 1, 101 and that the ratchet wheel 250 rotates, the drive slot 82 allows for the transverse component of motion of the drive-receiving protrusion 254 therein as the ratchet wheel 250 rotates upon the drive-receiving protrusion 254 being driven by the drive slot 82.

Second, ring form count wheel 230 also has 'tens of units' (i.e. decimals) count indicia 232 provided at spaced intervals on a top face 237 thereof and a set of teeth 234 provided in annular arrangement to the underside thereof. It may be noted that at stop position 238, two of the teeth 234 have been removed and further that the outer circumferential edge of top face 237 is formed with a series of equally spaced notches or indentations 236. The reasons for these features will become clear from the later description. The second count wheel 230 is also provided with a protruding shutter 280, the function of which will also be described later.

Kick wheel 240 has kick teeth 244 provided in annular arrangement around the circumference thereof.

As may be best seen at FIG. 13a, when assembled, second count wheel 230 is received for rotation within the bezel form retainer 219 of the housing; and first count wheel 220 is received within the inner ring void 235 defined by ring-shaped second count wheel 230 and its central aperture 226 by first spindle 212 such that clearance exists between the first 220 and second 230 count wheels. Thus, the first 220 and second 230 count wheels are in concentric relationship, but the level of the second count wheel 230 is slightly raised relative to that of the first count wheel 220 to enable shutter 280 to protrude over and above the first count wheel 220. Ratchet wheel 250 is received within the circular cavity 223 of the first count wheel 220 such that drive tongues 252a, 252b engage with the ratchet drive receipt teeth 224. Both wheels 220, 230 and the ratchet wheel 250 are rotatable about a common first axis of rotation F-F defined by the axis of first spindle 212. The drive-receiving protrusion 254 is offset from the first axis F-F, as is the drive slot 82. Moreover, the protrusion 254 and drive slot 82 are both offset to the longitudinal axis L-L.

Kick wheel 240 is received by second spindle 214 for rotation about a second axis of rotation S-S defined by the second spindle 214 and therefore offset from the first axis of rotation F-F. It will be appreciated that the second axis of rotation S-S is spaced from the first axis of rotation F-F to be outside the path of rotation defined by the outwardly-facing teeth 234 of the second count wheel 230. Moreover, the first and second axes F-F, S-S are parallel, or substantially parallel, to each other.

The set of kick teeth 244 of the kick wheel 240 are in meshed relationship with the set of teeth 234 of the second count wheel 230 such that rotary motion of the kick wheel 240 results in rotary motion of the second count wheel 230. In turn, ratchet drive tongues 252a, 252b of ratchet wheel 250 mesh with the ratchet drive receipt teeth 224 of the first count wheel 220 for drivable rotation of the first count wheel 220.

As will be described in more detail hereinafter, when the actuation counter 201 is disposed in the drug dispenser 1,101, the ratchet wheel 250 is in turn drivably rotatable about the first axis F-F by the drive-receiving interaction of protrusion 254 with downward drive slot 82 provided to driver plate 80. The driver plate 80 fixes to the container collar 30, which is itself drivable downwards in response to effective user actuation of the drug dispenser device 1, 101.

First count wheel 220 may also be seen to be provided at its periphery with a pair of fixed index teeth 228a, 228b (as may be best seen in FIG. 15a) arranged for intermittent meshing with the kick teeth 244 of the kick wheel 240 such that rotary motion of the kick wheel 240 results from rotary motion of the first count wheel 220 only when said intermittent meshing occurs.

In a subtle aspect, it may be seen that the profile of certain teeth 234, 228a, 228b, has a flanged form, which is selected to optimise the various toothed engagements necessary for effective gearing and inter-operability of the parts of the counter.

In a further subtle aspect, the counter 201 is arranged to count down from '120' to a 'shuttered position'. The second count wheel 230 is thus, arranged to define fourteen equal pitches allied to twenty-six (calculated as (2×14)−2) teeth 234 plus two missing teeth at stop position 238. The number of pitches is defined as x+2, wherein x is the highest numeral on the second count (i.e. decimals) wheel, which in turn corresponds to a highest count of 10 times x (i.e. 10×12=120, in this embodiment). The '+2' part of the sum determining the number of pitches relates to one coloured portion 282 and one shutter portion 280, as are described in more detail later.

Overall, it may be noted that the actuation counter 201 has a relatively compact form to assist its receipt within the upper front housing part 10a of the drug dispenser device 1, 101. In particular, the counter 201 extends upwards in the direction of the axes F-F, S-S to only a minor extent.

Operation of the actuation counter 201 is now described with additional reference to FIGS. 14a to 16b, in which only the most relevant features to the described operation are labelled. The actuation counter 201 is arranged to count down and thus, to illustrate a count operation, FIGS. 14a, 15a and 16a show the actuation counter 201 at a 'count 120' position and FIGS. 14b, 15b and 16b show the actuation counter 201 at a 'count 119' position (i.e. just after counting down from 120).

It will be appreciated that the 'count' of the dose counter 201 referred to herein is the count number collectively presented by the count wheels 220, 230 in the window 216.

To initiate a general count operation, ratchet wheel 250 is rotated in response to effective user actuation of the drug dispenser device 1, 101 by squeezing the levers 20a, 20b together as described with reference to FIGS. 1 to 7 above. This results in the drive slot 82 driving the ratchet wheel protrusion 254 to rotate the ratchet wheel 250 in a first rotary sense (clockwise in FIGS. 12 and 13a). This, in turn, results in rotation of the first count wheel 220 in the first rotary sense by the meshed interaction of drive tongues 252a, 252b with ratchet drive receipt teeth 224. The ratchet wheel 250 and first count wheel 220 are configured and arranged such that when indexed first count wheel 220 rotates by 36° such that a single indicium 222 thereon is advanced (i.e. the 'units' count moves down one unit).

Where the pre-count operation visible count is x0 (e.g. 120 with 'x=12', as shown at FIGS. 14a, 15a and 16a), the counting action resulting from the use operation is subtly different. Once again, ratchet wheel 250 is rotated in response to effective user actuation of the drug dispenser device 1, 101 causing rotation of the first count wheel 220 by 36° such that the 'unit' indicium 222 moves on from '0' to '9' (as shown at FIGS. 14b and 15b). This rotation of the first count wheel 220 however, also brings the pair of index teeth 228a, 228b into meshed relationship with the kick teeth 244 of kick wheel 240 such that the kick wheel 240 rotates and in turn, causes the second count wheel 230 to rotate through meshing of their respective teeth 234, 244. The wheels 220, 230, 240 are configured and arranged such that the resultant rotation of the second count wheel 230 is by 360/14° (that is to say by 360/n° wherein n is the number of number spacings, where in this case n=14 because there are twelve decimals indicia 232; one shutter portion 280 and one coloured portion 282) such that a single indicium 232 thereon is advanced (i.e. the 'tens' count moves down exactly one unit). In this instance, the decimal indicium 232 moves down from '12' to '11', as shown in FIGS. 14a and 14b.

Where the previous visible count was 10 (i.e. x=1), the counting action resulting from the use operation is again subtly different in that the kick wheel 240 action, as described above, results in the coloured (e.g. red) portion 282 of the second count wheel 230 being advanced into place in the window 216 such that the next display is 'red 9' (i.e. coloured portion 282; and numerals indicia 222 is number 9).

As shown at FIGS. 17a and 18a, where the previous visible count was 'red 0' (i.e. x=0), the counting action resulting from the use operation is still again subtly different in that the kick wheel 240 action, as described above, results in the shutter portion 280 of the second count wheel 230 being advanced into place in the window 216 such that the next display is fully shuttered off (i.e. no indicia 222, 232 visible at all, as shown at FIGS. 17b and 18b). Additionally, the stop position 238 in the set of second count wheel teeth 234 is brought into opposed relation with the kick teeth 244 whereby the kick teeth 244 and the teeth 234 no longer mesh. Thus, if the first count wheel 220 continues to rotate, e.g. in response to continued user operation of the drug dispenser device 1, 101 into which the actuation counter 201 is incorporated, notwithstanding that all drug doses in the prescribed dosing regime have been dispensed (although surplus doses may remain in the canister 5 for patient administration in accordance with regulatory requirements, as understood by the skilled person in the art), the index teeth 228a, 228b of the first count wheel 220 will still intermittently mesh with the kick teeth 244 to cause the kick wheel 240 to rotate. However, this rotation of the kick wheel 240 will not be transmitted to the second count wheel 230, due to the missing teeth of stop position 238, and the shutter 280 remains in the shuttering position in the window 216 so that the underlying 'units' indicium 222 remains unseen.

In this embodiment, the second count wheel 230 is integrally formed with the shutter portion 280.

The shutter portion 280 may be coloured, for instance be of the same colour (e.g. red) as the coloured portion 282.

To further illustrate the countdown display of the counter 201, the reader's attention is drawn to Table 1 below. Table 1 shows the sequential countdown for each of the units (first) and decimals (second) count wheels 220, 230 upon succeeding use operations or actuations of the counter 201, and also indicates which of these two count wheels 220, 230 indexes to bring the counter 201 to its new counter display. As shown in Table 1, the first (units) count wheel 220 indexes on each counter actuation, whereas the second (decimals) count wheel 230 only indexes (through the kick wheel 240 supra) each time the units indicium 222 of the first (units) count wheel 220 in the window 216 decrements from '0' to '9'. At the end of the countdown, when the display is shuttered, the first count wheel 220 is still free to rotate, underneath the shutter 280 so as not to be visible, and no further indexing of the second count wheel 230 occurs due to the stop position 238 providing for disengagement of the teeth 234, 244 of the second count wheel 230 and the kick wheel 240.

TABLE 1

| Sequential Counter Display in Window | Decimals Wheel Count in Window | Units Wheel Count in Window | Indexing of Units Wheel to this Count? | Indexing of Decimal Wheel to this Count? |
|---|---|---|---|---|
| 120 | 12 | 0 | — | — |
| 119 | 11 | 9 | Yes | Yes |
| 118-110 | 11 | 8 to 0 | Yes | No |
| 109 | 10 | 9 | Yes | Yes |
| 108-100 | 10 | 8 to 0 | Yes | No |
| 99 | 9 | 9 | Yes | Yes |
| 98-90 | 9 | 8 to 0 | Yes | No |
| 89 | 8 | 9 | Yes | Yes |
| 88-80 | 8 | 8 to 0 | Yes | No |
| 79 | 7 | 9 | Yes | Yes |
| 78-70 | 7 | 8 to 0 | Yes | No |
| 69 | 6 | 9 | Yes | Yes |
| 68-60 | 6 | 8 to 0 | Yes | No |
| 59 | 5 | 9 | Yes | Yes |
| 58-50 | 5 | 8 to 0 | Yes | No |
| 49 | 4 | 9 | Yes | Yes |
| 48-40 | 4 | 8 to 0 | Yes | No |

TABLE 1-continued

| Sequential Counter Display in Window | Decimals Wheel Count in Window | Units Wheel Count in Window | Indexing of Units Wheel to this Count? | Indexing of Decimal Wheel to this Count? |
|---|---|---|---|---|
| 39 | 3 | 9 | Yes | Yes |
| 38-30 | 3 | 8 to 0 | Yes | No |
| 29 | 2 | 9 | Yes | Yes |
| 28-20 | 2 | 8 to 0 | Yes | No |
| 19 | 1 | 9 | Yes | Yes |
| 18-10 | 1 | 8 to 0 | Yes | No |
| 9 | 'Red' | 9 | Yes | Yes |
| 8-0 | 'Red' | 8 to 0 | Yes | No |
| Shuttered | Shuttered | Shuttered | Yes | Yes |

After effective user actuation of the drug dispenser device 1, 101 and registration of the count, the levers 20a, 20b are released to return to their outward rest position and to allow the container collar 30 to return to its rest position. This results in the ratchet wheel 250 reversing, to reset it in its starting position for the next counting event, through interaction of the drive slot 82 with the drive-receiving protrusion 254.

Thus, the ratchet wheel 250 is adapted to not only rotate in the cavity 223 of the first count wheel 220 in the first rotary sense (clockwise as viewed in FIGS. 12 and 13a), but also to rotate in an opposite, second rotary sense (anti-clockwise as viewed in FIGS. 12 and 13a) in the first count wheel cavity 223.

However, while rotation of the ratchet wheel 250 in the first rotary sense drivably rotates the first count wheel 220 in the first rotary sense for indexing of the units count 222 in the window 216, rotation of the ratchet wheel 250 in the opposite, second rotary sense is relative to the first count wheel 220; i.e. the first count wheel 220 remains stationary so that the units indicia 222 in the window 216 remains unchanged. That is to say, frictional engagement between the respective wheels 220, 250 does not result in reverse rotation of the first count wheel 220, except for tolerance adjustments as discussed below.

To this end, the first count wheel 220 is provided with a pair of diametrically opposed resilient tongues or pawls 227 which co-operate with a serrated circumferential surface 211 of the first spindle 212a. The serrated surface 211 comprises plural ratchet teeth 215 with which the free ends 227a of the pawls 227 engage. As the skilled person will understand, as the first count wheel 220 is driven by the ratchet wheel 250 to rotate in the first sense, the free ends 227a of the pawls 227 ride over the respective ratchet tooth 215 presently engaged with and drop onto the next adjacent ratchet tooth 215 in the first sense, there being a step between adjacent teeth 215. This then indexes the first count wheel 220 in its new position, at which the next units indicia 222 in the count sequence registers with the window 216. However, the step between the adjacent ratchet teeth 215 prevents the first count wheel 220 rotating back in the opposite, second sense as the ratchet wheel 250 so rotates as the pawl free ends 227a cannot pass thereover.

As will also be appreciated by the skilled person, the ratchet teeth 215 provide tolerances in the indexing rotation of the first count wheel 220 by the ratchet wheel 250. In other words, the first count wheel 220 can be slightly over-rotated in the first sense, but as the ratchet wheel 250 rotates back in the opposite, second sense it carries the first count wheel 220 in the same sense, through frictional forces, until the pawl free ends 227a engage the step between the ratchet teeth 215 which then prevents further reverse rotation of the first count wheel 220 and indexes the units indicia 222 in the window 216.

As shown in FIGS. 12 and 13b, for example, the upper front part 210 of the drug dispenser device 1, 201 further provides a resilient pawl 217. The pawl 217 has a free end 217a which engages the indentations 236 in the outer circumferential surface of the top face 237 of the second count wheel 230, as shown in FIGS. 14a and 14b, for instance. There is one indentation 236 for each count or index position of the second count wheel 230, so the free end 217a of the pawl 217 and the indentations 236 provide an indexing function which provides for accurate alignment of the decimals indicia 234 in the window 216 and inhibits or prevents reverse rotation of the second count wheel 230.

The indentations 236 in this embodiment have a symmetrical shape, more particularly a generally U-shape. However, other shapes could be used. Moreover, asymmetric shapes could also be used. For instance, it may be useful for the flanks of the indentations 236 to present different angles, for example for the trailing (rear) flanks of the indentations 236 (relative to the direction of rotation of the second count wheel 230, e.g. anti-clockwise in FIGS. 14a and 14b) to form a greater angle with a central radial line through the indentations 236 than the leading (forward) flanks. This means there is less resistance to the pawl 217 releasing from the indentations 236 as the second count wheel 230 is driven by the kick wheel 240.

It will be appreciated that the above usage of the actuation counter has been described in terms of a counter assembly 201 arranged to count downwards (i.e. to count on from 'n+1' to 'n' on indexing), but that the counter assembly may be straightforwardly modified to count upwards (i.e. instead to count on from 'n' to 'n+1' on indexing).

Alternatively, other indicators than a complete countdown/count-up could be employed to indicate the amount of drug content left in the canister 5, such as the use of colour scales, line or block scales or letters/words on the count wheels 220, 230.

The components of the actuation counter 201 and any assemblies and sub-assemblies described above may be made from any suitable materials such as plastic polymer materials (e.g. acetal or ABS or styrene polymers). In particular, the count wheels 220, 230 may be of ABS while the kick wheel 240 and the ratchet wheel 250 may be of acetal.

In a modification of the counter 201 (not shown), the friction resistance between the kick wheel 240 and its spindle mounting 214 may be increased to provide a dragging or braking effect which retards the speed of rotation of the kick wheel 240 when driven by the first count wheel 220. One possible way to achieve this is through the provision of axially-oriented splines about the outer periphery of the spindle mounting 214. This may prevent or inhibit any tendency for the second count wheel 230 to be misaligned or over-indexed by a fast moving kick wheel 240.

The interrelationship between the actuation counter 201 and the drug dispenser device 1 is now described in more detail with reference to FIGS. 19 to 21. For clarity and succinctness, only relevant parts of FIGS. 19 to 21 are labelled.

FIG. 19 shows the drug dispenser device 1 with upper front cover part 10a and actuation counter 201 removed. The device 1 is in the 'at rest' position with the levers 20a, 20b not depressed.

FIG. 20 shows the drug dispenser device 1 with the upper front cover part 10a and actuation counter 201 disposed therein shown detached from the remainder of the device 1. The drug dispenser device 1 is again in the 'at rest' position with the levers 20a, 20b not depressed. FIG. 21 shows further details of the actuation counter 201 disposed in the upper front cover part 10a of the drug dispenser device 1.

Arrow A of FIG. 20 indicates the direction of reciprocal movement of the container collar 30 and driver plate 80 attached thereto resulting from effective user actuation of the drug dispenser device. Arrow B of FIG. 20 indicates the resulting interaction between the downward drive slot 82 of the driver plate 80 and the drive-receiving protrusion 254 of the ratchet wheel 250 of the actuation counter 201.

Detailed aspects of the drug dispenser device 1 and actuation counter 201 of FIGS. 19 to 21 correspond to those already described by reference to FIGS. 1 to 11 and FIGS. 12 to 18b respectively, and for succinctness these are not described further.

Registration of a count is now described. In use, following effective user actuation of the drug dispenser device 1 by squeezing the levers 20a, 20b together, as described hereinabove with reference to FIGS. 1 to 7, the container collar 30 and driver plate 80 move downwards in tandem/unison. The downward drive slot 82 on the driver plate 80 drivably engages the drive-receiving protrusion 254 to drive on the ratchet wheel 250 of the actuation counter 201 thereby resulting in registration of a count. As described previously, effective user actuation which results in the downward movement of the container collar 30 (and actuation of drug release from the canister 5) occurs only once a pre-load threshold ('tipping') force has been overcome (by that effective user actuation). Thus, it will also be appreciated that a count is only registered by the actuation counter 201 in response to such an effective user actuation. The registered count thus, fully ties in with the number of occurrences of drug release.

FIGS. 22 to 27c show different aspects of key parts of an alternative internal mechanism for use with the drug dispenser device 1 and canister 5 as hereinbefore described. This alternative mechanism may be appreciated to be a slight variation of that previously described, mainly in relation to FIG. 5.

Details of the container collar 330 of the alternative internal mechanism are shown at FIGS. 22 and 23. Details of the extension collar 340 of the alternative internal mechanism are shown at FIGS. 24 and 25. Assembly steps relating to the alternative internal mechanism are illustrated at FIGS. 26a to 26c, and key operational aspects at FIGS. 27a to 27c.

As before, the container collar 330 permanently engages via split-ring collar 333 with the neck 305a of the canister 305 such that the so-engaged parts are moveable together (i.e. in unison) relative to the housing in a direction defined by the longitudinal axis L-L of the canister 305 (i.e. generally up and down when the device 1 is upright). The split-ring collar 333 permanently engages the container collar 330 to the canister 305 as will be understood from U.S. patent application Ser. Nos. 10/110,611 (WO-A-01/28887) and US-A-2006/0082039.

Again, as before the container collar 330 connects via closed coil extension springs 350a (only one visible in FIG. 26c) and respective spring connection points 331a, 331b and 341a, 341b to extension collar 340, which is provided at its lower end with an outer ramp 344, and also with an inner ramp 343. This multi-collar arrangement is such that the extension collar 340 is moveable with respect to the container collar 330 along the longitudinal axis L-L of the drug discharge device.

The extension collar 340 includes an actuating portion in the form of shelf 342, which is arranged for interaction with the lower ends 21a, 21b of the opposing levers 20a, 20b such that when the levers 20a, 20b of the device 1 are squeezed together (i.e. inwards relative to the housing) the shelf 342 and hence, extension collar 340 are pushed downwards. The container collar 330 is further provided with flexible support legs 334*a*, 334*b*, 334*c* which as before, act to provide a pre-load mechanism to prevent transfer of that biasing energy to the container collar 330 to move the canister 5 downwards along the longitudinal axis L-L to actuate the valve thereof (and hence, to fire the aerosolized drug dose) until a pre-determined threshold force is overcome. Again, as before each flexible support leg 334*a*, 334*b*, 334*c* is arranged for interaction with a respective step 18*a*, 18*b* on the housing. However, in this variation each flexible support leg 334*a*, 334*b*, 334*c* is provided with a protruding inner foot 335*a*, 335*b*, 335*c* and protruding outer foot 336*a*, 336*b* (only two visible) the purpose of which will become clearer from the later description.

Assembly steps relating to those key parts of the alternative internal mechanism are illustrated at FIGS. 26*a* to 26*c*. The split-ring collar 333, which generally comprises a plastic polymer material, is used to permanently fix the container collar 330 to the neck 305*a* of the canister 305 by ultrasonic welding, as generally described in U.S. patent application Ser. Nos. 10/110,611 (WO-A-01/28887) and US-A-2006/0082039.

The welding process may use two sonotrodes (ultrasonic welding heads) each with three small conical projections to focus the weld energy. During the welding process the conical projections are plunged into the outer surface of the container collar 330 allowing the ultrasonic energy to create a pool of molten material to form the bond (welds) between inside surface of the container collar 330 and the outer surface of the split-ring collar 333, which is wedged between the neck 305*a* of the container 305 and the inside surface of the container collar 330.

In a subtle variation of that ultrasonic welding process, the inner surface of the container collar 330 is provided with plural (e.g. two sets of three) spaced longitudinal ribs (not visible). During this variation of the welding process one or more plural pronged (e.g. three pronged) ultrasonic welding heads (not shown) are arranged about the container collar 330 with their prongs aligned one to each rib (which abut with the split-ring collar 333 which is wedged between the container neck 305*a* and the ribs) and ultrasonic energy applied to form welds between the inside surface of the container collar 330 and the outside surface of the split-ring collar 333 using the rib material.

This alternative welding process, which is known as an 'energy director' method avoids any 'splash back' of particulate weld material which may otherwise occur where some of the molten material may be displaced onto the outside surface of the container collar 330 to form a 'splash' thereon which can subsequently detach. Such 'splash back' is disadvantageous because any particulates resulting therefrom may potentially lodge within the dispenser and thus, possibly be inhaled by the user. As the alternative process focuses the weld energy at the internal ribs, the sonotrode(s) no longer has the conical projections and, as the ribs are sandwiched between the container collar 330 and the split-ring collar 333, most if not all extraneous molten material will be encapsulated and therefore unable (or less able) to become detached.

As shown at FIG. 26*a*, in a first step of the assembly process, the canister 305 with split-ring collar 333 located about its neck 305*a* is aligned above the container collar 330 and extension collar 340. In a next step, as shown at FIG. 26*b*, the canister 305 with split-ring collar 333 is inserted into the container collar 330, the split-ring collar 333 is adjusted to be wedged between the neck 305*a* and the inside surface of the container collar 330 and then the container collar 330 and the split-ring collar 333 are permanently joined by one of the afore-described welding processes to thereby permanently fix the container collar 330 to the canister 305. The so-engaged parts 305, 330, 333 are moveable together (i.e. in unison) relative to the housing in a direction defined by the longitudinal axis L-L of the canister 305 (i.e. generally up and down when the device 1 is upright).

The canister 305 and container collar 330 assembly is then inserted into the extension collar 340. The container collar 330 is connected via closed coil extension springs 350*a* (only one visible) and respective spring connection points 331*a*, 331*b* and 341*a*, 341*b* to the extension collar 340, as shown at FIG. 26*c*. When so-connected, the extension collar 340 is moveable with respect to the container collar 330 along the longitudinal axis L-L of the drug discharge device.

It will be appreciated that the overall form of the alternative internal mechanism is very similar to that previously described in relation to FIG. 5 other than that the shaping of the flexible support legs 334*a*, 334*b*, 334*c* differs slightly from those legs 34*a*, 34*b* of the internal mechanism of FIG. 5, and that correspondingly the ramp 44 thereof is replaced in the alternative internal mechanism by both an inner 343 and outer 344 ramp. The operational effect of these slight variations is described in greater detail below in relation to FIGS. 27*a* to 27*c*. Other than these slight variations, the general principles of operation of the device 1 with the alternative internal mechanism of FIGS. 22 to 27*c* correspond to those previously described with reference to FIGS. 3*a* to 4*c*.

Thus, in general operational terms, referring now also to FIGS. 27*a* to 27*c*, the opposing levers 20*a*, 20*b* of the device 1 are moveable transversely with respect to the longitudinal axis L-L of the drug discharge device to apply a force to the shelf 342 of the extension collar 340 to move the extension collar 340 downwards along that longitudinal axis (i.e. towards stem block 8 and mouthpiece 14 of the device 1).

The closed coil extension springs 350*a* that connect the container collar 330 via connector points 331*a*, 331*b* with the extension collar 340 act as a biasing mechanism to store biasing energy on moving the extension collar 340 downwards along the longitudinal axis L-L in response to squeezing of the levers 20*a*, 20*b*. In embodiments, an initial biasing tension—inherent in the closed coil form thereof—is present in the closed coil extension springs 350*a* even when in their 'at rest' state.

The flexible support legs 334*a*, 334*b*, 334*c* act to provide a pre-load mechanism to prevent transfer of that biasing energy to the container collar 330 to move the canister 305 downwards along the longitudinal axis L-L to actuate the valve thereof (and hence, to fire the aerosolized drug dose) until a pre-determined threshold force is overcome.

FIGS. 27*a* to 27*c* illustrate details of the relationship between a flexible support leg 334*a* of container collar 330 and an inner 343 and outer ramp 344 of the extension collar 340 during operation of the device 1.

FIG. 27*a* shows details of this relationship when the device 1 is in the 'at rest' position (i.e. corresponding to previous FIG. 3*a*). That is to say, with no downward force applied by the levers 20*a*, 20*b* to the shelf 342 of the extension collar 340. The flexible support leg 334*a* of the container collar 330 protrudes down between the inner 343 and outer 344 ramps of the extension collar 340, and interacts at its bottom end with a respective step 18*a*, 18*b* on the housing.

FIG. 27*b* shows details of this relationship when the device 1 is in a 'tipping point' configuration (i.e. roughly corresponding to previous FIG. 4*c*). In this position, significant downward force has been applied by the levers 20*a*, 20*b* of the device 1 to the shelf 342 of the extension collar 340. The outer ramp 344 of the extension collar 340 has been brought down on the protruding outer foot 336a of the flexible leg support 334a, thereby causing the flexible leg support 334a to flex inwards and to be displaced interiorly to the outer ramp 344. In consequence, noting that this interaction happens concurrently with the other pairs of outer ramps 344 and outer feet 336b, 336c, the container collar 330 may now move freely downwards and indeed, will do so as a result of its experience of biasing energy stored in the extension springs 350a. The container collar 330 and canister 305 in permanent engagement therewith move rapidly downwards propelled by the stored biasing energy of the springs 350a. The valve 306 of the canister 305 is thereby activated to release aerosolized drug for inhalation by the patient.

As before, it will be appreciated that once the threshold force has been overcome (i.e. just past the 'tipping point' of the device 1) a uniform actuating force resulting from the energy stored in the springs 350a is experienced by the container collar 330 and canister 305 regardless of how much extra force is applied by the patient to the levers 20a, 20b. A consistent actuation of the valve of the canister 305 is thereby, enabled.

Following actuation, the coiled coil extension springs 350a return to their 'at rest' state (i.e. with no externally-applied biasing energy, but only any initial biasing tension inherent in the closed coil form of the extension springs 350a present). As will be appreciated by the skilled reader in the art, the return spring (not shown) of the valve 306 of the valved canister provides energy to move the canister 305, container collar 330, extension collar 340 and levers 20a, 20b back to the 'at rest' position. As shown at FIG. 27c, during this return operation the inner protruding foot 335a of the flexible leg 334a interacts with the inner ramp 343 of the extension collar 340, the effect of this interaction being to push the flexible leg 334a outwards to the 'at rest' state of FIG. 27a, in which the flexible leg 334a is un-flexed.

FIGS. 31a and 31b respectively show back and front views of a driver plate 690, typically made of a plastics material, for instance acetal, for use with a modified version 601 of the actuation counter 201 of FIGS. 12 to 21 in accordance with the present invention. The modified actuation counter 601 will be appreciated to have a generally similar mode of usage to that of the unmodified counter 201, but also includes features to prevent 'overrun' of the count. The operation of the modified counter 601 is described below in more detail with reference to FIGS. 32a to 35b.

The driver plate 690 of FIGS. 31a and 31b may be appreciated to have the same outline form (i.e. I-form) as that of driver plate 80 of FIGS. 19 to 20 as previously described in relation to use with the drug dispenser device 1 of FIG. 1. It will be appreciated from the following description that the driver plate 690 and the modified actuation counter 601 of FIGS. 32a to 35b are also arranged to be suitable for use with the drug dispenser device 1, 101 of FIGS. 1 and 11.

Thus, the driver plate 690 is arranged in use, to be permanently fixed to the container collar 30 of the drug dispenser device 1, 101 so as to move in tandem therewith. In embodiments, the driver plate 690 is permanently fixed to the container collar 30 by ultrasonic welding. Whilst in alternative embodiments the driver plate 690 and container collar 30 may be provided as an integral part there are advantages associated with forming them as separate parts, which are then fixed (e.g. ultrasonically welded) together. In particular, the welding of the driver plate 690 to the container collar 30 as part of a final assembly process allows the positioning of the driver plate 690 relative to the container collar 30 to be effectively tailored to each container collar 30 and device 1, 101 to ensure effective operation of the actuation counter 601. Thus, manufacturing tolerance variations across a variety of components of the device 1, 101 and/or counter 601 may effectively be compensated for.

The driver plate 690 is provided with a driver feature in the form of a downward drive slot 692 that is arranged in use, for driving interaction with a drive-receiving feature (e.g. drive-receiving protrusion 254 of the ratchet wheel 250 of the actuation counter 201 of FIG. 12) for driving on of the actuation counter 601 to register a count. The driver plate 690 differs from that driver plate 80 of FIGS. 19 to 20 in that a protruding brake element 694 is provided to the upper front part thereof. As will become clear from the later description, the brake element 694 is arranged to selectively interact with the first counter wheel 620 and/or second count wheel 630 of the modified actuation counter 601 to prevent overrun thereof when registering a count of an actuation of the drug dispenser device 1, 101.

FIGS. 32a to 32g and FIGS. 33a to 33g show corresponding plan and perspective views of sequential operation steps of key parts of the modified actuation counter 601. Those key parts are the driver plate 690; first (units) count wheel 620; second (decimals) count wheel 630; kick wheel 640 and ratchet wheel 250). All other parts of the modified actuation counter 601 (e.g. including the housing 10a with spindle mountings 212, 214) correspond to those of the unmodified actuation counter 201 of FIGS. 12 to 18b).

FIGS. 34a and 34b respectively show perspective underside and top views of the first count wheel 620 (typically made of a plastics material, for instance ABS) for use in the modified actuation counter 601. Thus, disc-shaped first count wheel 620 has 'units' (i.e. numerals) count indicia 622 provided at spaced intervals on a top face thereof. Alignment holes 622a, 622b and notches 622e, 662f are provided adjacent indicia '6' and '7' and '8' and '9' respectively, and also alignment holes 622c, 622d adjacent indicia '3' and '8' for alignment of the first count wheel 620 with the second count wheel 630 (typically made of a plastics material, for instance ABS) during assembly of the counter 601. The first count wheel 620 is provided with a central aperture 626 and a circular cavity 623 that is arranged for disposed receipt of ratchet wheel 250 (not shown, but see e.g. FIGS. 12 and 21). Ratchet drive receipt teeth 624 are arranged about the inner circumferential wall 625 of the cavity for ratcheted drive interaction with the ratchet wheel 250. With reference also to FIGS. 12 and 21, the ratchet wheel 250 itself, is sized and shaped for receipt by the circular cavity 623 of the first count wheel 620 and is provided with two oppositely-located drive tongues 252a, 252b for ratcheted drive interaction with the ratchet drive receipt teeth 624. The ratchet wheel 250 is also provided with a drive-receiving protrusion 254 arranged in use, for drivable rotation of the ratchet wheel 250 in response to drive interaction with downward drive slot 692 of the driver plate 690 in which slot 692 the drive-receiving protrusion 254 locates, in use.

The first count wheel 620 is also provided with a pair of diametrically opposed resilient tongues or pawls 627 which co-operate with a serrated circumferential surface 211 of the first spindle 212a (not shown, but see FIG. 12). The serrated surface 211 comprises plural ratchet teeth 215 with which the free ends 627a of the pawls 627 engage. As before, as the first count wheel 620 is driven by the ratchet wheel 250 to rotate in the first sense (anti-clockwise as viewed in FIGS. 32 to 33, as shown by arrow A in FIGS. 32b and 33b) the free ends 627a of the pawls 627 ride over the respective ratchet tooth 215 presently engaged with and drop onto the next adjacent ratchet tooth 215 in the first sense, there being a step between adjacent teeth 215. This then indexes the first count wheel 620 in its new position, at which the next units indicia 622 in the count sequence registers with the window 616 (e.g. corresponding to window 216 in FIG. 1). However, the step between the adjacent ratchet teeth 215 prevents the first count wheel 620 rotating back in the opposite, second sense as the ratchet wheel 250 so rotates as the pawl free ends 627a cannot pass thereover.

First count wheel 620 may also be seen to be provided with a pair of fixed index teeth 628a, 628b arranged for intermittent meshing with the kick teeth 644 of the kick wheel 640 (typically made of a plastics material, for instance acetal) such that rotary motion of the kick wheel 640 results from rotary motion of the first count wheel 620 only when said intermittent meshing occurs (see FIGS. 32a to 33g and also FIGS. 15a and 15b showing corresponding index teeth 228a, 228b of the unmodified actuation counter). The first count wheel 620 is further provided with a peripheral flanged portion 621. Notch 621a is provided to this flanged portion adjacent to fixed index tooth 628b to prevent the kick teeth 644 of the kick wheel 640 snagging the peripheral flange of the first count wheel 620. The peripheral flanged portion 621 of the first count wheel 620 also includes at equally-angularly spaced-apart intervals on the outer circumference thereof a series of shaped notches or saw-tooth indentations 629 (e.g. 'crenellations') provided with near-radial lead faces 629a and arranged for selective interaction with the brake element 694 of the driver plate 690, as will be described in more detail later. The saw-tooth indentations 629 may be noted to have an asymmetrical shape, more particularly an offset U-shape with near-radial lead face (flank) 629a.

FIGS. 35a and 35b respectively show perspective underside and top views of the second count wheel 630 for use in the modified actuation counter 601. The second, ring form count wheel 630 has 'tens of units' (i.e. decimals) count indicia 632 provided at spaced intervals on a top face 637 thereof and a set of drive teeth 634 provided in annular arrangement to the underside thereof. Alignment notches 632a, 632b are provided adjacent indicia '3' and '4' and '8' and '9' respectively for alignment of the first counter wheel 620 with the second count wheel 630 during assembly of the counter 601. It may be noted that at stop position 638, a couple of the teeth 634 have been removed. It will also be noted that the outer circumferential edge of top face 637 is formed with a series of equally-angularly spaced-apart notches or saw-tooth indentations 636 (e.g. 'crenellations') provided with near-radial lead faces 636a and arranged in one aspect, for selective interaction with the brake element 694 of the driver plate 690, as will be described in more detail later. The saw-tooth indentations 636 may be noted to have an asymmetrical shape, more particularly an offset U-shape with near-radial lead face (flank) 636a. The second count wheel 630 is also provided with a protruding shutter 680, which is coloured, the function of which is identical to that of the shutter 280 of the second count wheel 230 of the unmodified counter 201 and the operation of which, for succinctness, will not be described in detail. The second count wheel 630 also has coloured portion 682, the function of which is identical to that of coloured portion 282 of the unmodified counter 201, and which again will therefore not be described in detail. The colour of the shutter 680 and coloured portion preferably corresponds (e.g. both are red), but they may be of different colours.

Referring now to FIGS. 32a to 32g and FIGS. 33a to 33g, the key parts (driver plate 690; first count wheel 620; second count wheel 630; kick wheel 640 and ratchet wheel 250) of the modified counter 601 are shown in the configuration which they would adopt in the full counter arrangement. Kick wheel 640 may be seen to have kick teeth 644 provided in annular arrangement around the circumference thereof. FIGS. 32a to 32g also show resilient pawl 217 (refer also to FIG. 12). The pawl 217 has a pawl portion 217a which trails the saw-tooth indentations 636 in the outer circumferential surface of the top face 637 of the second count wheel 630 to align the dose count. There is one indentation 636 for each count or index position of the second count wheel 630, so the free end 217a of the pawl 217 and the saw-tooth indentations 636 provide an indexing function which provides for accurate alignment of the decimals indicia 634 in the window 616 (see also FIGS. 14a and 14b, which show corresponding features of the unmodified counter 201) and inhibits or prevents reverse rotation of the second count wheel 630. The ratchet wheel 250 has identical form to that ratchet wheel 250 of the unmodified counter 201 of FIGS. 12 to 21 save that a V-groove feature 256 has been added at the front for assembly alignment purposes.

Sequential operation of the modified actuation counter 601 is now described by reference to FIGS. 32a to 32g, and 33a to 33g. For succinctness only specifically referred-to parts of the Figures showing later aspects of the operation are labelled.

At FIGS. 32a and 33a, the modified actuation counter 601 is shown at rest with a count of '71' registering in the count window 616. The brake element 694 of the driver plate 690 is spaced from both count wheels 620, 630. This configuration corresponds to when the aerosol canister 5 is in its rest or return position in the drug dispenser device 1, 101 (e.g. before initiating actuation of the device 1 by squeezing the levers 20a, 20b).

Figure 33B:
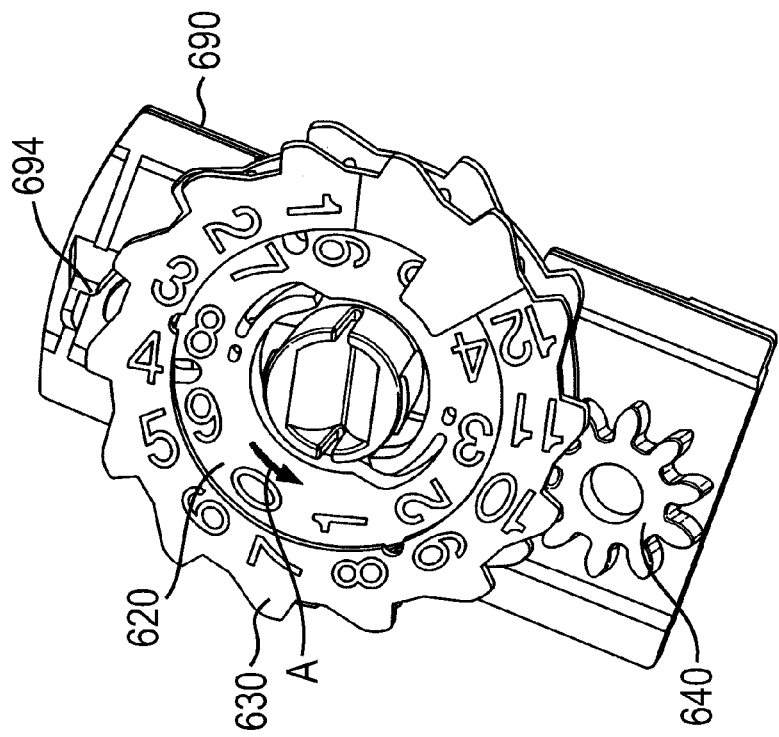
Figure 32B:
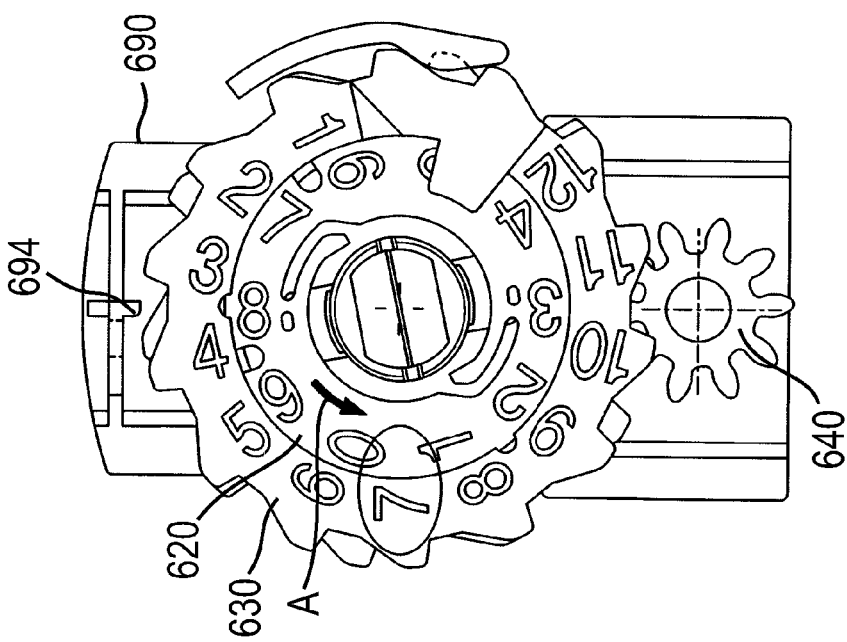

At FIGS. 32b and 33b, the drug dispenser device 1, 101 has been actuated by squeezing the levers 20a, 20b towards one another. Thus, ratchet wheel 250 has been rotated in response to effective user actuation of the drug dispenser device 1, 101 by squeezing the levers 20a, 20b together as previously described with reference to FIGS. 1 to 7 above. This results in the driver plate 690 starting to move on a linear downwards path and the drive slot 692 driving the ratchet wheel protrusion 254 to rotate the ratchet wheel 250 in a first rotary sense. This, in turn, results in rotation of the first count wheel 620 in the first rotary sense by the meshed interaction of drive tongues 252a, 252b with ratchet drive receipt teeth 624. The ratchet wheel 250 and first count wheel 620 are configured and arranged such that when indexed first count wheel 620 rotates by 36° in the direction of Arrow A such that a single indicium 622 thereon is advanced (i.e. as shown the 'units' count moves down one unit from indicia '1' to indicia '0'). Since this is not a 'tens' counting down, the kick wheel 640 and second count wheel 630 do not move. It will be noted that the spacing of the brake element 694 from the count wheels 620, 630 has also been reduced.

Figure 33C:
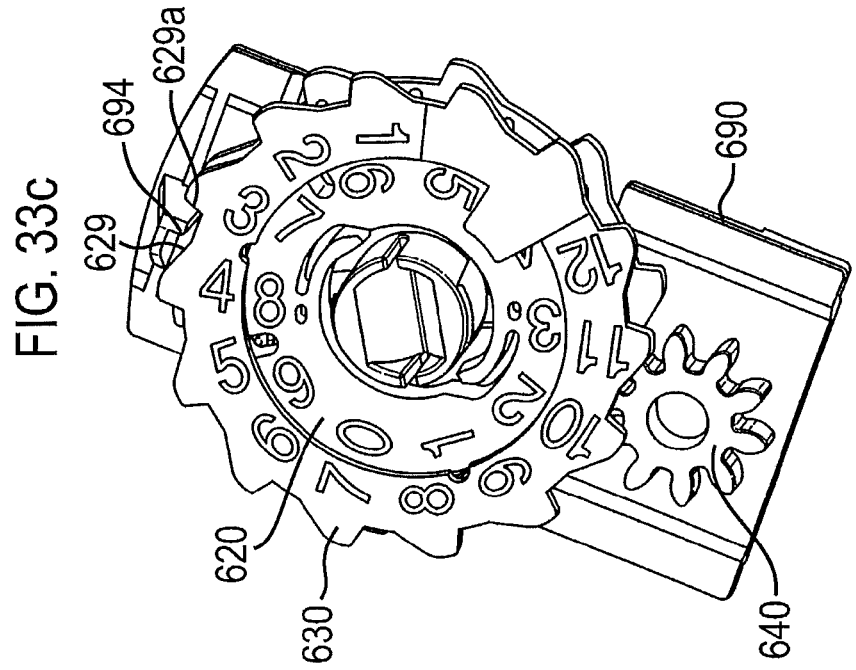
Figure 32C:
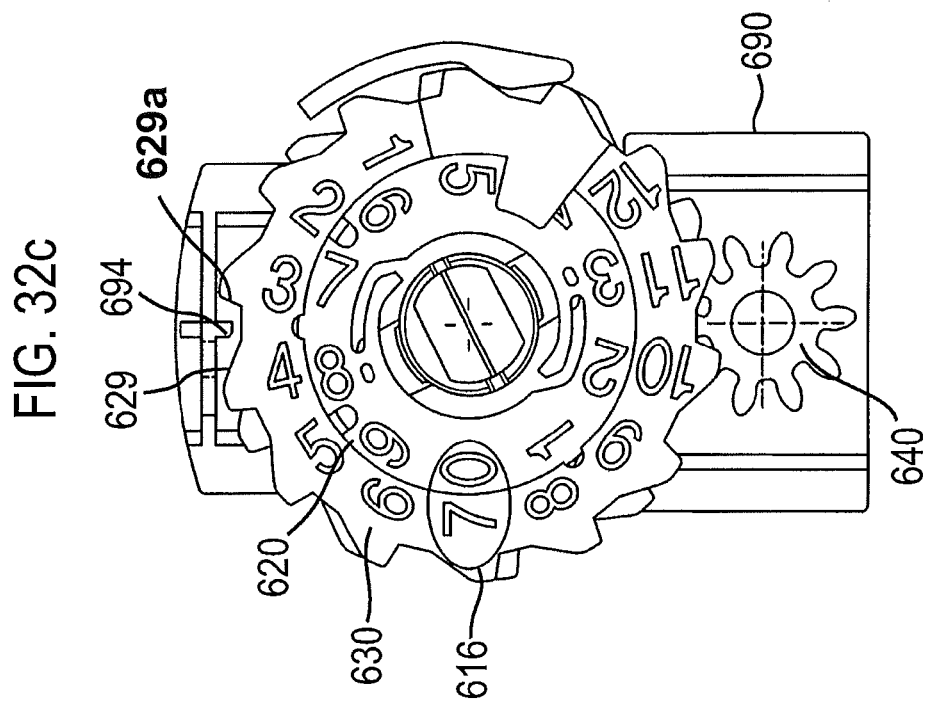

At FIGS. 32c and 33c, the drug dispenser device 1, 101 has been fully actuated and as a result the driver plate 690 moved fully along its linear downwards path. The drive slot 692 has transferred further drive to the drive-receiving protrusion 254 of the ratchet wheel 250, which causes the first count wheel 620 to rotate sufficiently in an anti-clockwise sense that the numerals indicia '0' registers in the viewing window 616 such that a count of '70' is registered thereat. Further, brake element 694 has been brought into blocking interaction with one of the saw-tooth indentations 629 of the first count wheel 620 (and also into blocking interaction with one of the saw-tooth indentations 636 of the second count wheel 630). The effect of this blocking interaction is that further rotation of the first count wheel 620 is prevented and thus, any overrun thereof (e.g. associated with a particularly extreme actuating movement) beyond the '70' count position is prevented. In more detail, the intent is that the lead face 629a of that one of the saw-tooth indentations 629 of the first count wheel 620 only physically abuts up against the brake element 694 to prevent count overrun by over-rotation of the first count wheel 620 in an extreme circumstance.

After effective user actuation of the drug dispenser device 1, 101 and registration of the count, the levers 20a, 20b are released to return to their outward rest position and to allow the container collar 30 and driver plate 690 carried thereon to return to the rest position. This 'return' of the driver plate 690 to its start (i.e. non-downwardly displaced) position happens (as previously described in relation to the non-modified actuation counter 201) under the influence of the return biasing force of the valve spring of the valve canister 5. As a result, the ratchet wheel 250 reverses, to reset it in its starting position for the next counting event, through interaction of the drive slot 692 with the drive-receiving protrusion 254. Thus, as shown at FIGS. 32d and 33d, the driver plate 690 of the modified counter 601 has been returned to its start position with the brake element 694 of the driver plate 690 spaced from both count wheels 620, 630. The count of '70' still registers in the count window 616.

In a detail element, it may be appreciated that the inclusion of brake element 694 onto the driver plate 690 ensures that part (i.e. driver plate 690) that initiates the drive interaction for the actuation counting operation (i.e. by drive slot 692 acting on drive-receiving portion 254) also effectively finishes that action (i.e. by blocking action of the brake element 694). Thus, the drive stroke is effectively controlled by the action of different fixed parts 692, 694 of a single driver plate 690, thereby minimizing the tolerance loop.

Each actuation of the drug dispenser device 1, 101 resulting in only the first (units) count wheel indexing results in the counter operation as described above, whereby the braking element is positioned in a different indentation 629 of the first count wheel 620 (and also in an indentation 636 of the second count wheel) in the downward stroke of the driver plate 690 to prevent overrun of the first count wheel 620.

Where the pre-count operation visible count is x0 (e.g. 70 with 'x=7', as shown at FIGS. 32d and 33d), the counting action resulting from the next use operation is subtly different. Thus, at FIGS. 32e and 33e, the drug dispenser device 1, 101 has been actuated for a second time in the manner as described previously. Once again, driver plate 690 starts to move on a linear downwards path. As before, the drive slot 692 thereof transfers drive to the drive-receiving protrusion 254 of the ratchet wheel 250, which is rotated in response to effective user actuation of the drug dispenser device 1, 101 causing rotation of the first count wheel 620 by 36° in the direction of Arrow A such that the 'unit' indicium 622 starts to move on from '0' to '9'. This rotation of the first count wheel 620 however, also brings the pair of index teeth 628a, 628b into meshed relationship with the kick teeth 644 of kick wheel 640 such that the kick wheel 640 rotates and in turn, causes the second count wheel 630 to rotate through meshing of their respective teeth 634, 644. The wheels 620, 630, 640 are configured and arranged such that the resultant rotation in the direction of Arrow B of the second count wheel 630 is by 360/14° (that is to say by 360/n° wherein n is the number of number spacings, where in this case n=14 because there are twelve decimals indicia 632; one shutter portion 680 and one coloured portion 682) such that a single indicium 632 thereon is advanced (i.e. the 'tens' count moves down exactly one unit). In this instance, the decimal indicium 632 moves starts to move down from '7' to '6', as shown in FIGS. 32e and 33e.

The spacing of the brake element 694 from the count wheels 620, 630 has also been reduced.

At FIGS. 32f and 33f, the drug dispenser device 1, 101 has been fully actuated and as a result the driver plate 690 moved fully along its linear downwards path. The drive slot 692 has transferred further drive to the drive-receiving protrusion 254 of the ratchet wheel 250, which has caused the first count wheel 620 to rotate sufficiently in an anti-clockwise (first) sense that the numerals indicia '9' registers in the viewing window. Further, the kick wheel 640 has acted on the second count wheel 630 to rotate that second count wheel sufficiently in an anti-clockwise (the first) sense that the decimals indicia '6' registers in the viewing window 616. Thus, overall a count of '69' is registered thereat. Further, brake element 694 has been brought into blocking interaction with one of the saw-tooth indentations 629 of the first count wheel 620 and also into blocking interaction with one of the saw-tooth indentations 636 of the second count wheel. The effect of this blocking interaction is that further rotation of both the first count wheel 620 and the second count wheel 630 is prevented and thus, any overrun thereof beyond the '69' count position is prevented. In more detail, the intent is that the lead faces 629a, 636a of that one of the saw-tooth indentations 629, 636 of the first 620 and/or second 630 count wheels only physically abut up against the brake element 694 to prevent count overrun by over-rotation of the first 620 and/or second 630 count wheels in an extreme circumstance. Alignment of the count wheels 620, 630 is by action of the resilient pawl 217 with the relevant indentation 636 of the second count wheel 630. The brake element 694 provides no such count wheel 620, 630 alignment function.

At FIGS. 32g and 33g, the driver plate 690 of the modified counter 601 has been returned to its start position with the brake element 694 of the driver plate 690 spaced from both count wheels 620, 630. This 'return' of the driver plate to its start (i.e. non-downwardly displaced) position happens, as previously described in relation to the non-modified actuation counter 201, as a result of the return biasing force of the valve spring of the valve canister 5. The count of '69' still registers in the count window 616.

Each actuation of the drug dispenser device 1, 101 resulting in both the first (units) and second (tens/decimals) count wheels indexing results in the counter operation as described above, whereby the braking element is positioned in a different indentation 629, 636 of the first and second count wheels 620, 630 in the downward stroke of the drive plate 690 to prevent overrun of the first and second count wheels 620, 630.

It will be understood that, as with the unmodified actuation counter 201, the countdown sequence of the modified actuation counter 601 is as shown in Table 1 supra, although the start number for the countdown sequence (as shown in window 616) can be varied by appropriate pre-setting of the position of the count wheels 620, 630. It will also be understood that the number of numerals on the second (tens/decimal) count wheel 630 can be different to that shown in FIGS. 32a to 35b so that the starting countdown number in the window 616 is different.

It will be further understood that, as with the unmodified actuation counter 201, at the end of the countdown sequence with the modified actuation counter 601 no drive is transmissible from the kick-wheel 640 to the second count wheel 630 as a result of the missing teeth at the stop position 638, so that, while the first count wheel 620 can continue to be indexed on continued user actuation of the drug dispenser device 1, 101 (for access to surplus doses therein), the shutter 680 still shutters the window 616 so that the units indicium is not visible.

One particular advantage of the 'count overrun' preventing action of the brake element 694 is that effective counting with no overrun can be assured even where particularly high dispenser device 1, 101 actuating forces and speeds are employed. Thus, the modified counter 601 may be used with dispenser devices 1, 101 designed for use with a broad range of actuating and valve forces (e.g. more robust forces than usual) and accommodate a broad range of actuating speeds (e.g. relating to different user actuation behaviours and/or profiles).

FIGS. 36 to 38 show another form of driver plate 790, first count wheel 720 and second count wheel 730 for a modified version of actuation counter 201 which operate in the same way as the corresponding parts of the modified actuation counter 601 described with reference to FIGS. 31 to 35.

When the levers 20a, 20b of the drug dispenser device 1; 101 are depressed inwardly, to operate the device, the apertures 11a, 11b in which the levers 20a, 20b are mounted are opened in the sense that a pathway into the device 1; 101 is revealed, as evident from FIGS. 8 and 9. With this in mind, to ensure that the actuation counter is protected against tampering or misuse after the levers 20a, 20b are depressed inwardly, the driver plate 790 is shaped, in particular through the inclusion of the wings 790a, so that the actuation counter wheels 720, 730 are hidden and inaccessible through the revealed apertures 11a, 11b. Thus, the driver plate 790 acts as a shield for the actuation counter.

The driver plate 790 is also provided with clips 790b which provide a sliding connection of the driver plate 790 on the inside of the upper front part 10a of the drug dispenser device 1; 101. Once the driver plate 790 is slidably connected to the upper front part 10a, through the clips 790b, the container collar 30 is then fixed to the driver plate 790, as previously described herein for the driver plate 80.

A comparison of FIGS. 37 and 38 to FIGS. 34 and 35 reveals that the profile of the respective saw-tooth indentations (e.g. 'crenellations') 729, 736 of the first and second count wheels 720, 730 is subtly different than the saw-tooth indentations (e.g. 'crenellations') 629, 636 of their counterparts 620, 630. This subtle change of profile provides an enhanced cooperation between the first and second count wheels 720, 730 with the resilient pawl 217.

It will be appreciated that the driver plate 790 and the first and second count wheels 720, 730 could be used collectively or in isolation in place of their counterparts 690, 623, 630 in the actuation counter 601 of FIGS. 31 to 35.

The materials of the other components of the modified actuation counters of FIGS. 31 to 38, such as for the kick-wheel and the ratchet wheel, may be as previously disclosed for those components in the unmodified actuation counter of FIGS. 12 to 21.

Where not stated, the components of the drug dispenser devices herein may be made from conventional engineering materials, especially conventional engineering plastics materials, more especially those which allow moulding of the component.

Where plastics materials have been stated for manufacture of a component, such component would typically be formed by injection moulding.

The illustrated drug dispenser devices have inter alia the following advantages:
- a "reduced force to fire" through use of the side levers providing a mechanical advantage;
- a lock-out to prevent inadvertent firing of the device;
- a patient independent firing characteristic through provision of the commitment feature, especially the spring-loading aspect thereof;
- a reliable operation of the actuation counter via the use of the commitment feature;
- an inhalation airflow path which sheaths the drug plume in the mouthpiece thereby reducing deposition of drug on the mouthpiece;
- a closed-off internal mouthpiece geometry which makes it easier to keep the mouthpiece clean; and
- a multi-part stem block which enables complex moulding geometries to be used for the spray channel.

Each of the above-described embodiments of the present invention may be modified to incorporate one or more features disclosed in the U.S. Provisional and/or International Applications incorporated herein by reference in the first and second paragraphs hereof.

It will be appreciated that the mouthpiece 14 in the exemplary embodiments could be configured instead as a nasal nozzle for insertion in a nostril of a human being, so that the drug formulation is deliverable to the nasal cavity of the human being.

The drug dispenser device described herein is suitable for dispensing of a drug formulation to a patient. The drug formulation may take any suitable form and include other suitable ingredients such as diluents, solvents, carriers and propellants.

Administration of drug may be indicated for the treatment of mild, moderate or severe acute or chronic symptoms or for prophylactic treatment. It will be appreciated that the precise dose administered will depend on the age and condition of the patient, the particular drug used and the frequency of administration and will ultimately be at the discretion of the attendant physician. Embodiments are envisaged in which combinations of drugs are employed.

Appropriate drugs may thus be selected from, for example, analgesics, e.g., codeine, dihydromorphine, ergotamine, fentanyl or morphine; anginal preparations, e.g., diltiazem; anti-allergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or $6\alpha,9\alpha$-difluoro-$11\beta$-hydroxy-$16\alpha$-methyl-3-oxo-$17\alpha$-propionyloxy-androsta-1,4-diene-$17\beta$-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), salmefamol, carbuterol, mabuterol, etanterol, naminterol, clenbuterol, flerbuterol, bambuterol, indacaterol, formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); $\alpha_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the drugs may be used in the form of salts, (e.g., as alkali metal or amine salts or as acid addition salts) or as esters (e.g., lower alkyl esters) or as solvates (e.g., hydrates) to optimise the activity and/or stability of the drug.

The drug formulation may in embodiments, be a monotherapy (i.e. single active drug containing) product or it may be a combination therapy (i.e. plural active drugs containing) product.

Suitable drugs or drug components of a combination therapy product are typically selected from the group consisting of anti-inflammatory agents (for example a corticosteroid or an NSAID), anticholinergic agents (for example, an $M_1$, $M_2$, $M_1/M_2$ or $M_3$ receptor antagonist), other $β_2$-adrenoreceptor agonists, antiinfective agents (e.g. an antibiotic or an antiviral), and antihistamines. All suitable combinations are envisaged.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester, 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester and 9α,21 dichloro-11β,17α methyl-1,4 pregnadiene 3, 20 dione-17-[2']furoate (mometasone furoate).

Further corticosteroids are described in WO02/088167, WO02/100879, WO02/12265, WO02/12266, WO05/005451, WO05/005452, WO06/072599 and WO06/072600.

Non-steroidal compounds having glucocorticoid agonism that may possess selectivity for transrepression over transactivation and that may be useful are disclosed WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277, WO06/000401, WO06/000398 and WO06/015870.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists), inhibitors of cytokine synthesis or 5-lipoxygenase inhibitors. Examples of iNOS inhibitors include those disclosed in WO93/13055, WO98/30537, WO02/50021, WO95/34534 and WO99/62875. Examples of CCR3 inhibitors include those disclosed in WO02/26722.

Suitable bronchodilators are $β_2$-adrenoreceptor agonists, including salmeterol (which may be a racemate or a single enantiomer, such as the R-enantiomer), for instance salmeterol xinafoate, salbutamol (which may be a racemate or a single enantiomer, such as the R-enantiomer), for instance salbutamol sulphate or as the free base, formoterol (which may be a racemate or a single diastereomer, such as the R,R-diastereomer), for instance formoterol fumarate or terbutaline and salts thereof. Other suitable $β_2$-adrenoreceptor agonists are 3-(4-{[6-({(2R)-2-hydroxy-2-[4-hydroxy-3-(hydroxymethyl)phenyl]ethyl}amino)hexyl]oxy}butyl)benzenesulfonamide, 3-(3-{[7-({(2R)-2-hydroxy-2-[4-hydroxy-3-hydroxymethyl)phenyl]ethyl}-amino)heptyl]oxy}propyl) benzenesulfonamide, 4-{(1R)-2-[(6-{2-[(2,6-dichlorobenzyl)oxy]ethoxy}hexyl)amino]-1-hydroxyethyl}-2-(hydroxymethyl)phenol, 4-{(1R)-2-[(6-{4-[3-(cyclopentylsulfonyl)phenyl]butoxy}hexyl)amino]-1-hydroxyethyl}-2-(hydroxymethyl)phenol, N-[2-hydroxyl-5-[(1R)-1-hydroxy-2-[[2-4-[[(2R)-2-hydroxy-2-phenylethyl]amino]phenyl]ethyl]amino]ethyl]phenyl]formamide, and N-2{2-[4-(3-phenyl-4-methoxyphenyl)aminophenyl]ethyl}-2-hydroxy-2-(8-hydroxy-2(1H)-quinolinon-5-yl)ethylamine, and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one. Preferably, the $β_2$-adrenoreceptor agonist is a long acting $β_2$-adrenoreceptor agonist (LABA), for example a compound which provides effective bronchodilation for about 12 hours or longer.

Other $β_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Preferred phosphodiesterase 4 (PDE4) inhibitors are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol].

Other suitable drug compounds include: cis-4-cyano-4-[3-(cyclopentyloxy)-4-methoxyphenyl]cyclohexane-1-carboxylic acid (also known as cilomalast) disclosed in U.S. Pat. No. 5,552,438 and its salts, esters, pro-drugs or physical forms; AWD-12-281 from elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Gong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in WO04/024728, WO04/056823 and WO04/103998, all of Glaxo Group Limited.

Suitable anticholinergic agents are those compounds that act as antagonists at the muscarinic receptor, in particular those compounds, which are antagonists of the $M_1$ or $M_3$ receptors, dual antagonists of the $M_1/M_3$ or $M_2/M_3$ receptors or pan-antagonists of the $M_1/M_2/M_3$ receptors. Exemplary compounds include the alkaloids of the belladonna plants as illustrated by the likes of atropine, scopolamine, homatropine, hyoscyamine; these compounds are normally administered as a salt, being tertiary amines.

Other suitable anti-cholinergics are muscarinic antagonists, such as (3-endo)-3-(2,2-di-2-thienylethenyl)-8,8-dimethyl-8-azoniabicyclo[3.2.1]octane iodide, (3-endo)-3-(2-cyano-2,2-diphenylethyl)-8,8-dimethyl-8-azoniabicyclo[3.2.1]octane bromide, 4-[hydroxy(diphenyl)methyl]-1-{2-[(phenylmethyl)oxy]ethyl}-1-azonia bicyclo[2.2.2]octane bromide, (1R,5S)-3-(2-cyano-2,2-diphenylethyl)-8-methyl-8-{2-[(phenylmethyl)oxy]ethyl}-8-azoniabicyclo[3.2.1]octane bromide, (endo)-3-(2-methoxy-2,2-di-thiophen-2-yl-ethyl)-8,8-dimethyl-8-azonia-bicyclo[3.2.1]octane iodide, (endo)-3-(2-cyano-2,2-diphenyl-ethyl)-8,8-dimethyl-8-azonia-bicyclo[3.2.1]octane iodide, (endo)-3-(2-carbamoyl-2,2-diphenyl-ethyl)-8,8-dimethyl-8-azonia-bicyclo[3.2.1]octane iodide, (endo)-3-(2-cyano-2,2-di-thiophen-2-yl-ethyl)-8,8-dimethyl-8-azonia-bicyclo[3.2.1]octane iodide, and (endo)-3-{2,2-diphenyl-3-[(1-phenyl-methanoyl)-amino]-propyl}-8,8-dimethyl-8-azonia-bicyclo[3.2.1]octane bromide.

Particularly suitable anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118. Also of interest are revatropate (for example, as the hydrobromide, CAS 262586-79-8) and LAS-34273 which is disclosed in WO01/04118, darifenacin (CAS133099-04-4, or CAS133099-07-7 for the hydrobromide sold under the name Enablex), oxybutynin (CAS 5633-20-5, sold under the name Ditropan), terodiline (CAS15793-40-5), tolterodine (CAS 124937-51-5, or CAS124937-52-6 for the tartrate, sold under the name Detrol), otilonium (for example, as the bromide, CAS 26095-59-0, sold under the name Spasmomen), trospium chloride (CAS10405-02-4) and solifenacin (CAS 242478-37-1, or CAS 242478-38-2 for the succinate also known as YM-905 and sold under the name Vesicare).

Other anticholinergic agents include compounds disclosed in U.S. Ser. No. 60/487,981 and U.S. Ser. No. 60/511,009.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. Examples include ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine.

Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine.

Exemplary H1 antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlropheniramine and its salts such as the maleate salt, and acrivastine.

piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

The drug, or one of the drugs, may be an H3 antagonist (and/or inverse agonist). Examples of H3 antagonists include, for example, those compounds disclosed in WO2004/035556 and in WO2006/045416.

Other histamine receptor antagonists which may be used include antagonists (and/or inverse agonists) of the H4 receptor, for example, the compounds disclosed in Jablonowski et al., J. Med. Chem. 46:3957-3960 (2003).

Suitably, the drug formulation includes one or more of a $\beta_2$-adrenoreceptor agonist, a corticosteroid, a PDE-4 inhibitor and an anti-cholinergic.

Generally, powdered drug particles suitable for delivery to the bronchial or alveolar region of the lung have an aerodynamic diameter of less than 10 micrometers, preferably from 1-6 micrometers. Other sized particles may be used if delivery to other portions of the respiratory tract is desired, such as the nasal cavity, mouth or throat.

The amount of any particular drug or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The drugs for treatment of respiratory disorders herein may for example, be administered by inhalation at a dose of from 0.0005 mg to 10 mg, preferably 0.005 mg to 0.5 mg. The dose range for adult humans is generally from 0.0005 mg to 100 mg per day and preferably 0.01 mg to 1.5 mg per day.

In one embodiment, the drug is formulated as any suitable aerosol formulation, optionally containing other pharmaceutically acceptable additive components. In embodiments, the aerosol formulation comprises a suspension of a drug in a propellant. In embodiments, the propellant is a fluorocarbon or hydrogen-containing chlorofluorocarbon propellant.

Suitable propellants include, for example, $C_{1-4}$ hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF_2CH_3$; $C_{1-4}$ hydrogen-containing fluorocarbons such as $CHF_2CHF_2$, $CF_3CH_2F$, $CHF_2CH_3$ and $CF_3CHFCF_3$; and perfluorocarbons such as $CF_3CF_3$ and $CF_3CF_2CF_3$.

Where mixtures of the fluorocarbons or hydrogen-containing chlorofluorocarbons are employed they may be mixtures of the above-identified compounds or mixtures, preferably binary mixtures, with other fluorocarbons or hydrogen-containing chloro-fluorocarbons for example $CHClF_2$, $CH_2F_2$ and $CF_3CH_3$. Preferably a single fluorocarbon or hydrogen-containing chlorofluorocarbon is employed as the propellant. Particularly preferred as propellants are $C_{1-4}$ hydrogen-containing fluorocarbons such as 1,1,1,2-tetrafluoroethane ($CF_3CH_2F$) and 1,1,1,2,3,3,3-heptafluoro-n-propane ($CF_3CHFCF_3$) or mixtures thereof.

The drug formulations are preferably substantially free of chlorofluorocarbons such as $CCl_3F$, $CCl_2F_2$ and $CF_3CCl_3$. Preferably, the propellant is liquefied HFA134a or HFA-227 or mixtures thereof.

The propellant may additionally contain a volatile adjuvant such as a saturated hydrocarbon for example propane, n-butane, liquefied, pentane and is pentane or a dialkyl ether for example dimethyl ether. In general, up to 50% w/w of the propellant may comprise a volatile hydrocarbon, for example 1 to 30% w/w. However, formulations, which are free or substantially free of volatile adjuvants are preferred. In certain cases, it may be desirable to include appropriate amounts of water, which can be advantageous in modifying the dielectric properties of the propellant.

A polar co-solvent such as $C_{2-6}$ aliphatic alcohols and polyols e.g. ethanol, isopropanol and propylene glycol, preferably ethanol, may be included in the drug formulation in the desired amount to improve the dispersion of the formulation, either as the only excipient or in addition to other excipients such as surfactants. In embodiments, the drug formulation may contain 0.01 to 5% w/w based on the propellant of a polar co-solvent e.g. ethanol, preferably 0.1 to 5% w/w e.g. about 0.1 to 1% w/w. In embodiments herein, the solvent is added in sufficient quantities to solubilise part or all of the drug component, such formulations being commonly referred to as 'solution' aerosol drug formulations.

A surfactant may also be employed in the aerosol formulation. Examples of conventional surfactants are disclosed in EP-A-372,777. The amount of surfactant employed is desirable in the range 0.0001% to 50% weight to weight ratio relative to the drug, in particular, 0.05 to 10% weight to weight ratio.

The aerosol drug formulation desirably contains 0.005-10% w/w, preferably 0.005 to 5% w/w, especially 0.01 to 2% w/w, of drug relative to the total weight of the formulation.

In another embodiment, the drug is formulated as any suitable fluid formulation, particularly a solution (e.g. aqueous) formulation or a suspension formulation, optionally containing other pharmaceutically acceptable additive components.

Suitable formulations (e.g. solution or suspension) may be stabilised (e.g. using hydrochloric acid or sodium hydroxide) by appropriate selection of pH. Typically, the pH will be adjusted to between 4.5 and 7.5, preferably between 5.0 and 7.0, especially around 6 to 6.5.

Suitable formulations (e.g. solution or suspension) may comprise one or more excipients. By the term "excipient", herein, is meant substantially inert materials that are nontoxic and do not interact with other components of a composition in a deleterious manner including, but not limited to, pharmaceutical grades of carbohydrates, organic and inorganic salts, polymers, amino acids, phospholipids, wetting agents, emulsifiers, surfactants, poloxamers, pluronics, and ion exchange resins, and combinations thereof.

Suitable carbohydrates include monosaccharides include fructose; disaccharides, such as, but not limited to lactose, and combinations and derivatives thereof; polysaccharides, such as, but not limited to, cellulose and combinations and derivatives thereof; oligosaccharides, such as, but not limited to, dextrins, and combinations and derivatives thereof; polyols, such as but not limited to sorbitol, and combinations and derivatives thereof.

Suitable organic and inorganic salts include sodium or calcium phosphates, magnesium stearate, and combinations and derivatives thereof.

Suitable polymers include natural biodegradable protein polymers, including, but not limited to, gelatin and combinations and derivatives thereof; natural biodegradable polysaccharide polymers, including, but not limited to, chitin and starch, crosslinked starch and combinations and derivatives thereof; semisynthetic biodegradable polymers, including, but not limited to, derivatives of chitosan; and synthetic biodegradable polymers, including, but not limited to, polyethylene glycols (PEG), polylactic acid (PLA), synthetic polymers including but not limited to polyvinyl alcohol and combinations and derivatives thereof.

Suitable amino acids include non-polar amino acids, such as leucine and combinations and derivatives thereof. Suitable phospholipids include lecithins and combinations and derivatives thereof.

Suitable wetting agents, surfactants and/or emulsifiers include gum acacia, cholesterol, fatty acids including combinations and derivatives thereof. Suitable poloxamers and/or Pluronics include poloxamer 188, Pluronic® F-108, and combinations and derivations thereof. Suitable ion exchange resins include amberlite IR120 and combinations and derivatives thereof.

Suitable solution formulations may comprise a solubilising agent such as a surfactant. Suitable surfactants include α-[4-(1,1,3,3-tetramethylbutyl)phenyl]-ω-hydroxypoly (oxy-1,2-ethanediyl) polymers including those of the Triton series e.g. Triton X-100, Triton X-114 and Triton X-305 in which the X number is broadly indicative of the average number of ethoxy repeating units in the polymer (typically around 7-70, particularly around 7-30 especially around 7-10) and 4-(1,1,3,3-tetramethylbutyl)phenol polymers with formaldehyde and oxirane such as those having a relative molecular weight of 3500-5000 especially 4000-4700, particularly Tyloxapol. The surfactant is typically employed in a concentration of around 0.5-10%, preferably around 2-5% w/w based on weight of formulation.

Suitable solution formulations may also comprise hydroxyl containing organic co-solvating agents include glycols such as polyethylene glycols (e.g. PEG 200) and propylene glycol; sugars such as dextrose; and ethanol. Dextrose and polyethylene glycol (e.g. PEG 200) are preferred, particularly dextrose. Propylene glycol is preferably used in an amount of no more than 20%, especially no more than 10% and is most preferably avoided altogether. Ethanol is preferably avoided. The hydroxyl containing organic co-solvating agents are typically employed at a concentration of 0.1-20% e.g. 0.5-10%, e.g. around 1-5% w/w based on weight of formulation.

Suitable solution formulations may also comprise solubilising agents such as polysorbate, glycerine, benzyl alcohol, polyoxyethylene castor oils derivatives, polyethylene glycol and polyoxyethylene alkyl ethers (e.g. Cremophors, Brij).

Suitable solution formulations may also comprise one or more of the following components: viscosity enhancing agents; preservatives; and isotonicity adjusting agents.

Suitable viscosity enhancing agents include carboxymethylcellulose, veegum, tragacanth, bentonite, hydroxypropylmethylcellulose, hydroxypropylcellulose, hydroxyethylcellulose, poloxamers (e.g. poloxamer 407), polyethylene glycols, alginates xanthym gums, carageenans and carbopols.

Suitable preservatives include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts and polymyxin.

Suitable isotonicity adjusting agents act such as to achieve isotonicity with body fluids (e.g. fluids of the nasal cavity), resulting in reduced levels of irritancy associated with many nasal formulations. Examples of suitable isotonicity adjusting agents are sodium chloride, dextrose and calcium chloride.

Suitable suspension formulations comprise an aqueous suspension of particulate drug and optionally suspending agents, preservatives, wetting agents or isotonicity adjusting agents.

Suitable suspending agents include carboxymethylcellulose, veegum, tragacanth, bentonite, methylcellulose and polyethylene glycols.

Suitable wetting agents function to wet the particles of drug to facilitate dispersion thereof in the aqueous phase of the composition. Examples of wetting agents that can be used are fatty alcohols, esters and ethers. Preferably, the wetting agent is a hydrophilic, non-ionic surfactant, most preferably polyoxyethylene (20) sorbitan monooleate (supplied as the branded product Polysorbate 80).

Suitable preservatives and isotonicity adjusting agents are as described above in relation to solution formulations.

The drug dispenser device herein is in one embodiment suitable for dispensing aerosolized drug (e.g. for inhalation via the mouth) for the treatment of respiratory disorders such as disorders of the lungs and bronchial tracts including asthma and chronic obstructive pulmonary disorder (COPD). In another embodiment, the invention is suitable for dispensing aerosolized drug (e.g. for inhalation via the mouth) for the treatment of a condition requiring treatment by the systemic circulation of drug, for example migraine, diabetes, pain relief e.g. inhaled morphine.

Administration of drug in aerosolized form may be indicated for the treatment of mild, moderate or severe acute or chronic symptoms or for prophylactic treatment. It will be appreciated that the precise dose administered will depend on the age and condition of the patient, the particular particulate drug used and the frequency of administration and will ultimately be at the discretion of the attendant physician. When combinations of drugs are employed the dose of each component of the combination will in general be that employed for each component when used alone. Typically, administration may be one or more times, for example from 1 to 8 times per day, giving for example 1, 2, 3 or 4 aerosol puffs each time. Each valve actuation, for example, may deliver 5 µg, 50 µg, 100 µg, 200 µg or 250 µg of a drug. Typically, each filled canister for use in a metered dose inhaler contains 60, 100, 120 or 200 metered doses or puffs of drug; the dosage of each drug is either known or readily ascertainable by those skilled in the art.

In another embodiment, the drug dispenser device herein is suitable for dispensing fluid drug formulations for the treatment of inflammatory and/or allergic conditions of the nasal passages such as rhinitis e.g. seasonal and perennial rhinitis as well as other local inflammatory conditions such as asthma, COPD and dermatitis. A suitable dosing regime would be for the patient to inhale slowly through the nose subsequent to the nasal cavity being cleared. During inhalation the formulation would be applied to one nostril while the other is manually compressed. This procedure would then be repeated for the other nostril. Typically, one or two inhalations per nostril would be administered by the above procedure up to three times each day, ideally once daily. Each dose, for example, may deliver 5 µg, 50 µg, 100 µg, 200 µg or 250 µg of active drug. The precise dosage is either known or readily ascertainable by those skilled in the art.

It will be understood that the present invention has been described above by way of example only and that the above description can be modified in many different ways without departing from the scope of the invention as defined by the appended claims.

All publications, patents, and patent applications cited herein, and any US patent family equivalent to any such patent or patent application, are hereby incorporated herein by reference to their entirety to the same extent as if each publication, patent, or patent application was specifically and individually indicated to be incorporated by reference.

It must be noted that, as used in the specification and appended claims, the singular forms "a", "an", "the" and "one" include plural referents unless the content clearly dictates otherwise.

What is claimed is:

1. An actuation counter comprising:
a driver feature having one or more driver elements, which driver feature is arranged for drivable movement in response to an actuation; and
a first count member and a second count member, the first count member including one or more drive receipt elements arranged thereon for receipt of drive from said one or more driver elements of the driver feature for drivable movement of the first count member;
wherein the driver feature includes one or more brake elements arranged to selectively interact with the first count member and the second count member to prevent overrun thereof when registering a count of an actuation.

2. An actuation counter according to claim 1, wherein the counter is arranged for use with a drug dispenser device.

3. An actuation counter according to claim 1 wherein the first count member is a first count wheel arranged to rotate about a first axis of rotation, said first count wheel including one or more drive receipt elements arranged thereon for receipt of rotary drive from said one or more driver elements of the driver feature for drivable rotation of the first count wheel about said first axis of rotation.

4. An actuation counter according to claim 1, wherein the second count member is a second count wheel arranged to rotate about the first axis of rotation, said second count wheel including a set of teeth arranged annularly thereon.

5. An actuation counter according to claim 4, wherein the counter further comprises a wheel coupler arranged for movement, said wheel coupler including a set of coupling teeth arranged thereon and in meshed relationship with the set of teeth of the second count wheel such that motion of the wheel coupler results in rotary motion of the second count wheel.

6. An actuation counter according to claim 5, wherein said first count wheel further includes at least one fixed index tooth arranged for intermittent meshing with the coupling teeth of the wheel coupler such that motion of the wheel coupler results from rotary motion of the first count wheel only when said intermittent meshing occurs.

7. An actuation counter according to claim 5, wherein the wheel coupler is arranged for rotary movement about an axis of rotation.

8. An actuation counter according to claim 6, wherein the wheel coupler is a kick wheel arranged to rotate about a second axis of rotation offset from the first axis of rotation, and wherein the set of coupling teeth of said kick wheel comprise a set of kick teeth arranged thereon and in meshed relationship with the set of teeth of the second count wheel such that rotary motion of the kick wheel results in rotary motion of the second count wheel, and wherein said at least one fixed index tooth of the first count wheel is arranged for intermittent meshing with the kick teeth of the kick wheel such that rotary motion of the kick wheel results from rotary motion of the first count wheel only when said intermittent meshing occurs.

9. An actuation counter according to claim 8, wherein the set of kick teeth of the kick wheel are arranged annularly thereon.

10. An actuation counter according to claim 2, wherein the driver feature is arranged for connection with a movable element of the drug dispenser device that moves in response to actuation of the drug dispenser device.

11. An actuation counter according to claim 1, wherein the driver feature comprises a driver plate.

12. An actuation counter according to claim 1, wherein each of the driver elements has a form selected from the group consisting of a protrusion, an abutment, a rib, an indent and a slot provided to the driver feature.

13. An actuation counter according to claim 1, wherein the one or more brake elements are arranged such that any one actuation registers as only a single count.

14. An actuation counter according to claim 4, wherein the one or more brake elements are arranged to selectively interact with the first count wheel and the second count wheel to allow only a pre-determined degree of rotation thereof when registering a count of an actuation.

15. An actuation counter according to claim 14, wherein the pre-determined degree of rotation of the first count wheel corresponds to that of the second count wheel.

16. An actuation counter according to claim 14, wherein the pre-determined degree of rotation of the first count wheel is different from that of the second count wheel.

17. An actuation counter according to claim 4, wherein the one or more brake elements are initially spaced from the first count wheel and the second count wheel and brought into proximity for selective interaction therewith in response to drivable movement of the driver feature.

18. An actuation counter according to claim 17, wherein the one or more brake elements are brought into such proximity at a point in an actuation counting operation when the first and the second count wheels have been rotated on sufficiently that a single count has been registered.

19. An actuation counter according to claim 1, wherein the driver feature is movable in response to an actuation to position the one or more brake elements in a braking position to physically prevent overrun of the first and second count members.

20. An actuation counter according to claim 19, wherein in the braking position the one or more brake elements interleave with one or more brake receipt elements of the first count wheel and of the second count wheel.

21. An actuation counter according to claim 20, wherein the first and second count members are wheels, wherein each wheel has a circumferential surface which is notched to form the respective brake receipt elements, and wherein the one or more brake elements fit in notches of the wheels when in the braking position.

22. An actuation counter according to claim 21, wherein each circumferential surface is serrated to form the respective notches.

23. An actuation counter according to claim 22, wherein the serrations are provided with a generally-radial leading edge.

24. An actuation counter according to claim 21, wherein the first and second count wheels are co-axially arranged for rotation on an axis of rotation.

25. An actuation counter according to claim 19, wherein the driver feature comprises a first part including the one or more brake elements and a second part including the one or more driver elements, and wherein the first part is adapted to move in response to an actuation and to drive movement of the second part to cause movement of the first count member through interaction of the one or more driver elements and the one or more drive receipt elements.

26. An actuation counter according to claim 25, wherein the first and second count members are wheels co-axially arranged for rotation on an axis of rotation, wherein each wheel has a circumferential surface which is notched to form respective brake receipt elements, wherein the one or more brake elements fit in notches of the wheels when in the braking position, and wherein the second part of the driver feature is a wheel arranged to be rotated on the axis of rotation by the first part to drive rotation of the first count wheel.

27. An actuation counter according to claim 26, wherein the first part is arranged to move linearly in response to an actuation and is coupled to the second part so that its linear movement drives rotary movement of the second part about the axis of rotation.

* * * * *